US00RE51085E

(19) United States
(12) Reissued Patent
Pillarisetti et al.

(10) Patent Number: US RE51,085 E
(45) Date of Reissued Patent: Oct. 20, 2026

(54) ANTI-BCMA ANTIBODIES AND USES THEREOF

(71) Applicant: Janssen Biotech, Inc., Horsham, PA (US)

(72) Inventors: Kodandaram Pillarisetti, Spring House, PA (US); Eric Thomas Baldwin, Spring House, PA (US); Gordon D. Powers, Spring House, PA (US); Rosa Maria Fernandes Cardosa, Spring House, PA (US); Ricardo Attar, Spring House, PA (US); Francois Gaudet, Spring House, PA (US)

(73) Assignee: Janssen Biotech, Inc., Horsham, PA (US)

(21) Appl. No.: 17/739,055

(22) Filed: May 6, 2022

Related U.S. Patent Documents

Reissue of:
(64) Patent No.: 10,072,088
Issued: Sep. 11, 2018
Appl. No.: 15/237,889
Filed: Aug. 16, 2016

U.S. Applications:
(60) Provisional application No. 62/206,246, filed on Aug. 17, 2015.

(51) Int. Cl.

| | |
|---|---|
| ***C07K 16/28*** | (2006.01) |
| ***A61K 39/00*** | (2006.01) |
| ***A61K 39/395*** | (2006.01) |
| ***A61K 45/06*** | (2006.01) |
| ***C07K 16/30*** | (2006.01) |

(52) U.S. Cl.
CPC .... *C07K 16/2878* (2013.01); *A61K 39/39558* (2013.01); *A61K 45/06* (2013.01); *C07K 16/2809* (2013.01); *C07K 16/3061* (2013.01); *A61K 2039/505* (2013.01); *C07K 2317/21* (2013.01); *C07K 2317/31* (2013.01); *C07K 2317/33* (2013.01); *C07K 2317/34* (2013.01); *C07K 2317/515* (2013.01); *C07K 2317/565* (2013.01); *C07K 2317/76* (2013.01); *C07K 2317/92* (2013.01)

(58) Field of Classification Search
CPC .. A61K 39/39558; A61K 45/06; A61K 35/02; A61K 16/3061; A61K 16/2878; A61P 35/00; C07K 16/2809
See application file for complete search history.

(56) References Cited

U.S. PATENT DOCUMENTS

| | | | |
|---|---|---|---|
| 5,223,409 | A | 6/1993 | Ladner et al. |
| 5,403,484 | A | 4/1995 | Ladner et al. |
| 5,427,908 | A | 6/1995 | Dower et al. |
| 5,571,698 | A | 11/1996 | Ladner et al. |
| 5,580,717 | A | 12/1996 | Dower et al. |
| 5,885,793 | A | 3/1999 | Griffiths et al. |
| 5,932,448 | A | 8/1999 | Tso et al. |
| 5,969,108 | A | 10/1999 | McCafferty et al. |
| 6,172,197 | B1 | 1/2001 | McCafferty et al. |
| 6,521,404 | B1 | 2/2003 | Griffiths et al. |
| 6,521,427 | B1 | 2/2003 | Evans |
| 6,544,731 | B1 | 4/2003 | Griffiths et al. |
| 6,555,313 | B1 | 4/2003 | Griffiths et al. |
| 6,582,915 | B1 | 6/2003 | Griffiths et al. |
| 6,593,081 | B1 | 7/2003 | Griffiths et al. |
| 6,670,127 | B2 | 12/2003 | Evans |
| 6,737,056 | B1 | 5/2004 | Presta |
| 6,833,441 | B2 | 12/2004 | Wang et al. |
| 7,829,673 | B2 | 11/2010 | De Weers et al. |
| 7,994,289 | B2 | 8/2011 | Waldmann et al. |
| 8,088,896 | B2 | 1/2012 | Tesar et al. |
| 8,153,765 | B2 | 4/2012 | Park et al. |

(Continued)

FOREIGN PATENT DOCUMENTS

| | | | |
|---|---|---|---|
| CN | 103842383 | A | 6/2014 |
| CN | 104114186 | A | 10/2014 |

(Continued)

OTHER PUBLICATIONS

Li, et al., "Effect of PS-341 on Multiple Myeloma Cells Migrationa nd Secretion BAFF and APRIL," *Aerospace Medicine*, 21(6):885-888, (Jun. 2010).
NCT03145181 "Dose Escalation Study of Teclistamab, a Humanized BCMA*CD3 Bispecific Antibody, in Participants With Relapsed or Refractory Multiple Myeloma (Majes TEC-1)," ClinicalTrials.gov identifier: NCT03145181 (Apr. 25, 2019) pp. 1-10.
Shah et al., "B-cell maturation antigen (BCMA) in multiple myeloma: rationale for targeting and current therapeutic approaches," Leukemia (2020) vol. 34, pp. 985-1005.
Girgis et al., "Exploratory Pharmacokinetic/Pharmacodynamic and Tolerability Study of BCMAxCD3 in Cynomolgus Monkeys," Blood (2016) vol. 128(22), p. 5668.

(Continued)

*Primary Examiner* — Kevin S Orwig
(74) *Attorney, Agent, or Firm* — Troutman Pepper Locke LLP

(57) ABSTRACT

Provided herein are antibodies that immunospecifically bind to BCMA. Also described are related polynucleotides capable of encoding the provided BCMA-specific antibodies or antigen-binding fragments, cells expressing the provided antibodies or antigen-binding fragments, as well as associated vectors and detectably labeled antibodies or antigen-binding fragments. In addition, methods of using the provided antibodies are described. For example, the provided antibodies may be used to diagnose, treat, or monitor BCMA-expressing cancer progression, regression, or stability; to determine whether or not a patient should be treated for cancer; or to determine whether or not a subject is afflicted with BCMA-expressing cancer and thus may be amenable to treatment with a BCMA-specific anti-cancer therapeutic, such as the multispecific antibodies against BCMA and CD3 described herein.

34 Claims, 28 Drawing Sheets

Specification includes a Sequence Listing.

(56) References Cited

U.S. PATENT DOCUMENTS

| | | | |
|---|---|---|---|
| 8,236,308 | B2 | 8/2012 | Kischel et al. |
| 9,150,663 | B2 | 10/2015 | Labrijn et al. |
| 10,072,088 | B2 | 9/2018 | Pillarisetti et al. |
| 10,562,968 | B2 | 2/2020 | Attar et al. |
| 11,685,777 | B2 | 6/2023 | Attar et al. |
| 11,884,722 | B2 | 1/2024 | Attar et al. |
| 11,952,426 | B2 | 4/2024 | Adams et al. |
| 12,012,461 | B2 | 6/2024 | Adams et al. |
| 12,065,500 | B2 | 8/2024 | Adams et al. |
| 12,098,210 | B2 | 9/2024 | Goldberg et al. |
| 2002/0198362 | A1 | 12/2002 | Gaiger et al. |
| 2005/0019320 | A1 | 1/2005 | Sugaru et al. |
| 2005/0276803 | A1 | 12/2005 | Chan et al. |
| 2007/0287170 | A1 | 12/2007 | Davis et al. |
| 2009/0182127 | A1 | 7/2009 | Kjaergaard et al. |
| 2010/0015133 | A1 | 1/2010 | Igawa et al. |
| 2010/0028637 | A1 | 2/2010 | Tavsanli et al. |
| 2010/0092489 | A1 | 4/2010 | Van De Winkel et al. |
| 2011/0123532 | A1 | 5/2011 | Gurney et al. |
| 2011/0206660 | A1 | 8/2011 | Blanchetot et al. |
| 2012/0149876 | A1 | 6/2012 | Von Kreudenstein et al. |
| 2013/0156769 | A1 | 6/2013 | Kufer et al. |
| 2013/0195849 | A1 | 8/2013 | Spreter Von Kreudenstein et al. |
| 2014/0051662 | A1 | 2/2014 | Moussy et al. |
| 2014/0112962 | A1 | 4/2014 | Kim et al. |
| 2014/0154254 | A1 | 6/2014 | Kannan et al. |
| 2014/0303356 | A1 | 10/2014 | Gramer et al. |
| 2014/0323315 | A1 | 10/2014 | Bobrowicz et al. |
| 2014/0341925 | A1 | 11/2014 | Krause et al. |
| 2015/0246975 | A1 | 9/2015 | Doshi |
| 2016/0166689 | A1 | 6/2016 | Adler et al. |
| 2017/0051068 | A1 | 2/2017 | Pillarisetti et al. |
| 2018/0037651 | A1 | 2/2018 | Attar et al. |
| 2019/0352421 | A1 | 11/2019 | Adams et al. |
| 2020/0179511 | A1 | 6/2020 | Daley et al. |
| 2020/0190205 | A1 | 6/2020 | Adams et al. |
| 2020/0308284 | A1 | 10/2020 | Bandekar et al. |
| 2022/0041742 | A1 | 2/2022 | Adams et al. |
| 2022/0177584 | A1 | 6/2022 | Girgis et al. |
| 2022/0373550 | A1 | 11/2022 | Pillarisetti et al. |
| 2022/0411525 | A1 | 12/2022 | Adams, III et al. |
| 2023/0084967 | A1 | 3/2023 | Attar et al. |
| 2023/0227548 | A1 | 7/2023 | Attar et al. |
| 2023/0272102 | A1 | 8/2023 | Goldberg et al. |
| 2023/0279136 | A1 | 9/2023 | Muzammil et al. |
| 2023/0295292 | A1 | 9/2023 | Goldberg et al. |
| 2024/0076376 | A1 | 3/2024 | Goldberg et al. |
| 2024/0101697 | A1 | 3/2024 | Adams et al. |
| 2024/0301083 | A1 | 9/2024 | Adams et al. |
| 2024/0343796 | A1 | 10/2024 | Attar et al. |
| 2024/0352140 | A1 | 10/2024 | Adams, III et al. |
| 2024/0392027 | A1 | 11/2024 | Vargo et al. |
| 2024/0400702 | A1 | 12/2024 | Zakrewsky et al. |
| 2024/0415960 | A1 | 12/2024 | Kobos et al. |
| 2025/0064928 | A1 | 2/2025 | Kobos et al. |
| 2025/0109211 | A1 | 4/2025 | Goldberg et al. |
| 2025/0242019 | A2 | 7/2025 | Kobos et al. |
| 2025/0362298 | A1 | 11/2025 | Pillarisetti et al. |

FOREIGN PATENT DOCUMENTS

| | | | |
|---|---|---|---|
| CN | 104114578 | A | 10/2014 |
| EP | 0999853 | B1 | 1/2003 |
| EP | 2762497 | A1 | 8/2014 |
| EP | 2982692 | A1 | 2/2016 |
| EP | 3337824 | A1 | 6/2018 |
| FR | 2994803 | B1 | 2/2016 |
| TW | 201326214 | A | 7/2013 |
| TW | 201623333 | A | 7/2016 |
| WO | 1988001649 | A1 | 3/1988 |
| WO | 1992001047 | A1 | 1/1992 |
| WO | 1994013804 | A1 | 6/1994 |
| WO | 1996027011 | A1 | 9/1996 |
| WO | 1998044001 | A1 | 10/1998 |
| WO | 200041474 | A2 | 7/2000 |
| WO | 200124811 | A1 | 4/2001 |
| WO | 200124812 | A1 | 4/2001 |
| WO | 2002066516 | A2 | 8/2002 |
| WO | 2003072713 | A2 | 9/2003 |
| WO | 2004078140 | A2 | 9/2004 |
| WO | 2005086568 | A2 | 9/2005 |
| WO | 2006028936 | A2 | 3/2006 |
| WO | WO-2007042261 | A2 | 4/2007 |
| WO | 2007059782 | A1 | 5/2007 |
| WO | 2007117600 | A2 | 10/2007 |
| WO | 2008119565 | A2 | 10/2008 |
| WO | 2008119566 | A2 | 10/2008 |
| WO | 2008119567 | A2 | 10/2008 |
| WO | 2009085462 | A1 | 7/2009 |
| WO | 2009132058 | A2 | 10/2009 |
| WO | 2009134776 | A2 | 11/2009 |
| WO | 2010037836 | A2 | 4/2010 |
| WO | 2010037837 | A2 | 4/2010 |
| WO | 2010037838 | A2 | 4/2010 |
| WO | 2010051274 | A2 | 5/2010 |
| WO | 2010093627 | A2 | 8/2010 |
| WO | 2010104949 | A2 | 9/2010 |
| WO | 2011131746 | A2 | 10/2011 |
| WO | 2011143545 | A1 | 11/2011 |
| WO | 2012022811 | A1 | 2/2012 |
| WO | 2012040518 | A2 | 3/2012 |
| WO | 2012066058 | A1 | 5/2012 |
| WO | 2012143498 | A1 | 10/2012 |
| WO | WO-2012158818 | A2 | 11/2012 |
| WO | 2012163805 | A1 | 12/2012 |
| WO | WO-2013020074 | A2 | 2/2013 |
| WO | 2013072406 | A1 | 5/2013 |
| WO | 2013072415 | A1 | 5/2013 |
| WO | 2013096291 | A2 | 6/2013 |
| WO | 2013157954 | A1 | 10/2013 |
| WO | WO-2013158856 | A2 | 10/2013 |
| WO | WO-2014056783 | A1 | 4/2014 |
| WO | 2014068079 | A1 | 5/2014 |
| WO | 2014089335 | A2 | 6/2014 |
| WO | 2014089416 | A1 | 6/2014 |
| WO | 2014093908 | A2 | 6/2014 |
| WO | 2014100689 | A1 | 6/2014 |
| WO | 2014122144 | A1 | 8/2014 |
| WO | WO-2014122143 | A1 | 8/2014 |
| WO | WO-2014124143 | A1 | 8/2014 |
| WO | 2014131712 | A1 | 9/2014 |
| WO | WO-2014140248 | A1 | 9/2014 |
| WO | WO-2014145806 | A2 | 9/2014 |
| WO | WO-2015052536 | A1 | 4/2015 |
| WO | 2015149077 | A1 | 10/2015 |
| WO | 2016036937 | A1 | 3/2016 |
| WO | 2016040294 | A2 | 3/2016 |
| WO | 2016090034 | A2 | 6/2016 |
| WO | 2016090312 | A1 | 6/2016 |
| WO | 2016090329 | A2 | 6/2016 |
| WO | 2016094304 | A2 | 6/2016 |
| WO | 2020261093 | A1 | 12/2020 |

OTHER PUBLICATIONS

Zhao et al., "Bispecific antibodies targeting BCMA, GPRC5D, and FcRH5 for multiple myeloma therapy: latest updates from ASCO 2023 Annual Meeting," Journal of Hematology & Oncology (2023) vol. 16(92), pp. 1-4.

Chen, et al., "Thymoglobulin Efficiently Explands Cytokine-Induced Killer Cells in a Clinical-Grade Culture Protocol," *Chin. J. Cell. Mol. Immunol.*, 30(7):681-690, (2014).

Delano, "PyMOL: An Open-Source Molecular Graphics Tool," *Delano Scientific*, pp. 1-9, (2002).

Emsley, et al., Cool: Model-Building Tools for Molecular Graphics, *Acta Crystallogr D Biol Crystallogr*, 60(Pt 12 Pt 1):2126-32, (2004).

Gross, et al., "TACI and BCMA are Receptors for a TNF Homologue Implicated in B-Cell Autoimmune Disease," *Nature*, 404:995-999, (Apr. 27, 2000).

Hymowitz, et al., "Structures of APRIL-Receptor Complexes," *The Journal of Biological Chemistry*, 280(8):7218-7227, (Feb. 25, 2005).

(56) References Cited

OTHER PUBLICATIONS

Keymeulen, et al., "Insulin Needs after CDS-Antibody Therapy in New-Onset Type 1 Diabetes," *The New England Journal of Medicine*, 352(25):2598-2608, (Jun. 23, 2005).
Laabi, et al., "A New Gene, BCM, on Chromosome 16 is Fused to the Interleukin 2 Gene by a t(4;16)(q26;p13) Translocation in a Malignant T Cell Lymphoma," *The EMBO Journal*, 11(11):3897-3904, (1992).
Liu, et al., "Ligand-Receptor Binding Revealed by the TNF Family Member TALL-1," *Nature*, 423:49-56, (May 1, 2003).
Myers, et al., "Optimal Alignments in Linear Space," *Cabios*, 4(1):11-17, (1988).
Rickert, et al., "Signaling by the TNFR Superfamily in B-Cell Biology and Disease," *Immunol, Rev.*, 244(1):115-133, Nov. 2011).
International Search Report from Application No. PCT/US2016/047146, dated Oct. 26, 2016.
Drach et al., "Presence of a p53 Gene Deletion in Patients with Multiple Myeloma Predicts for Short Survival After Conventional-Dose Chemotherapy," Blood (1998) vol. 92(3), pp. 802-809.
European Search Report for European Patent Application No. 20177664.8 dated Nov. 23, 2020.
Facon et al., "Chromosome 13 Abnormalities Identified by FISH Analysis and Serum ?2-microglobulin Produce a Powerful Myeloma Staging System for Patients Receiving High-Dose Therapy," Blood (Mar. 15, 2001) vol. 91(6), pp. 1566-1571.
Gertz et al., "Clinical Implications of t(11;14)(q13;q32), t(4;14)(p16.3;q32), and 17p13 in Myeloma Patients Treated with High-Dose Therapy," Blood (2005) vol. 106(8), pp. 2837-2840.
Madry et al., "The Characterization of Murine BCMA Gene Defines it as a New Member of the Tumor Necrosis Factor Receptor Superfamily," Int Immunol (1998) vol. 10, No. 11, pp. 1693-1702.
Non-Final Office Action for U.S. Appl. No. 15/237,889 dated Aug. 17, 2017.
Notice of Allowance for U.S. Appl. No. 15/237,889 dated Jan. 22, 2018.
Notice of Allowance for U.S. Appl. No. 15/237,889 dated May 9, 2018.
Novak et al., "Expression of BCMA, TACI, and BAFF-R in Multiple Myeloma: A Mechanism for Growth and Survival," Blood (Jan. 15, 2004) vol. 103(2). pp. 689-694.
Restriction Requirement for U.S. Appl. No. 15/237,889 dated Jun. 5, 2017.
U.S. Appl. No. 18/052,174, filed Nov. 2, 2022.
U.S. Appl. No. 18/053,904, filed Nov. 9, 2022.
Le Basle et al., "Physicochemical Stability of Monoclonal Antibodies: A Review," Journal of Pharmaceutical Sciences (Jan. 2020) 109(1): 169-190.
NCI Thesaurus, Teclistamab, Accessed Jan. 2, 2025, https://pubchem.ncbi.nlm.nih.gov/compound/Teclistamab, 13 pgs.
NCT03145181, Dose Escalation of Teclistamab, a Humanized BCMAxCD3 Bispecific Antibody, in Participants with Relapsed or Refractory Multiple Myeloma (MajesTEC-1), Janssen, Clinical Trial, ClinicalTrials.gov, Record History published Oct. 29, 2020, Last Update Posted Dec. 6, 2024, 18 pgs.
Strickley et al., "A Review of Formulations of Commercially Available Antibodies," Journal of Pharmaceutical Sciences (Mar. 1, 2021) vol. 110, No. 7, pp. 2590-5608.
Kang et al., "Rapid Formulation Development for Monoclonal Antibodies," BioProcess International (Apr. 2016) vol. 14, No. 4, pp. 40, 42, 44, 46.
Adriouch et al., "Extracellular Nad+: A Danger Signal Hindering Regulatory T Cells," Microbes and Infect. (Nov. 2012) vol. 14, Issue 14, pp. 1284-1292.
Almagro et al., "Humanization of Antibodies," Frontiers in Bioscience (2008) vol. 13, pp. 1619-1633.
Almagro, "Identification of Differences in the Specificity-Determining Residues of Antibodies that Recognize Antigens of Different Size: Implications for the Rational Design of Antibody Repertoires," J. Mol. Recognit. (2004) vol. 17, pp. 132-143.
Anonymous, "Human GPRC5D APC-Conjugated Antibody," (Oct. 12, 2015) URL: https://resources.mdsystems.com/pdfs/datasheets/fab6300a.pdf, abstract, XP055408560.
Ansell et al., "Denileukin Diftitox in Combination with Rituximab for Previously Untreated Follicular B-Cell Non-Hodgkin's Lymphoma," Blood (Oct. 21, 2011) vol. 26, No. 5, pp. 1046-1052.
Atamaniuk et al., "Overexpression of G Protein-Coupled Receptor 5D in the Bone Marrow is Associated with Poor Prognosis in Patients with Multiple Myeloma," Eur J Clin Invest (Sep. 2012) vol. 42(9), pp. 953-960.
Atanackovic et al., "Chimeric Antigen Receptor (CAR) Therapy for Multiple Myeloma," Br. J. Haematol. (2016) 172(5), pp. 685-698.
Avery et al., "BAFF Selectively Enhances the Survival of Plasmablasts Generated from Human Memory B Cells," J Clin Invest. (2003) vol. 112(2), pp. 286-297.
Avet-Loiseau et al. "Evaluation of Minimal Residual Disease (MRD) By Next Generation Sequencing (NGS) is Highly Predictive of Progression Free Survival in the IFM/DFCI 2009 Trial," Blood (Dec 3, 2015) vol. 126, No. 23, p. 191.
Babb et al., "Cancer Phase I Clinical Trials: Efficient Dose Escalation with Overdose Control," Stat. Med. (1998) vol. 17, pp. 1103-1120.
Baert et al., "Influence of Immunogenicity on the Long-Term Efficacy of Infliximab in Crohn's Disease," N. Engl. J. Med. (2003) vol. 348, pp. 601-608.
Ben Safta et al., "Granzyme B-activated p53 Interacts with Bcl-2 to Promote Cytotoxic Lymphocyte-Mediated Apoptosis," J Immunol (2015) vol. 194(1), pp. 418-428.
Bird et al., "The Granzyme B-Serpinb9 Axis Controls the Fate of Lymphocytes after Lysosomal Stress," Cell Death Differ (Jan. 2014) vol. 21, pp. 876-887.
Bossen et al., "Baff, April and their Receptors: Structure, Function and Signaling," Seminars in Immunology (2006) vol. 18, pp. 263-275.
Brauner-Osborne et al., "Cloning and Characterization of a Human Orphan Family C G-protein Coupled Receptor GPRC5D," Biochimeca et Biophysica Acta (2001) vol. 1518, pp. 237-248.
Buhmann et al., "Immunotherapy of Recurrent B-Cell Malignancies After Allo-SCT with Bi20 (FBTA05), a Trifunctional Anti-CD3 x Anti-CD20 Antibody and Donor Lymphocyte Infusion," Bone Marrow Transplantation (2009) vol. 43, No. 5, pp. 383-397.
Carpenter et al., "B-Cell Maturation Antigen is a Promising Target for Adoptive T-Cell Therapy of Multiple Myeloma," Clin. Cancer Res. (2013) vol. 19(8), pp. 2048-2060.
Casneuf et al., "Serum Proteomic Analysis of Multiple Myeloma Subjects Treated with Daratumumab Monotherapy," Blood (2015) 126(23), 1837.
Chames et al., "Bispecific Antibodies for Cancer Therapy The Light at the end of the tunnel?" mAbs (Nov./Dec 2009) vol. 1, Issue. 6, pp. 539-547.
Chiarugi et al., "The NAD Metabolome—A Key Determinant of Cancer Cell Biology," Nature Reviews (Nov. 2012) vol. 12, pp. 741-752.
Chothia et al., "Canonical Structures for the Hypervariable Regions of Immunoglobulins," J. Mol. Biol. (1987) vol. 196, pp. 901-917.
Chothia et al., "Conformations of Immunoglobulin Hypervariable Regions," Nature (1989) vol. 342, pp. 877-883.
Cohen et al., "GPRC5D is a Promising Marker for Monitoring the Tumor Load and to Target Multiple Myeloma Cells," Hematology (Nov. 2013) vol. 18(6), pp. 347-350.
Darce et al., "Regulated Expression of Baff•Binding Receptors During Human B Cell Differentiation," J Immunol (2007) vol. 179(11), pp. 7276-7286.
Doody et al., "A Phase 3 Trial of Semagacestat for Treatment of Alzheimer's Disease," N Engl J Med (2013) vol. 369, pp. 341-350.
Dreger et al., "Allogeneic Stem Cell Transplantation Provides Durable Disease Control in Poor-Risk Chronic Lymphocytic Leukemia: Long-Term Clinical and MRD Results of the German CLL Study Group CLL3X Trial," Blood (Oct. 7, 2010) vol. 116(14), pp. 2438-2447.
Durie et al., "International Response Criteria for Multiple Myeloma," Leukemia (2006) vol. 20(9), pp. 1467-1473.

(56) References Cited

OTHER PUBLICATIONS

Ferrer et al., "B Cell Activation Through CD40 and IL4R Ligation Modulates the Response of Chronic Lymphocytic Leukaemia Cells to Baff and April," Br J Haematol. (2014) vol. 164, pp. 570-578.
Frankel et al., "Targeting T Cells to Tumor Cells Using Bispecific Antibodies," Curr Opin Chem Biol (Jun. 2013) vol. 17 (3), pp. 385-392. (Abstract Only).
Frigyesi et al., "Robust Isolation of Malignant Plasma Cells in Multiple Myeloma," Blood (Feb. 27, 2014) vol. 123(9), pp. 1336-1340.
Fritsch et al., "Suppression of Granzyme B Activity and Caspase-3 Activation in Leukaemia Cells Constitutively Expressing the Protease Inhibitor 9," Ann Hematol (2013) vol. 92, pp. 1603-1609.
Funaro et al., "Involvement of the Multilineage CD38 Molecule in a Unique Pathway of Cell Activation and Proliferation," J. Immunol. (Oct. 15, 1990) vol. 145, No. 8, pp. 2390-2396.
Goebeler et al., "Bispecific T-Cell Engager (BiTE) Antibody Construct Blinatumomab for the Treatment of Patients with Relapsed/Refractory Non-Hodgkin Lymphoma: Final Results From a Phase I Study," J. Clin. Oncol. (Apr. 1, 2016) 34 (10), pp. 1104-1011.
Guse et al., "Regulation of Calcium Signalling in T Lymphocytes by the Second Messenger Cyclic ADP-Ribose," Nature (Mar. 4, 1999) vol. 398, pp. 70-73.
Haas et al., "Mode of Cytotoxic Action of T Cell-Engaging BiTE Antibody MT110," Immunobiology (Jun. 2009) vol. 214 (6), pp. 441-453.
Hayano et al., "Proteomic Analysis of Human Nop56p-associated Pre-Ribosomal Ribonucleoprotein Complexes," J. Biol. Chem. (2003) vol. 278(36), pp. 34309-34319.
Hilchey et al., "Follicular Lymphoma Tumor-Infiltrating T-helper (T(H)) Cells have the Same Polyfunctional Potential as Normal Nodal T(H) Cells Despite Skewed Differentiation," Blood (Sep. 2011) vol. 118(13), pp. 3591-3602.
Honegger et al., "Yet Another Numbering Scheme for Immunoglobulin Variable Domains: An Automatic Modeling and Analysis Tool," J. Mol. Biol. (2001) vol. 309, pp. 657-670.
Hoogenboom et al., "By-Passing Immunisation: Human Antibodies from Synthetic Repertoires of Germline VH Gene Segments Rearranged in Vitro," J. Mol. Biol. (1992) vol. 227, p. 381-388.
Hu et al., "Small Molecule Inhibitors of Protein Arginine Methyltransferases," Expert Opin. Investig. Drugs (2016) 25(3), pp. 335-358.
Kettleborough et al., "Humanization of a Mouse Monoclonal Antibody by CDR-Grafting: the Importance of Framework Residues on Loop Conformation," Protein Engineering (1991) vol. 4, No. 7, pp. 773-783.
Knappik et al., "Fully Synthetic Human Combinatorial Antibody Libraries (HuCAL) Based on Modular Consensus Frameworks and CDRs Randomized with Trinucleotides," J. Mol. Biol. (2000) vol. 296, pp. 57-86.
Krebs et al., "High-Throughput Generation and Engineering of Recombinant Human Antibodies," J. Immunol. Meth. (Aug. 1, 2001) vol. 254, pp. 67-84.
Kridel et al., "Whole Transcriptome Sequencing Reveals Recurrent NOTCH1 Mutations in Mantle Cell Lymphoma," Blood (Mar. 2012) vol. 119(9), pp. 1963-1971.
Krop et al., "Phase I Pharmacologic and Pharmacodynamic Study of the Gamma Secretase (Notch) Inhibitor MK-0752 in Adult Patients with Advanced Solid Tumors," J Clin Oncol (Jul. 1, 2012) vol. 30(19), pp. 2307-2313.
Kumar et al., "Risk of Progression and Survival in Multiple Myeloma Relapsing After Therapy with ImiDs and Bortezombib: A Multicenter International Myeloma Working Group Study," Leukemia (2012) vol. 26, pp. 149-157.
Laurent et al., "Y-Secretase Directly Sheds the Survival Receptor BCMA from Plasma Cells," Nat. Commun. (2015) vol. 6, Art. No. 7333, pp. 1-12.
Lee et al., "Current Concepts in the Diagnosis and Management of Cytokine Release Syndrome," Blood (Jul. 10, 2014) vol. 124, No. 2, pp. 188-195.
Lee et al., "Evaluation of B Cell Maturation Antigen as a Target for Antibody Drug Conjugate Mediated Cytotoxicity in Multiple Myeloma," Br J Haematol. (2016) vol. 174, pp. 911-922.
Lefranc et al., "IMGT Unique Numbering for Immunoglobulin and T Cell Receptor Variable Domains and Ig Superfamily V-Like Domains," Dev. Comp. Immunol. (2003) vol. 27, pp. 55-77.
MacCallum et al., "Antibody-Antigen Interactions: Contact Analysis and Binding Site Topography," J. Mol. Biol. (1996) vol. 262, pp. 732-745.
Marks et al., "By-Passing Immunization," J. Mol. Biol. (1991) vol. 222, p. 581-597.
Martin et al., "Structural Families in Loops of Homologous Proteins: Automatic Classification, Modelling and Application to Antibodies," J. Mol. Biol. (1996) vol. 263, pp. 800-815.
May et al., "Advances in Bispecific Biotherapeutics for the Treatment of Cancer," Biochem. Pharmacol. (Nov. 1, 2012) vol. 84, pp. 1105-1112.
Meslin et al., "Granzyme B-Induced Cell Death Involves Induction of p53 Tumor Suppressor Gene and its Activation in Tumor Target Cells," J Biol Chem (Nov. 9, 2007) vol. 282, No. 45, pp. 32991-32999.
Messersmith et al., "A Phase I, Dose-Finding Study in Patients with Advanced Solid Malignancies of the Oral Gamma-Secretase Inhibitor PF-03084014," Clin Cancer Res (Jan. 2015) vol. 21(1), pp. 60-67.
Neuenschwander et al., "Critical Aspects of the Bayesian Approach to Phase I Cancer Trials," Statist. Med. (2008) vol. 27(13), pp. 2420-2439.
Ng et al., "B Cell-Activating Factor Belonging to the TNF family (BAFF)-R is the Principal Baff Receptor Facilitating Baff Costimulation of Circulating T and B Cells," J Immunol. (2004) vol. 173(2), pp. 807-817.
Nijhof et al., "Upregulation of CD38 Expression on Multiple Myeloma Cells by All-Trans Retinoic Acid Improves the Efficacy of Daratumumab," Leukemia (2015) 29(10), pp. 2039-2049.
Nũnez-Prado et al., "The Coming of Age of Engineered Multivalent Antibodies," Drug Discovery Today (2015) vol. 20, No. 5, pp. 588-594.
O'Connor et al., "BCMA is Essential for the Survival of Long-Lived Bone Marrow Plasma Cells," J Exp Med (2004) vol. 199(1), pp. 91-97.
Palaiologou et al., "CD138 (syndecan-1) Expression in Health and Disease," Histol. Histopathol. (2014) vol. 29(2), pp. 177-189.
Panza et al., "Gamma-Secretase Inhibitors for the Treatment of Alzheimer's Disease: The Current State," CNS Neurosci. Ther. (2010) vol. 16, pp. 272-284.
Phipps et al., "Daratumumab and Its Potential in the Treatment of Multiple Myeloma: Overview of the Preclinical and Clinical Development," Ther. Adv. Hematol. (Jun. 2015) vol. 6(3), pp. 120-127.
Portell et al., "Clinical and Pharmacologic Aspects of Blinatumomab in the Treatment of B-Cell Acute Lymphoblastic Leukemia," Clin Pharmacol. (2013) vol. 5, Suppl. 1, pp. 5-11.
Rajkumar et al., "Consensus Recommendations for the Uniform Reporting of Clinical Trials: Report of the International Myeloma Workshop Conconsenus Panel 1," Blood (2011) vol. 117(18), pp. 4691-4695.
Ramsay et al., "Follicular Lymphoma Cells Induce T-cell Immunologic Synapse Dysfunction that can be Repaired with Lenalidomide: Implications for the Tumor Microenvironment and Immunotherapy," Blood (Nov. 2009) vol. 114(21), pp. 4713-4720.
Ramsay et al., "Multiple Inhibitory Ligands Induce Impaired T-Cell Immunologic Synapse Function in Chronic Lymphocytic Leukemia that can be Blocked with Lenalidomide: Establishing a Reversible Immune Evasion Mechanism in Human Cancer," Blood (Aug. 2012) vol. 120(7), pp. 1412-1421.
Riches et al., "T Cells from CLL Patients Exhibit Features of T-Cell Exhaustion but Retain Capacity for Cytokine Production," Blood (Feb. 2013) vol. 121(9), pp. 1612-1621.
Rudikoff et al., "Single Amino Acid Substitution Altering Antigen-Binding Specificity," Proc. Natl. Acad. Sci. USA (Mar. 1, 1982) vol. 79, No. 6, pp. 1979-1983.

(56) References Cited

OTHER PUBLICATIONS

Sanchez et al., "Daratumumab: A First-In-Class CD38 Monoclonal Antibody for the Treatment of Multiple Myeloma," Journal of Hematology & Oncology (2016) 9(51), 8 pgs.
Sanchez et al., "Serum B-Cell Maturation Antigen is Elevated in Multiple Myeloma and Correlates with Disease Status and Survival," British Journal of Hematology (Jul. 18, 2012) vol. 158, No. 158, pp. 727-738.
Sela-Culang et al., "The Structural Basis of Antibody-Antigen Recognition," Frontiers in Immunology (Oct. 8, 2013) vol. 4, Art. 302, 13 pgs.
Sheets et al., "Efficient Construction of a Large Nonimmune Phage Antibody Library: The Production of High-Affinity Human Single-Chain Antibodies to Protein Antigens," Proc. Natl. Acad. Sci. USA (May 1998) vol. 95, pp. 6157-6162.
Shi et al., "De Novo Selection of High-Affinity Antibodies from Synthetic Fab Libraries Displayed on Phage as pIX Fusion Proteins," J. Mol. Biol. (2010) vol. 397, pp. 385-396.
Smith et al., "Lymphoma Incidence, Survival and Prevalence 2004-2014: Sub-Type Analyses from the UK's Haematological Malignancy Research Network," British Journal of Cancer (2015) vol. 112, pp. 1575-1584.
Stickler et al., "The Human G1m1 Allotype Associates with CD4+ T-Cell Responsiveness to a Highly Conserved IgG1 Constant Region Peptide and Confers an Asparaginyl Endopeptidase Cleavage Site," Genes and Immunity (2011) vol. 12, pp. 213-221.
Tai et al., "April and BCMA Promote Human Multiple Myeloma Growth and Immunosuppression in the Bone Marrow Microenvironment," Blood (Jun. 2016) vol. 127, pp. 3225-3236.
Tai et al., "Targeting B-Cell Maturation Antigen in Multiple Myeloma," Immunotherapy (Nov. 2015) vol. 7(11), pp. 1187-1199.
Terhorst et al., "Biochemical Studies of the Human Thymocyte Cell-Surface Antigens T6, T9 and T10," Cell (Mar. 1981) vol. 23, No. 3, pp. 771-780.
Thompson et al., "Baff Binds to the Tumor Necrosis Factor Receptor-Like Molecule B Cell Maturation Antigen and is Important for Maintaining the Peripheral B cell Population," J Exp Med (2000) vol. 192(1), pp. 129-135.
Tolcher et al., "Phase I Study of RO4929097, a Gamma Secretase Inhibitor of Notch Signaling, in Patients with Refractory Metastatic or Locally Advanced Solid Tumors," J Clin Oncol (Jul. 1, 2012) vol. 30(19), pp. 2348-2353.
Tonino et al., "Expansion of Effector T Cells Associated with Decreased PD-1 Expression in Patients with Indolent B Cell Lymphomas and Chronic Lymphocytic Leukemia," Leuk. Lymphoma (2012) vol. 53(9), pp. 1785-1794.
Topp et al., "Long-Term Follow-Up of Hematologic Relapse-Free Survival in a Phase 2 Study of Blinatumomab in Patients with MRD in B-Lineage ALL," Blood (Dec 20, 2012) vol. 120(26), pp. 5185-5187.
Topp et al., "Phase 1 Dose-Escalation Study of BI 836909, an Anti-BCMA Bispecific T-Cell Engager, in Relapsed and/or Refractory Multiple Myeloma (RRMM)," Meeting Abstract: 2016 ASCO Annual Meeting, J. Clin. Oncol., vol. 34, No. 15 Suppl. 2 pgs.
Topp et al., "Safety and Activity of Blinatumomab for Adult Patients with Relapsed or Refractory B-Precursor Acute Lymphoblastic Leukaemia: a Multicentre, Single-Arm, Phase 2 Study," Lancet Oncol. (Jan. 2015) vol. 16, pp. 57-66.
Usmani et al., "Analysis of Real-World Data on Overall Survival in Multiple Myeloma Patients with 3 Prior Lines of Therapy Including a Proteasome Inhibitor (PI) and an Immunomodulatory Drug (IMiD), or Double Refractory to a PI and an IMID," The Oncologist (2016) vol. 21, pp. 1355-1361.
Van der Veer et al., "The Therapeutic Human CD38 Antibody Daratumumab Improves the Anti-Myeloma Effect of Newly Emerging Multi-Drug Therapies," Blood Cancer J. (2011) 1(10): e41.
Van der Veer et al., "Towards Effective Immunotherapy of Myeloma: Enhanced Elimination of Myeloma Cells by Combination of Lenalidomide with the Human CD38 Monoclonal Antibody Daratumumab," Haematologica (2011) 96 (2), pp. 284-290.
Vaughan et al., "Human Antibodies with Sub-Nanomolar Affinities Isolated from a Large Non-Immunized Phage Display Library," Nature Biotechnology (Mar. 1996) vol. 14, pp. 309-314.
Wang et al., "Antibody Structure, Instability, and Formulation," Journal of Pharmaceutical Sciences (Jan. 1, 2007) vol. 96, No. 1, pp. 1-26.
Winkler et al., "Changing the Antigen Binding Specificity by Single Point Mutations of an Anti-p24 (HIV-1) Antibody," The Journal of Immunology (Oct. 15, 2000) vol. 165, No. 8, pp. 4505-4514.
Wu et al., "An Analysis of the Sequences of the Variable Regions on Bence Jones Proteins and Myeloma Light Chains and Their Implications for Anti-Body Complementarity," J. Exp. Med. (1970) 132, pp. 211-250.
GenBank: BC069341.1, Homo Sapiens G Protein-Coupled Receptor, Family C, Group 5, Member D, mRNA (cDNA clone MGC:97012 Image: 7262221), complete cds (Aug. 19, 2004) 2 pgs.
Coquery et al., "Regulatory Roles of the Tumor Necrosis Factor Receptor BCMA," Crit. Rev. Immunol. (2012) vol. 32, No. 4, pp. 287-305.
Marriuzza, et al. The structural basis of antigen-antibody recognition, Ann. Rev. Biophys. Chem. 16, 139-59, (1987).*
Beiboer et al. Guided Selection of a Pan Carcinoma Specific Antibody Reveals Similar Binding Characteristics yet Structural Divergence Between the Original Murine Antibody and its Human Equivalent, J. Mol. Biol. 296:833-849,2000.*
Pascalis et al., Grafting of "abbreviated" complementarity-determining regions containing specificity-determining residues essential for ligand contact to engineer a less immunogenic humanized monoclonal antibody, Journal of Immunology 169: 3076-3084, 2002.*
Casset et al., A peptide mimetic of an anti-CD4 monoclonal antibody by rational design, BBRC 307, 198-205, 2003.*
Padlan et al., Structure of an antibody-antigen complex: crystal structure of the HyHEL-10 Fab-lysozyme complex, PNAS 86:5938-594, 1989.*
Abhinandan, et al., Analysis and Improvements to Kabat and Structurally Correct Numbering of Antibody Variable Domains, Molelcular Immunology, 2008, pp. 3832-3839, vol. 45.
Adams, et al,. Recent developments in the PHENIX software for automated crystallographic structure determination, J Synchrotron Radiat, Oct. 15, 2003, pp. 53-55, vol. 11.
Anasetti et al., Treatment of Acute Graft-Versus-Host Diseases With a Nonmitogenic Ant-CD3 Monoclonal Antibody, Transplantation, 1992, pp. 844-851, vol. 54 Issue 5.
Chames, et al., Bispecific Antibodies for Cancer Therapy, Current Opinion in Drug Discovery & Development, 2009, pp. 276-283, vol. 12, No. 2.
Cline, Perspecitives for Gene Therapy: Inserting New Genetic Information into Mammalian Cells by Physical Techniques and Viral Vectors, Pharmac. Ther., 1985, pp. 69 to 92, vol. 29.
DeLano., PyMOL: An Open source Molecular Graphics Tool, DeLano Scientific, 2002, pp. 1-9, page number.
Emsley_et_al, Coot: model-building tools for molecular graphics., Acta Crystallogr D Biol Crystallogr, 2004, 2126-32, 60(Pt 12 Pt 1).
Ferrara, et al., Modulation of Therapeutic Antibody Effector Functions by Glycosylation Engineering: Influence of Golgi Enzyme Localization Domain andCo-Expression of Heterologous b1 , 4-N-acetylglucosaminyltransferase III and Golgi a-mannosidase II, Biotechnology and Bioengineering, Apr. 5, 2006, pp. 851-861, vol. 93 Issue 5.
Ferrara, et al., The Carbohydrate at FcyRllla Asn-162 An Dement Required for High Affinity Binding to Non-Fucosylated IgG Glycoforms, The Journal of Biological Chemistry, Feb. 24, 2006, pp. 5032-5036, vol. 281 No. 8.
Gadi, et al., In Vivo Sensitization of Ovarian Tumors to Chemotherapy by Expression of *E. coli* Purine Nucleoside Phosphorylase in a Small Fraction of Cells, Gene Therapy, 2000, pp. 1738-1743, vol. 7.
Gras, et al., BCMAp: an integral membrane protein in the Golgi apparatus of human mature B lymphocytes, International Immunology, Mar. 28, 1995, pp. 1093-1106, vol. 7 Issue 7.

(56) References Cited

OTHER PUBLICATIONS

Hollger, et al., "Diabodies": Small Bivalent and Bispecific Antibody Fragments, Proc. Natl. Acad. Sci. USA, 1993, pp. 6444-6448, vol. 90.
Holt, et al., Domain Antibodies: Protelns for Therapy, TRENDS in Biotechnology, 2003, pp. 484-490, vol. 21, No. 11.
Konno, et al., Fucose Content of Monoclonal Antibodies can be Controlled by Culture Medium Osmolality for High Antibody-Dependent Cellular Cytotoxicity, Cytotechnology, 2012, pp. 249-265, vol. 64.
Mori, et al., Engineering Chinese Hamster Ovary Cells to Maximze Effector Function of Produced Antibodies Using FUT8 siRNA, Biotechnology and Bioengineering, 2004, pp. 901-908, vol. 88, No. 7.
Myers, et al., Optimal Alignments in Linear Space, Cabios., 1988, pp. 11-17, vol. 4, No. 1.
Needleman, et al., A General Method Applicable to the Search for Similarities in the Amino Acid Sequence of Two Proteins, J. Mol. Biol, 1970, pp. 443-453, vol. 48.
Okayama, et al., A cDNA Cloning Vector That Permits Expression of cDNA Inserts in Mammalian Cells, Molecular and Cellular Biology, Feb. 1983, pp. 280-289, vol. 3, No. 2.
Olivier et al., EB66 Cell Line, A Duck Embryonic Stem Cell-Derived Substrate for the Industrial Production of Therapeutic Monoclonal Antibodies with Enhance ADCC Activity, mAbs, 2010, pp. 405-415, vol. 2, No. 4.
Osborn, et al., High-Affinity IgG Antibodies Develop Naturally in Ig-Knockout Rats Carrying Germline Human IgH/Igk/Igf Loci Bearing the Rat CH Region, The Journal of Immunology, Jan. 9, 2013, pp. 1481-1490, vol. 190.
Otwinowski, et al., [20] Processing of X-Ray Diffraction Data Collected in Oscillation Mode, Methods in Enzymology, 1997, pp. 307-326, vol. 276.
Randy J. Read, Pushing the boundaries of molecular replacement with maximum likelihood, Acta Crystallographica Section D, Jul. 18, 2001, pp. 1373-1382, vol. D57.
Revets, et al., Nanobodies as novel agents for cancer therapy, Expert Opin. Biol. Ther, Apr. 20, 2005, pp. 111-124, vol. 5 Issue 1.
Salmeron, et al., A Conformational epitope expressed upon association of CD3-epsilon with either CD3-delta or CD3-gamma is the main target for recognition by anti-CD3 monoclonal antibodies., The Journal of Immunology, Nov. 1, 1991, pp. 3047-3052, vol. 147 Issue 9.
Shields, et al., Lack of Fucose an Human IgG1 N-Linked Oligosaccharide Improves Binding to Human FcyRIll and Antibody-Dependent Cellular Toxicity, The Journal of Biological Chemistry, 2002, pp. 26733-26740, vol. 227, No. 30.
Shinkawa, et al., The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity, The Journal of Biological Chemistry, Nov. 8, 2002, pp. 3466-3473, vol. 278 Issue 5.
Ward, et al., Binding Activities of a Repertoire of Single Immunoglobulin Variable Domains Secreted from *Escherichia coli*, Nature, 1989, pp. 544-546, vol. 341.
XP002762973, Anti-CD3 Epsilon Humanized Antibody VL Region Coding Gene, Seq ID 55, Database Geneseq [online], Jan. 17, 2013, Database Accession No. BAG88459.
XP002762974, Anti-HA mAb (CL860UCA) Light Chain Variable Region Coding Gene, Seg 5, Database Geneseq [Online], Apr. 11, 2013, Database Accession No. BAK30778.
XP002762975, Anti-CD3 Variant Humanized Antibody VH (XENP11810 H1.15_L1.4), Seq 57, Database Geneseq [Online], Dec. 4, 2014, Database Accession No. BBP23340.
Yang, et al., A Common Pathway for T Lymphocyte Activation Involving Both the CD3-Ti Complex and CD2 Sheep Erythrocyte Receptor Determinants', The Journal of Immunology, Aug. 15, 1986, pp. 1097-1100, vol. 137 Issue 4.
Zhou, et al., Development of A Simple and Rapid Method for Producing Non-Fucosytated Oligomannose Containing Antibodies With Increased Effector Function, Biotechnology and Bioengineering, 2008, pp. 652-665, vol. 99, No. 3.

* cited by examiner

FIG. 3

Epitope

```
                1                                                   54
Human BCMA      MLQMAGQCSQNEYFDSLLHACIPCQLRCSSNTPPLTCQRYCNASVTNSVKGTNA   (1-54 of SEQ ID NO: 1)
Cyno  BCMA      MLQMARQCSQNEYFDSLLHDCKPCQLRCSS-TPPLTCQRYCNASMTNSVKGMNA   (1-53 of SEQ ID NO: 3)
Mouse BCMA      ---MAQQCFHSEYFDSLLHACKPCHLRCSN--PPATCQPYCDPSVTSSVKGTYT   (1-49 of SEQ ID NO: 2)
```

Paratope

SEQ ID NO: 75

```
                1                                CDR-H1                    CDR-H2                77
BCMB69_HC       QLQLQESGPGLVKPSETLSLTCTVSGGSISSGGSYEWGWIRQPPGKGLEWIGSIYYSGITYYNPSLKSRVTISVDTSK
                78                       CDR-H3                                                154
BCMB69_HC       NQFSLKLSSVTAADTAVYYCARHDGAVAGLFDYWGQGTLVTVSSASTKGPSVFPLAPSSKSTSGGTAALGCLVKDY
                155                                                                            231
BCMB69_HC       FPEPVTVSWNSGALTSGVHTFPAVLQSSGLYSLSSVVTVPSSSLGTQTYICNVNHKPSNTKVDKKVEPKSCHHHHHH
```

SEQ ID NO: 76

```
                1                          CDR-L1                    CDR-L2                72
BCMB69_LC       SYVLTQPPSVSVAPGQTARITCGGNNIGSKSVHWYQQPPGQAPVVVVYDDSDRPSGIPERFSGSNSGNTATL
                73                 CDR-L3                                                144
BCMB69_LC       TISRVEAGDEAVYYCQVWDSSSDHVVFGGGTKLTVLGQPKAAPSVTLFPPSSEELQANKATLVCLISDFYPG
                145                                                                    214
BCMB69_LC       AVTVAWKGDSSPVKAGVETTTPSKQSNNKYAASSYLSLTPEQWKSHRSYSCQVTHEGSTVEKTVAPTECS
```

FIG. 5

| mAb | Fc-BCMA | First Complex ($K_{D1}$, nM) | Final Complex ($K_D$, nM) | RANGE |
|---|---|---|---|---|
| BCMB72 | Human | 1.59 | 0.18 | 0.15 – 0.20 |
| | Cyno | 17.8 | 6.50 | 5.36 – 7.27 |
| | Mouse | 283 | 72.4 | 62.0 – 82.9 |

BCMB72 affinities: Human> Cyno>> Mouse

| Cells: | EC50 (nM): |
|---|---|
| H929 | 14.7 |
| MM.1R | 8.74 |
| EJM | 17.5 |
| LP1 | 22.3 |
| U2932 | 7.92 |

FIG. 8A
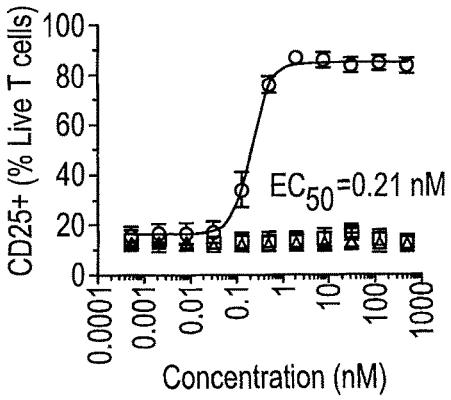
FIG. 8B
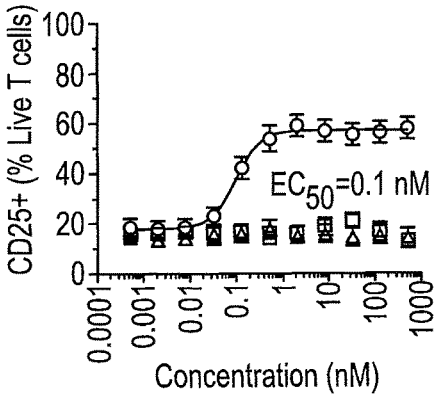
FIG. 8C
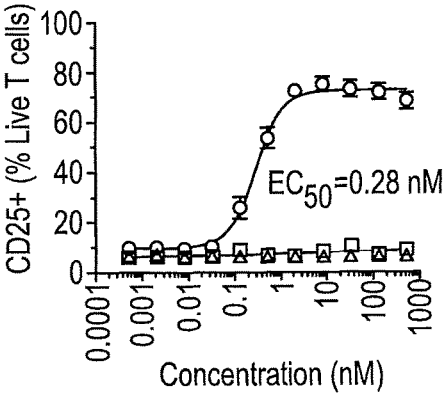
FIG. 8D
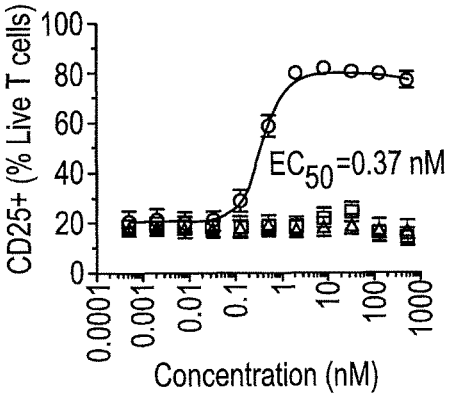
FIG. 8E
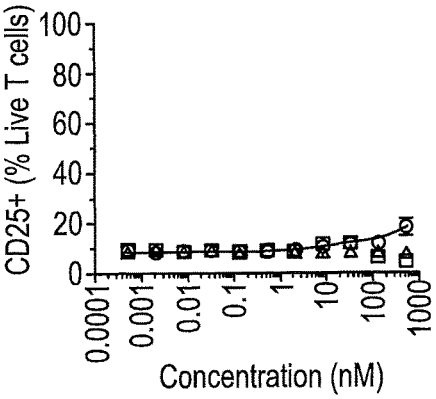
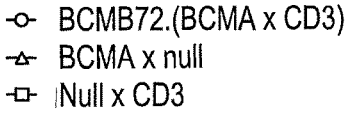

FIG. 9A

| Cell line | H929 (BCMA-00271) | | H929 (BCMA-00273) | |
|---|---|---|---|---|
| Donor | EC50 (nM) | % Max activation | EC50 (nM) | % Max activation |
| M5137 | 0.1683 | 89.74 | ~ 0.5477 | 68.70 |
| M7197 | 0.3000 | 80.73 | 1.0860 | 81.11 |
| M6576 | 0.3178 | 85.08 | 0.5134 | 82.66 |
| M6457 | 0.2436 | 74.57 | 0.7859 | 81.07 |
| M2550 | 0.1572 | 92.34 | 0.4325 | 85.24 |
| M6521 | 0.1313 | 85.01 | no data | no data |
| M7077 | no data | no data | 1.3240 | 72.96 |
| **Average** | **0.2116** | **84.64** | **0.7070** | **78.53** |
| | | | | |
| Cell line | MM.1R (BCMA-00271) | | MM.1R (BCMA-00273) | |
| Donor | EC50 (nM) | % Max activation | EC50 (nM) | % Max activation |
| M5137 | 0.0968 | 64.71 | 0.1296 | 79.62 |
| M7197 | 0.1159 | 45.60 | 0.1323 | 70.25 |
| M6576 | 0.1179 | 50.93 | 0.1646 | 78.08 |
| M6457 | 0.0776 | 49.27 | 0.1042 | 80.51 |
| M2550 | 0.1206 | 60.05 | 0.3514 | 83.80 |
| M6521 | 0.0964 | 73.62 | no data | no data |
| M7077 | no data | no data | 0.2470 | 66.68 |
| **Average** | **0.0992** | **57.12** | **0.1675** | **76.25** |
| | | | | |
| Cell line | RPMI 8226 (BCMA-00271) | | RPMI 8226 (BCMA-00273) | |
| Donor | EC50 (nM) | % Max activation | EC50 (nM) | % Max activation |
| M5137 | 0.2448 | 71.81 | 0.4787 | 50.33 |
| M7197 | 0.2260 | 67.98 | 0.3357 | 64.15 |
| M6576 | 0.2482 | 77.69 | 0.3094 | 70.58 |
| M6457 | 0.3041 | 66.83 | 0.4631 | 57.15 |
| M2550 | 0.6072 | 84.07 | 0.5163 | 70.42 |
| M6521 | 0.1409 | 67.74 | no data | no data |
| M7077 | no data | no data | 0.4055 | 54.73 |
| **Average** | **0.2777** | **72.76** | **0.4024** | **61.19** |

FIG. 9B

| Cell line | U266 (BCMA-00271) | | U266 (BCMA-00273) | |
|---|---|---|---|---|
| Donor | EC50 (nM) | % Max activation | EC50 (nM) | % Max activation |
| M5137 | 0.2068 | 85.39 | 0.4073 | 73.02 |
| M7197 | 0.3833 | 71.98 | 0.5545 | 65.98 |
| M6576 | 0.4521 | 80.52 | 0.6042 | 76.95 |
| M6457 | 0.3646 | 74.82 | 0.4772 | 61.85 |
| M2550 | 0.5256 | 85.30 | 0.6823 | 76.24 |
| M6521 | 0.4068 | 84.71 | no data | no data |
| M7077 | no data | no data | 0.6629 | 68.31 |
| **Average** | **0.3743** | **80.41** | **0.5711** | **70.34** |
| | | | | |
| Cell line | MV4-11 (BCMA-00271) | | MV4-11 (BCMA-00273) | |
| Donor | EC50 (nM) | % Max activation | EC50 (nM) | % Max activation |
| M5137 | ~ 2.940e+006 | ~ 1522 | ~ 1.357 | 4.702 |
| M7197 | 6.214 | 7.572 | 144 | 6.156 |
| M6576 | ~ 1.855e+010 | ~ 104868 | 31.41 | 10.7 |
| M6457 | ~ 2.294e+007 | ~ 4196 | no fit | no fit |
| M2550 | ~ 4.075e+008 | ~ 68789 | 16.85 | 5.626 |
| M6521 | ~ 59722 | ~ 110.5 | no data | no data |
| M7077 | no data | no data | 279 | 8.427 |
| **Average** | **1.531E+12** | **229246** | **30.58** | **6.958** |

FIG. 11A

| Cell line | H929 (BCMA-00271) | | H929 (BCMA-00273) | |
|---|---|---|---|---|
| Donor | EC50 (nM) | % Max lysis | EC50 (nM) | % Max lysis |
| M5137 | 0.2376 | 90.48 | 1.1630 | 75.61 |
| M7197 | 0.1631 | 92.02 | 1.3480 | 82.56 |
| M6576 | ~ 0.1405 | 91.75 | 0.4301 | 87.14 |
| M6457 | 0.2294 | 79.98 | 0.8720 | 82.29 |
| M2550 | ~ 0.1130 | 92.48 | 0.3575 | 89.63 |
| M6521 | 0.0973 | 92.27 | no data | no data |
| M7077 | no data | no data | 1.7690 | 80.05 |
| **Average** | **0.1495** | **89.72** | **0.8133** | **83.13** |
| | | | | |
| Cell line | MM.1R (BCMA-00271) | | MM.1R (BCMA-00273) | |
| Donor | EC50 (nM) | % Max lysis | EC50 (nM) | % Max lysis |
| M5137 | 0.0654 | 92.97 | 0.0569 | 97.23 |
| M7197 | 0.0824 | 92.60 | 0.0945 | 96.75 |
| M6576 | 0.0480 | 90.47 | 0.0617 | 95.29 |
| M6457 | 0.0548 | 81.00 | 0.0432 | 87.92 |
| M2550 | 0.0595 | 92.95 | 0.1212 | 96.97 |
| M6521 | 0.0511 | 87.76 | no data | no data |
| M7077 | no data | no data | 0.1008 | 94.98 |
| **Average** | **0.0617** | **89.62** | **0.0766** | **94.87** |
| | | | | |
| Cell line | RPMI 8226 (BCMA-00271) | | RPMI 8226 (BCMA-00273) | |
| Donor | EC50 (nM) | % Max lysis | EC50 (nM) | % Max lysis |
| M5137 | 0.5044 | 82.02 | 1.0670 | 81.12 |
| M7197 | 0.7262 | 82.47 | 0.8636 | 78.55 |
| M6576 | 0.3366 | 86.65 | 0.4842 | 79.81 |
| M6457 | 0.6967 | 76.10 | 1.0700 | 69.25 |
| M2550 | 0.5379 | 89.73 | 0.6956 | 84.73 |
| M6521 | 0.1625 | 81.03 | no data | no data |
| M7077 | no data | no data | 1.2050 | 73.50 |
| **Average** | **0.4531** | **83.55** | **0.8543** | **77.99** |

FIG. 11B

| Cell line | U266 (BCMA-00271) | | U266 (BCMA-00273) | |
|---|---|---|---|---|
| Donor | EC50 (nM) | % Max lysis | EC50 (nM) | % Max lysis |
| M5137 | 0.7610 | 72.59 | 1.0180 | 76.19 |
| M7197 | 0.7355 | 76.36 | 1.1610 | 77.29 |
| M6576 | 0.7298 | 83.86 | 0.9710 | 82.34 |
| M6457 | 0.7734 | 62.05 | 1.4320 | 56.77 |
| M2550 | 0.6516 | 83.21 | 0.9347 | 85.93 |
| M6521 | 0.5621 | 83.09 | no data | no data |
| M7077 | no data | no data | 1.1580 | 74.21 |
| **Average** | **0.7046** | **76.82** | **1.0800** | **75.31** |
| | | | | |
| Cell line | MV4-11 (BCMA-00271) | | MV4-11 (BCMA-00273) | |
| Donor | EC50 (nM) | % Max lysis | EC50 (nM) | % Max lysis |
| M5137 | 2.038 | 8.425 | ~ 0.06555 | 18.31 |
| M7197 | ~ 157.1 | 4.79 | no fit | no fit |
| M6576 | ~ 391461 | ~ 23049 | 18.61 | 9.836 |
| M6457 | no fit | no fit | 0 | -9780 |
| M2550 | ~ 147.7 | 8.21 | ~ 14.70 | 8.366 |
| M6521 | no fit | no fit | no data | no data |
| M7077 | no data | no data | ~ 1.247e+022 | 18.68 |
| **Average** | **~ 157.2** | **7.658** | **no fit** | **no fit** |

T cell mediated cytotoxicity assay
H929 cells (48hrs); Donor ID: M 5763 & 6576

T cell activation assay
H929 cells (48hrs); Donor ID: M 5763 & 6576

FIG. 13

| BCMAxCD3 $EC_{50}$ Analysis (nM) | | | | | | |
|---|---|---|---|---|---|---|
| | | | | | | |
| | M2550 | M5137 | M6457 | M6541 | M6576 | M7197 |
| IFNg | 2.049 | ~ 2.079 | ~ 2.112 | ~ 0.9252 | 1.366 | 1.126 |
| TNFa | 2.909 | 2.377 | 3.717 | 2.863 | 1.991 | 95.15 |
| IL-2 | 3.262 | 1.645 | 2.508 | 1.297 | 1.501 | 1.767 |
| IL-6 | 2.385 | ~ 2.054 | 1.65 | ~ 0.5650 | 0.7961 | ~ 0.5003 |
| IL-8 | 1.031 | 0.3267 | 0.7208 | ~ 0.1117 | 0.328 | ~ 0.4640 |
| IL-10 | 1.158 | ~ 0.7865 | 0.7296 | ~ 0.5154 | ~ 0.5217 | 0.9593 |

MM277BM

ANTI-BCMA ANTIBODIES AND USES THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application claims the benefit of U.S. Provisional Patent Application Ser. No. 62/206,246, filed Aug. 17, 2015, which is hereby incorporated by reference in its entirety.

*More than one reissue application has been filed for the reissue of U.S. Pat. No. 10,072,088. The reissue applications are U.S. patent application Ser. No. 17/739,055, filed May 6, 2022 (the present application) and U.S. patent application Ser. No. 19/553,068, filed Feb. 27, 2026, which is a continuation reissue application of the present application.*

[SEQUENCE LISTING]

[The instant application contains a Sequence Listing which has been submitted electronically in ASCII format and is hereby incorporated by reference in its entirety. Said ASCII copy, created on Aug. 15, 2016, is named PRD3383USNP_SL.txt and is 87,341 bytes in size.]

*STATEMENT REGARDING SEQUENCE LISTING*

*A Sequence Listing associated with this application is provided in text format in lieu of a paper copy and is hereby incorporated by reference into the specification. The name of the text file containing the Sequence Listing is JOJO-001-401 Sequence Listing.txt. The text file is 86KB, was created on May 6, 2022, and is being submitted electronically via EFS-Web.*

TECHNICAL FIELD

The disclosure provided herein relates to monoclonal antibodies that immunospecifically bind B-cell maturation antigen (BCMA), multispecific antibodies that immunospecifically bind BCMA and cluster determinant 3 (CD3), and methods of producing and using the described antibodies.

BACKGROUND

B-cell maturation antigen, also known as BCMA, CD269, TNFRSF17 (UniProt Q02223), is a member of the tumor necrosis receptor superfamily that is preferentially expressed in differentiated plasma cells [Laabi et al. (1992) EMBO J 11(11):3897-3904; Madry et al. (1998) Int Immunol 10(11):1693-1702]. BCMA is a non-glycosylated type I transmembrane protein, which is involved in B cell maturation, growth and survival. BCMA is a receptor for two ligands of the TNF superfamily: APRIL (a proliferation-inducing ligand, CD256, TNFSF13), the high-affinity ligand to BCMA and the B cell activation factor BAFF (THANK, BlyS, B lymphocyte stimulator, TALL-1 and zTNF4), the low-affinity ligand to BCMA. APRIL and BAFF show structural similarity and overlapping yet distinct receptor binding specificity. The negative regulator TACI also binds to both BAFF and APRIL. The coordinate binding of APRIL and BAFF to BCMA and/or TACI activates transcription factor NF-κB and increases the expression of pro-survival Bcl-2 family members (e.g. Bcl-2, Bcl-xL, Bcl-w, Mcl-1, A1) and down regulates expression of pro-apoptotic factors (e.g. Bid, Bad, Bik, Bim, etc.), thus inhibiting apoptosis and promoting survival. This combined action promotes B cell differentiation, proliferation, survival and antibody production (as reviewed in Rickert R C et al., Immunol Rev (2011) 244 (1): 115-133). In line with this finding, BCMA also supports growth and survival of malignant human B cells, including multiple myeloma (MM) cells Novak et al found that MM cell lines and freshly isolated MM cells express BCMA and TACI protein on their cell surfaces and have variable expression of BAFF-R protein on their cell surface (Novak et al., (2004) Blood 103(2):689-694).

Multiple myeloma (MM) is the second most common hematological malignancy and constitutes 2% of all cancer deaths. MM is a heterogeneous disease and caused by mostly by chromosome translocations inter alia t(11;14),t(4;14),t(8;14),del(13),del(17) (Drach et al., (1998) Blood 92(3):802-809, Gertz et al., (2005) Blood 106(8).2837-2840; Facon et al., (2001) Blood 97(6): 1566-1571). MM-affected patients may experience a variety of disease-related symptoms due to, bone marrow infiltration, bone destruction, renal failure, immunodeficiency, and the psychosocial burden of a cancer diagnosis. As of 2006, the 5-year relative survival rate for MM was approximately 34% highlighting that MM is a difficult-to-treat disease where there are currently no curative options.

The use of anti-BCMA antibodies for the treatment of lymphomas and multiple myeloma are mentioned in WO2002066516 and WO2010104949. Antibodies against BCMA are described e.g. in Gras M-P. et al. Int Immunol. 7 (1995) 1093-1106, WO200124811, and WO200124812. Nevertheless, despite the fact that BCMA, BAFF-R and TACI, i.e., B cell receptors belonging to the TNF receptor superfamily, and their ligands BAFF and APRIL are subject to therapies in fighting against cancer, there is still a need for having available further options for the treatment of such medical conditions.

SUMMARY

Provided herein are antibodies that immunospecifically bind to BCMA and antigen-binding fragments thereof. Also described are related polynucleotides capable of encoding the provided BCMA-specific antibodies and antigen-binding fragments, cells expressing the provided antibodies and antigen-binding fragments, as well as associated vectors and detectably labeled antibodies and antigen-binding fragments. In addition, methods of using the provided antibodies and antigen-binding fragments are described. For example, the BCMA-specific antibodies and antigen-binding fragments may be used to diagnose or monitor BCMA-expressing cancer progression, regression, or stability; to determine whether or not a patient should be treated for cancer; or to determine whether or not a subject is afflicted with BCMA-expressing cancer and thus may be amenable to treatment with a BCMA-specific anti-cancer therapeutic, such as the multispecific antibodies against BCMA and CD3 described herein.

Further provided herein are multispecific antibodies that immunospecifically bind to BCMA and CD3 and multispecific antigen-binding fragments thereof. Also described are related polynucleotides capable of encoding the provided BCMA×CD3-multispecific antibodies, cells expressing the provided antibodies, as well as associated vectors and detectably labeled multispecific antibodies. In addition, methods of using the provided multispecific antibodies are described. For example, the BCMA×CD3-multispecific antibodies may be used to diagnose or monitor BCMA-expressing cancer progression, regression, or stability, to determine whether or not a patient should be treated for cancer; or to determine whether or not a subject is afflicted with BCMA-expressing cancer and thus may be amenable to treatment with a BCMA-specific anti-cancer therapeutic, such as the BCMA×CD3-multispecific antibodies described herein.

BCMA-Specific Antibodies

Described herein are recombinant antibodies and antigen-binding fragments specific for BCMA. In some embodiments, the BCMA-specific antibodies and antigen-binding fragments bind human BCMA. In some embodiments, the BCMA-specific antibodies and antigen-binding fragments bind human BCMA and cynomolgus monkey BCMA. In some embodiments, the BCMA-specific antibodies and antigen-binding fragments bind to an epitope including one or more residues from the BCMA extracellular domain (ECD). This BCMA-specific antibody or antigen-binding fragment may block APRIL-binding with an $IC_{50}$ of at least 5.9 nM as measured by ELISA.

Table 1 provides a summary of examples of some BCMA-specific antibodies described herein:

TABLE 1

CDR sequences of mAbs generated against human BCMA
(SEQ ID NOs for each listed sequence are provided in parenthesis)

| ID | HC-CDR1 | HC-CDR2 | HC-CDR3 | LC-CDR1 | LC-CDR2 | LC-CDR3 |
|---|---|---|---|---|---|---|
| BCMB69 | SGSYFWG (4) | SIYYSGITYYNPSLKS (5) | **HDG**AVAGLFDY (6) | GGNNIGSKSVH (24) | DDSDRPS (25) | QVWDSSSDHVV (26) |
| BCMB117 | SGSYFWG (4) | SIYYSGITYYNPSLKS (5) | **HDG**AVAGLFDY (6) | GGNNIGSKSVH (24) | DDSDRPS (25) | QVWDSSSDHVV (26) |
| BCMB123 | SSSYYWG (7) | SIYYSGITYYNPSLKS (5) | **HDG**AVAGLFDY (6) | GGNNIGSKSVH (24) | DDSDRPS (25) | QVWDSSSDHVV (26) |
| BCMB128 | SGSYFWG (4) | SIYYSGITYYNPSLKS (5) | HDGATAGLFDY (19) | GGNNIGSKSVH (24) | DDSDRPS (25) | QVWDSSSDHVV (26) |
| BCMB129 | SGSYFWG (4) | SIYYSGSTYYNPSLKS (8) | **HDG**AVAGLFDY (6) | GGNNIGSKSVH (24) | DDSDRPS (25) | QVWDSSSDHVV (26) |
| BCMB176 | SSSYFWG (13) | SIYYSGITYYNPSLKS (5) | HDGATAGLFDY (19) | GGNNIGSKSVH (24) | DDSDRPS (25) | QVWDSSSDHVV (26) |
| BCMB177 | SSSYFWG (13) | SIYYSGSTYYNPSLKS (8) | HDGATAGLFDY (19) | GGNNIGSKSVH (24) | DDSDRPS (25) | QVWDSSSDHVV (26) |

In some embodiments are provided a BCMA-specific antibody, or an antigen-binding fragment thereof, comprising a heavy chain comprising a CDR1, a CDR2, and a CDR3 of any one of the antibodies described in Table 1. In some embodiments are provided a BCMA-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcgRs) on the surface of immune effector cells such as natural killers and macrophages, leading to the phagocytosis or lysis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcgRs or the complement factors. The binding of IgG to the activating (FcgRI, FcgRIIa, FcgRIIIa and FcgRIIIb) and inhibitory (FcgRIIb) FcgRs or the first component of complement (C1q) depends on residues located in the hinge region and the CH2 domain. Mutations have been introduced in IgG1, IgG2 and IgG4 to reduce or silence Fc functionalities. The antibodies described herein may include these modifications.

In one embodiment, the antibody comprises an Fc region with one or more of the following properties: (a) reduced effector function when compared to the parent Fc; (b) reduced affinity to Fcg RI, Fcg RIIa, Fcg RIIb, Fcg RIIIb and/or Fcg RIIIa, (c) reduced affinity to FcgRI (d) reduced affinity to FcgRIIa (e) reduced affinity to FcgRIIb, (f) reduced affinity to Fcg RIIIb or (g) reduced affinity to FcgRIIIa.

In some embodiments, the antibodies or antigen-binding fragments are IgG, or derivatives thereof, e.g., IgG1, IgG2, IgG3, and IgG4 isotypes. In some embodiments wherein the antibody has an IgG4 isotype, the antibody contains K409R, S228P, L234A, and L235A substitutions in its Fc region. The antibodies described herein may include these modifications.

In some embodiments the described antibodies are capable of inhibiting APRIL binding with a $IC_{50}$ of 5.9 nM as measured by ELISA.

In some embodiments the described antibodies bind to BCMA-positive multiple myeloma cell lines.

In addition to the described BCMA-specific antibodies and antigen-binding fragments, also provided are polynucleotide sequences capable of encoding the described antibodies and antigen-binding fragments. Vectors comprising the described polynucleotides are also provided, as are cells expressing the BCMA-specific antibodies or antigen-binding fragments provided herein. Also described are cells capable of expressing the disclosed vectors. These cells may be mammalian cells (such as 293F cells, CHO cells), insect cells (such as Sf7 cells), yeast cells, plant cells, or bacteria cells (such as E. coli). The described antibodies may also be produced by hybridoma cells.

Methods of Using BCMA-Specific Antibodies

Methods of using the described BCMA-specific antibodies or antigen-binding fragments are also disclosed. Particular antibodies for use in the methods discussed in this section include those with the set of CDRs described for antibodies in Table 1. For example, these antibodies or antigen-binding fragments may be useful in treating cancer, by interfering with BCMA-receptor interactions or where the antibody is conjugated to a toxin, so targeting the toxin to the BCMA-expressing cancer. Further, these antibodies or antigen-binding fragments may be useful for detecting the presence of BCMA in a biological sample, such as blood or serum; for quantifying the amount of BCMA in a biological sample, such as blood or serum; for diagnosing BCMA-expressing cancer; determining a method of treating a subject afflicted with cancer; or monitoring the progression of BCMA-expressing cancer in a subject. In some embodiments, BCMA-expressing cancer may be a lymphoma, such as multiple myeloma (MM). The described methods may be carried out before the subject receives treatment for BCMA-expressing cancer, such as treatment with a multispecific antibody against BCMA and CD3. Furthermore, the described methods may be carried out after the subject receives treatment for BCMA-expressing cancer, such as treatment with a multispecific antibody against BCMA and CD3 described herein.

The described methods of detecting BCMA in a biological sample include exposing the biological sample to one or more of the BCMA-specific antibodies or antigen-binding fragments described herein.

The described methods of diagnosing BCMA-expressing cancer in a subject also involve exposing the biological sample to one or more of the BCMA-specific antibodies or antigen-binding fragments described herein; however, the methods also include quantifying the amount of BCMA present in the sample; comparing the amount of BCMA present in the sample to a known standard or reference sample; and determining whether the subject's BCMA levels fall within the levels of BCMA associated with cancer.

Also described herein are methods of monitoring BCMA-expressing cancer in a subject. The described methods include exposing the biological sample to one or more of the BCMA-specific antibodies or antigen-binding fragments described herein; quantifying the amount of BCMA present in the sample that is bound by the antibody, or antigen-binding fragment thereof; comparing the amount of BCMA present in the sample to either a known standard or reference sample or the amount of BCMA in a similar sample previously obtained from the subject; and determining whether the subject's BCMA levels are indicative of cancer progression, regression or stable disease based on the difference in the amount of BCMA in the compared samples.

The samples obtained, or derived from, subjects are biological samples such as urine, blood, serum, plasma, saliva, ascites, circulating cells, circulating tumor cells, cells that are not tissue associated, tissues, surgically resected tumor tissue, biopsies, fine needle aspiration samples, or histological preparations.

The described BCMA-specific antibodies or antigen-binding fragments may be labeled for use with the described methods, or other methods known to those skilled in the art. For example, the antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

BCMA-Specific Antibody Kits

Described herein are kits including the disclosed BCMA-specific antibodies or antigen-binding fragments thereof. The described kits may be used to carry out the methods of using the BCMA-specific antibodies or antigen-binding fragments provided herein, or other methods known to those skilled in the art. In some embodiments the described kits may include the antibodies or antigen-binding fragments described herein and reagents for use in detecting the presence of BCMA in a biological sample. Accordingly, the described kits may include one or more of the antibodies, or an antigen-binding fragment(s) thereof, described herein and a vessel for containing the antibody or fragment when not in use, instructions for use of the antibody or fragment, the antibody or fragment affixed to a solid support, and/or detectably labeled forms of the antibody or fragment, as described herein.

BCMA×CD3-Multispecific Antibodies

The redirection of T-lymphocytes to MM cells expressing BCMA via the TCR/CD3 complex represents an attractive alternative approach. The TCR/CD3 complex of T-lymphocytes consists of either a TCR alpha (α)/beta ((β) or TCR gamma (γ)/delta (δ) heterodimer coexpressed at the cell surface with the invariant subunits of CD3 labeled gamma (γ), delta (δ), epsilon (ϵ), zeta (ζ), and eta (η). Human CD3ϵ is described under UniProt P07766 (CD3E_HUMAN). An anti CD3ϵ antibody described in the state of the art is SP34 (Yang S J, The Journal of Immunology (1986) 137; 1097-1100). SP34 reacts with both primate and human CD3. SP34 is available from Pharmingen. A further anti CD3 antibody described in the state of the art is UCHT-1 (see WO2000041474). A further anti CD3 antibody described in the state of the art is BC-3 (Fred Hutchinson Cancer Research Institute; used in Phase I/II trials of GvHD, Anasetti et al., Transplantation 54: 844 (1992)). SP34 differs from UCHT-1 and BC-3 in that SP-34 recognizes an epitope present on solely the ϵ chain of CD3 (see Salmeron et al., (1991) J. Immunol. 147: 3047) whereas UCHT-1 and BC-3 recognize an epitope contributed by both the ϵ and γ chains. The sequence of an antibody with the same sequence as of antibody SP34 is mentioned in WO2008119565, WO2008119566, WO2008119567, WO2010037836, WO2010037837 and WO2010037838. A sequence which is 96% identical to the heavy chain variable domain (VH) of antibody SP34 is mentioned in U.S. Pat. No. 8,236,308 (WO2007042261).

A variety of bispecific antibodies against CD3 and BCMA are mentioned in WO2007117600, WO2009132058, WO2012066058, WO2012143498, WO2013072406, WO2013072415, and WO2014122144. However, no data describing progression to the clinic is currently available.

Described herein are recombinant multispecific antibodies that bind BCMA and CD3 ("BCMA×CD3 multispecific antibodies") and multispecific antigen-binding fragments thereof. In some embodiments a recombinant antibody, or an antigen-binding fragment thereof, that binds immunospecifically to BCMA is provided.

In some embodiments, the BCMA-specific arm of the multispecific antibody binds human BCMA and cynomolgus monkey BCMA. In some embodiments, the BCMA-specific arm of the BCMA×CD3-multispecific antibodies or antigen-binding fragments binds the extracellular domain of human BCMA. In preferred embodiments, the BCMA×CD3 multispecific antibody or antigen-binding fragment is a bispecific antibody or antigen-binding fragment. In some embodiments, a recombinant BCMA×CD3 bispecific antibody comprising: a) a first heavy chain (HC1); b) a second heavy chain (HC2); c) a first light chain (LC1); and d) a second light chain (LC2), wherein the HC1 and the LC1 pair to form a first antigen-binding site that immunospecifically binds BCMA, and the HC2 and the LC2 pair to form a second antigen-binding site that immunospecifically binds CD3, or a BCMA×CD3-bispecific binding fragment thereof is provided. In another embodiment, a recombinant cell expressing the antibody or bispecific binding fragment is provided. In some embodiments, the BCMA-binding arm (or "BCMA-specific arm") of the BCMA×CD3 multispecific antibody is derived from a BCMA antibody described herein (for example, from an antibody having the CDR sequences listed in Table 1).

In some embodiments, the BCMA-specific arm of the BCMA×CD3-multispecific antibodies or antigen-binding fragments are IgG, or derivatives thereof. In some embodiments the described BCMA×CD3-multispecific antibodies are capable of binding to BCMA with a dissociation constant of at least 0.18 nM as measured by surface plasmon resonance. In some embodiments the described BCMA×CD3-multispecific antibody is not an agonist. In some embodiments the described BCMA×CD3-multispecific antibody does not alter NF-κB activation at concentrations below 10 nM.

In some embodiments, the CD3-binding arm (or "CD3-specific arm") of the BCMA×CD3 multispecific antibody is derived from the mouse monoclonal antibody SP34, a mouse IgG3/lambda isotype. (K. R. Abhinandan and A. C. Martin, 2008. Mol. Immunol. 45, 3832-3839). In some embodiments, the CD3-binding arm of the BCMA×CD3 multispecific antibody comprises one heavy chain and one light chain selected from Table 2.

TABLE 2

Heavy chains and light chains of the CD3-specific antibodies and antigen binding fragments.

| Heavy chain | Light chain |
|---|---|
| CD3B219 (SEQ ID NO: 55):<br>EVQLVESGGGLVQPGGSLRLSCAASGFTFN<br>TYAMNWVRQAPGKGLEWVARIRSKYNNYAT<br>YYAASVKGRFTISRDDSKNSLYLQMNSLKTE<br>DTAVYYCARHGNFGNSYVSWFAYWGQGTL<br>VTVSSASTKGPSVFPLAPCSRSTSESTAALG<br>CLVKDYFPEPVTVSWNSGALTSGVHTFPAVL<br>QSSGLYSLSSVVTVPSSSLGTKTYTCNVDHK<br>PSNTKVDKRVESKYGPPCPPCPAPEAAGGP<br>SVFLFPPKPKDTLMISRTPEVTCVVVDVSQED<br>PEVQFNWYVDGVEVHNAKTKPREEQFNSTY<br>RVVSVLTVLHQDWLNGKEYKCKVSNKGLPS<br>SIEKTISKAKGQPREPQVYTLPPSQEEMTKN<br>QVSLTCLVKGFYPSDIAVEWESNGQPENNYK<br>TTPPVLDSDGSFLLYSKLTVDKSRWQEGNVF<br>SCSVMHEALHNHYTQKSLSLSLGK | CD3B219 (SEQ ID NO: 56):<br>QTVVTQEPSLTVSPGGTVTLTCRSSTGAVTTSNYA<br>NWVQQKPGQAPRGLIGGTNKRAPGTPARFSGSLL<br>GGKAALTLSGVQPEDEAEYYCALWYSNLWVFGG<br>GTKLTVLGQPKAAPSVTLFPPSSEELQANKATLVC<br>LISDFYPGAVTVAWKADSSPVKAGVETTTPSKQSN<br>NKYAASSYLSLTPEQWKSHRSYSCQVTHEGSTVE<br>KTVAPTECS |
| CDR 1: TYAMN (SEQ ID NO: 59) | CDR 1: RSSTGAVTTSNYAN (SEQ ID NO: 62) |
| CDR 2: RIRSKYNNYATYYAASVKG (SEQ ID NO: 60) | CDR 2: GTNKRAP (SEQ ID NO: 63) |
| CDR 3: HGNFGNSYVSWFAY (SEQ ID NO: 61) | CDR 3: ALWYSNLWV (SEQ ID NO: 64) |

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcgRs) on the surface of immune effector cells such as natural killers and macrophages, leading to the phagocytosis or lysis of the targeted cells. In CDC, the antibodies kill the targeted cells by triggering the complement cascade at the cell surface.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcgRs or the complement factors. The binding of IgG to the activating (FcgRI, FcgRIIa, FcgRIIIa and FcgRIIIb) and inhibitory (FcgRIIb) FcgRs or the first component of complement (C1q) depends on residues located in the hinge region and the CH2 domain. Mutations have been introduced in IgG1, IgG2 and IgG4 to reduce or silence Fc functionalities.

In one embodiment, the antibody comprises an Fc region with one or more of the following properties: (a) reduced effector function when compared to the parent Fc; (b)

reduced affinity to Fcg RI, Fcg RIIa, Fcg RIIb, Fcg RIIIb and/or Fcg RIIIa, (c) reduced affinity to FcgRI (d) reduced affinity to FcgRIIa (e) reduced affinity to FcgRIIb, (f) reduced affinity to Fcg RIIIb or (g) reduced affinity to FcgRIIIa.

In some embodiments, the CD3-specific antibody or antigen-binding fragment from which the CD3-specific arm of the multispecific antibody is derived is IgG, or a derivative thereof. In some embodiments, the CD3-specific antibody or antigen-binding fragment from which the CD3-specific arm of the multispecific antibody is derived is IgG1, or a derivative thereof. In some embodiments, for example, the Fc region of the CD3-specific IgG1 antibody from which the CD3-binding arm is derived comprises L234A, L235A, and F405L substitutions in its Fc region. In some embodiments, the CD3-specific antibody or antigen-binding fragment from which the CD3-specific arm of the multispecific antibody is derived is IgG4, or a derivative thereof. In some embodiments, for example, the Fc region of the CD3-specific IgG4 antibody from which the CD3-binding arm is derived comprises S228P, L234A, L235A, F405L, and R409K substitutions in its Fc region. In some embodiments, the CD3-specific antibody or antigen-binding fragment from which the CD3-specific arm of the multispecific antibody is derived binds CD3ϵ on primary human T cells and/or primary cynomolgus T cells. In some embodiments, the CD3-specific antibody or antigen-binding fragment from which the CD3-specific arm of the multispecific antibody is derived activates primary human CD4+ T cells and/or primary cynomolgus CD4+ T cells.

In addition to the described BCMA×CD3-multispecific antibodies, also provided are polynucleotide sequences capable of encoding the described BCMA×CD3-multispecific antibodies. In some embodiments, an isolated synthetic polynucleotide encoding the HC1, the HC2, the LC1 or the LC2 of the BCMA×CD3 bispecific antibody or bispecific binding fragment is provided. Vectors comprising the described polynucleotides are also provided, as are cells expressing the BCMA×CD3-multispecific antibodies provided herein. Also described are cells capable of expressing the disclosed vectors. These cells may be mammalian cells (such as 293F cells, CHO cells), insect cells (such as Sf7 cells), yeast cells, plant cells, or bacteria cells (such as E. coli). The described antibodies may also be produced by hybridoma cells. In some embodiments, methods for generating the BCMA×CD3 bispecific antibody or bispecific binding fragment by culturing cells is provided.

Further provided herein are pharmaceutical compositions comprising the BCMA×CD3 multispecific antibodies or antigen-binding fragments and a pharmaceutically acceptable carrier.

Methods of Using BCMA×CD3-Multispecific Antibodies

Methods of using the described BCMA×CD3-multi specific antibodies and multi specific antigen-binding fragments thereof are also disclosed. For example, the BCMA×CD3-multispecific antibodies and multispecific antigen-binding fragments thereof may be useful in the treatment of a BCMA-expressing cancer in a subject in need thereof. In some embodiments, the BCMA-expressing cancer is a lymphoma, such as multiple myeloma.

The described methods of treating BCMA-expressing cancer in a subject in need thereof include administering to the subject a therapeutically effective amount of a described BCMA×CD3-multispecific antibody or multispecific antigen-binding fragment thereof. In some embodiments, the subject is a mammal, preferably a human. In preferred embodiments are provided methods for treating a subject having cancer by administering a therapeutically effective amount of the BCMA×CD3 bispecific antibody or bispecific antigen-binding fragment to a patient in need thereof for a time sufficient to treat the cancer.

Further provided herein are methods for inhibiting growth or proliferation of cancer cells by administering a therapeutically effective amount of the BCMA×CD3 bispecific antibody or bispecific binding fragment to inhibit the growth or proliferation of cancer cells.

Also provided herein are methods of redirecting a T cell to a BCMA-expressing cancer cell by administering a therapeutically effective amount of the BCMA×CD3 bispecific antibody or bispecific binding fragment to redirect a T cell to a cancer.

BCMA×CD3-Specific Antibody Kits

Described herein are kits including the disclosed BCMA×CD3-multispecific antibodies. The described kits may be used to carry out the methods of using the BCMA×CD3-multispecific antibodies provided herein, or other methods known to those skilled in the art. In some embodiments the described kits may include the antibodies described herein and reagents for use in treating a BCMA-expressing cancer. Accordingly, the described kits may include one or more of the multispecific antibodies, or a multispecific antigen-binding fragment(s) thereof, described herein and a vessel for containing the antibody or fragment when not in use, and/or instructions for use of the antibody or fragment, the antibody or fragment affixed to a solid support, and/or detectably labeled forms of the antibody or fragment, as described herein.

DETAILED DESCRIPTION OF ILLUSTRATIVE EMBODIMENTS

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that specifically binds to BCMA is substantially free of antibodies that specifically bind antigens other than BCMA). An isolated antibody that specifically binds to an epitope, isoform or variant of BCMA may, however, have cross-reactivity to other related antigens, for instance from other species (such as BCMA species homologs).

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM 120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include BCMA specific antibodies, or antigen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 990/% identical to such sequences described herein.

A "vector" is a replicon, such as plasmid, phage, cosmid, or virus in which another nucleic acid segment may be operably inserted so as to bring about the replication or expression of the segment.

A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

An "effective amount" or "therapeutically effective amount" refers to an amount effective, at dosages and for periods of time necessary, to achieve a desired therapeutic result. A therapeutically effective amount of a BCMA×CD3 antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides, such as chimeric antibodies and humanized antibodies.

"Antigen-binding fragments" are any proteinaceous structure that may exhibit binding affinity for a particular antigen. Antigen-binding fragments include those provided by any known technique, such as enzymatic cleavage, peptide synthesis, and recombinant techniques. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL, VH, CL and CH1 domains, or a monovalent antibody as described in WO2007059782, bivalent fragments comprising two Fab fragments linked by a disulfide bridge at the hinge region, a Fd fragment consisting essentially of the V.sub.H and C.sub.H1 domains, a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 November; 21(11):484-90); camelid or nanobodies (Revets et al; Expert Opin Biol Ther. 2005 January; 5(1): 111-24); an isolated complementarity determining region (CDR), and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked or covered by the specifically antigen binding peptide (in other words, the amino acid residue is within the footprint of the specifically antigen binding peptide).

"Specific binding" or "immunospecific binding" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1\times10^{-8}$ M, as measured by a surface plasmon resonance assay or a cell binding assay. Phrases such as "[antigen]-specific" antibody (e.g., BCMA-specific antibody) are meant to convey that the recited antibody specifically binds the recited antigen.

The term "$K_D$", as used herein, refers to the dissociation equilibrium constant of a particular antibody-antigen interaction.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

A "known standard" may be a solution having a known amount or concentration of BCMA, where the solution may be a naturally occurring solution, such as a sample from a patient known to have early, moderate, late, progressive, or static cancer, or the solution may be a synthetic solution such as buffered water having a known amount of BCMA diluted therein. The known standards, described herein may include BCMA isolated from a subject, recombinant or purified BCMA protein, or a value of BCMA concentration associated with a disease condition.

The term "BCMA" as used herein relates to human B cell maturation antigen, also known as BCMA, CD269, and TNFRSF17 (UniProt Q02223), which is a member of the tumor necrosis receptor superfamily that is preferentially expressed in differentiated plasma cells. The extracellular domain of human BCMA consists, according to UniProt of amino acids 1-54 (or 5-51). The term "antibody against BCMA, anti BCMA antibody" as used herein relates to an antibody immunospecifically binding to BCMA.

The term "CD3" refers to the human CD3 protein multi-subunit complex. The CD3 protein multi-subunit complex is composed to 6 distinctive polypeptide chains. These include a CD3γ chain (SwissProt P09693), a CD3δ chain (SwissProt P04234), two CD3ϵ chains (SwissProt P07766), and one CD3ζ chain homodimer (SwissProt 20963), and which is associated with the T cell receptor α and β chain. The term "CD3" includes any CD3 variant, isoform and species homolog which is naturally expressed by cells (including T cells) or can be expressed on cells transfected with genes or cDNA encoding those polypeptides, unless noted.

A "BCMA×CD3 antibody" is a multispecific antibody, optionally a bispecific antibody, which comprises two different antigen-binding regions, one of which binds specifically to the antigen BCMA and one of which binds specifically to CD3. A multispecific antibody can be a bispecific antibody, diabody, or similar molecule (see for instance PNAS USA 90(14), 6444-8 (1993) for a description of diabodies). The bispecific antibodies, diabodies, and the like, provided herein may bind any suitable target in addition to a portion of BCMA. The term "bispecific antibody" is to be understood as an antibody having two different antigen-binding regions defined by different antibody sequences. This can be understood as different target binding but includes as well binding to different epitopes in one target.

A "reference sample" is a sample that may be compared against another sample, such as a test sample, to allow for characterization of the compared sample. The reference sample will have some characterized property that serves as the basis for comparison with the test sample. For instance, a reference sample may be used as a benchmark for BCMA levels that are indicative of a subject having cancer. The reference sample does not necessarily have to be analyzed in parallel with the test sample, thus in some instances the reference sample may be a numerical value or range previously determined to characterize a given condition, such as BCMA levels that are indicative of cancer in a subject. The term also includes samples used for comparative purposes that are known to be associated with a physiologic state or disease condition, such as BCMA-expressing cancer, but that have an unknown amount of BCMA.

The term "progression," as used in the context of progression of BCMA-expressing cancer, includes the change of a cancer from a less severe to a more severe state. This may include an increase in the number or severity of tumors, the degree of metastasis, the speed with which the cancer is growing or spreading, and the like. For example, "the progression of colon cancer" includes the progression of such a cancer from a less severe to a more severe state, such as the progression from stage I to stage II, from stage II to stage III, etc.

The term "regression," as used in the context of regression of BCMA-expressing cancer, includes the change of a cancer from a more severe to a less severe state. This could include a decrease in the number or severity of tumors, the degree of metastasis, the speed with which the cancer is growing or spreading, and the like. For example, "the regression of colon cancer" includes the regression of such a cancer from a more severe to a less severe state, such as the progression from stage III to stage II, from stage II to stage I, etc.

The term "stable" as used in the context of stable BCMA-expressing cancer, is intended to describe a disease condition that is not, or has not, changed significantly enough over a clinically relevant period of time to be considered a progressing cancer or a regressing cancer.

The embodiments described herein are not limited to particular methods, reagents, compounds, compositions or biological systems, which can, of course, vary.

BCMA-Specific Antibodies and Antigen-Binding Fragments

Described herein are recombinant monoclonal antibodies or antigen-binding fragments that specifically bind BCMA. The general structure of an antibody molecule comprises an antigen binding domain, which includes heavy and light chains, and the Fc domain, which serves a variety of functions, including complement fixation and binding antibody receptors.

The described BCMA-specific antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The BCMA-specific antibodies and antigen-binding fragments may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody CDRs shown in Table 1.

Described herein are recombinant antibodies and antigen-binding fragments that immunospecifically bind to BCMA. In some embodiments, the BCMA-specific antibodies or antigen-binding fragments are human IgG, or derivatives thereof. While the BCMA-specific antibodies or antigen-binding fragments exemplified herein are human, the antibodies or antigen-binding fragments exemplified may be chimerized.

In some embodiments are provided a BCMA-specific antibody, or an antigen-binding fragment thereof, comprising a heavy chain comprising a CDR1, a CDR2, and a CDR3 of any one of the antibodies described in Table 1. In some embodiments are provided a BCMA-specific antibody, or an antigen-binding fragment thereof, comprising a heavy chain comprising a CDR1, a CDR2, and a CDR3 of any one of the antibodies described in Table 1 and a light chain comprising a CDR1, a CDR2, and a CDR3 of any one of the antibodies described in Table 1.

In some embodiments, the BCMA-specific antibodies and antigen-binding fragments comprise a heavy chain CDR1 comprising SEQ ID NO: 4, a heavy chain CDR2 comprising SEQ ID NO: 5, and a heavy chain CDR3 comprising SEQ ID NO: 6. In some embodiments, the BCMA-specific antibodies and antigen-binding fragments comprise a heavy chain CDR1 comprising SEQ ID NO: 4, a heavy chain CDR2 comprising SEQ ID NO: 5, a heavy chain CDR3 comprising SEQ ID NO: 6, a light chain CDR1 comprising SEQ ID NO: 7, a light chain CDR2 comprising SEQ ID NO: 8, and a light chain CDR3 comprising SEQ ID NO: 9. This BCMA-specific antibody or antigen-binding fragment may comprise human framework sequences. This BCMA-specific antibody or antigen-binding fragment may block APRIL binding with an $IC_{50}$ of at least 5.9 nM. In some embodiments, the BCMA-specific antibodies and antigen-binding fragments comprise a heavy chain variable domain substantially the same as, or identical to, SEQ ID NO: 10. In some embodiments, the BCMA-specific antibodies and antigen-binding fragments comprise a heavy chain variable domain substantially the same as, or identical to, SEQ ID NO: 10 and a light chain variable domain substantially the same as, or identical to, SEQ ID NO: 11. The heavy chain variable domain and light chain variable domain of antibodies discussed in this paragraph are suitable for inclusion in bispecific constructs in which one arm is an anti-BCMA arm.

In some embodiments, the BCMA-specific antibodies and antigen-binding fragments comprise a heavy chain CDR1 comprising SEQ ID NO: 4, a heavy chain CDR2 comprising SEQ ID NO: 5, and a heavy chain CDR3 comprising SEQ ID NO: 6. In some embodiments, the BCMA-specific antibodies and antigen-binding fragments comprise a heavy chain CDR1 comprising SEQ ID NO: 7, a heavy chain CDR2 comprising SEQ ID NO: 5, a heavy chain CDR3 comprising SEQ ID NO: 6, a light chain CDR1 comprising SEQ ID NO: 24, a light chain CDR2 comprising SEQ ID NO: 25, and a light chain CDR3 comprising SEQ ID NO: 26. This BCMA-specific antibody or antigen-binding fragment may comprise human framework sequences. In some embodiments, the BCMA-specific antibodies and antigen-binding fragments comprise a heavy chain variable domain substantially the same as, or identical to, SEQ ID NO: 57. In some embodiments, the BCMA-specific antibodies and antigen-binding fragments comprise a heavy chain variable domain substantially the same as, or identical to, SEQ ID NO: 57 and a light chain variable domain substantially the same as, or identical to, SEQ ID NO: 28. The heavy chain variable domain and light chain variable domain of antibodies discussed in this paragraph are suitable for inclusion in bispecific constructs in which one arm is an anti-BCMA arm.

In some embodiments, the BCMA-specific antibodies and antigen-binding fragments comprise a heavy chain CDR1 comprising SEQ ID NO: 7, a heavy chain CDR2 comprising SEQ ID NO: 5, and a heavy chain CDR3 comprising SEQ ID NO: 6. In some embodiments, the BCMA-specific antibodies and antigen-binding fragments comprise a heavy chain CDR1 comprising SEQ ID NO: 7, a heavy chain CDR2 comprising SEQ ID NO: 5, a heavy chain CDR3 comprising SEQ ID NO: 6, a light chain CDR1 comprising SEQ ID NO: 24, a light chain CDR2 comprising SEQ ID NO: 25, and a light chain CDR3 comprising SEQ ID NO: 26. This BCMA-specific antibody or antigen-binding fragment may comprise human framework sequences. In some embodiments, the BCMA-specific antibodies and antigen-binding fragments comprise a heavy chain variable domain substantially the same as, or identical to, SEQ ID NO: 34. In some embodiments, the BCMA-specific antibodies and antigen-binding fragments comprise a heavy chain variable domain substantially the same as, or identical to, SEQ ID NO: 34 and a light chain variable domain substantially the same as, or identical to, SEQ ID NO: 28. The heavy chain variable domain and light chain variable domain of antibodies discussed in this paragraph are suitable for inclusion in bispecific constructs in which one arm is an anti-BCMA arm.

In some embodiments, the BCMA-specific antibodies and antigen-binding fragments comprise a heavy chain CDR1 comprising SEQ ID NO: 4, a heavy chain CDR2 comprising SEQ ID NO: 5, and a heavy chain CDR3 comprising SEQ ID NO: 19. In some embodiments, the BCMA-specific antibodies and antigen-binding fragments comprise a heavy chain CDR1 comprising SEQ ID NO: 4, a heavy chain CDR2 comprising SEQ ID NO: 5, a heavy chain CDR3 comprising SEQ ID NO: 19, a light chain CDR1 comprising SEQ ID NO: 24, a light chain CDR2 comprising SEQ ID NO: 25, and a light chain CDR3 comprising SEQ ID NO: 26. This BCMA-specific antibody or antigen-binding fragment may comprise human framework sequences. In some embodiments, the BCMA-specific antibodies and antigen-binding fragments comprise a heavy chain variable domain substantially the same as, or identical to, SEQ ID NO: 39. In some embodiments, the BCMA-specific antibodies and antigen-binding fragments comprise a heavy chain variable domain substantially the same as, or identical to, SEQ ID NO: 39 and a light chain variable domain substantially the same as, or identical to, SEQ ID NO: 28. The heavy chain variable domain and light chain variable domain of antibodies discussed in this paragraph are suitable for inclusion in bispecific constructs in which one arm is an anti-BCMA arm.

In some embodiments, the BCMA-specific antibodies and antigen-binding fragments comprise a heavy chain CDR1 comprising SEQ ID NO: 4, a heavy chain CDR2 comprising SEQ ID NO: 8, and a heavy chain CDR3 comprising SEQ ID NO: 6. In some embodiments, the BCMA-specific antibodies and antigen-binding fragments comprise a heavy chain CDR1 comprising SEQ ID NO: 4, a heavy chain CDR2 comprising SEQ ID NO: 8, a heavy chain CDR3 comprising SEQ ID NO: 6, a light chain CDR1 comprising SEQ ID NO: 24, a light chain CDR2 comprising SEQ ID NO: 25, and a light chain CDR3 comprising SEQ ID NO: 26. This BCMA-specific antibody or antigen-binding fragment may comprise human framework sequences. In some embodiments, the BCMA-specific antibodies and antigen-binding fragments comprise a heavy chain variable domain substantially the same as, or identical to, SEQ ID NO: 40. In some embodiments, the BCMA-specific antibodies and antigen-binding fragments comprise a heavy chain variable domain substantially the same as, or identical to, SEQ ID NO: 40 and a light chain variable domain substantially the same as, or identical to, SEQ ID NO: 28. The heavy chain variable domain and light chain variable domain of antibodies discussed in this paragraph are suitable for inclusion in bispecific constructs in which one arm is an anti-BCMA arm.

In some embodiments, the BCMA-specific antibodies and antigen-binding fragments comprise a heavy chain CDR1 comprising SEQ ID NO: 13, a heavy chain CDR2 comprising SEQ ID NO: 5, and a heavy chain CDR3 comprising SEQ ID NO: 19. In some embodiments, the BCMA-specific antibodies and antigen-binding fragments comprise a heavy chain CDR1 comprising SEQ ID NO: 13, a heavy chain CDR2 comprising SEQ ID NO: 5, a heavy chain CDR3 comprising SEQ ID NO: 19, a light chain CDR1 comprising SEQ ID NO: 24, a light chain CDR2 comprising SEQ ID NO: 25, and a light chain CDR3 comprising SEQ ID NO: 26. This BCMA-specific antibody or antigen-binding fragment may comprise human framework sequences. In some embodiments, the BCMA-specific antibodies and antigen-binding fragments comprise a heavy chain variable domain substantially the same as, or identical to, SEQ ID NO: 58. In some embodiments, the BCMA-specific antibodies and antigen-binding fragments comprise a heavy chain variable domain substantially the same as, or identical to, SEQ ID NO: 58 and a light chain variable domain substantially the same as, or identical to, SEQ ID NO: 28. The heavy chain variable domain and light chain variable domain of antibodies discussed in this paragraph are suitable for inclusion in bispecific constructs in which one arm is an anti-BCMA arm.

In some embodiments, the BCMA-specific antibodies and antigen-binding fragments comprise a heavy chain CDR1 comprising SEQ ID NO: 13, a heavy chain CDR2 comprising SEQ ID NO: 8, and a heavy chain CDR3 comprising SEQ ID NO: 19. In some embodiments, the BCMA-specific antibodies and antigen-binding fragments comprise a heavy chain CDR1 comprising SEQ ID NO: 13, a heavy chain CDR2 comprising SEQ ID NO: 8, a heavy chain CDR3 comprising SEQ ID NO: 19, a light chain CDR1 comprising SEQ ID NO: 24, a light chain CDR2 comprising SEQ ID NO: 25, and a light chain CDR3 comprising SEQ ID NO: 26. This BCMA-specific antibody or antigen-binding fragment may comprise human framework sequences. In some embodiments, the BCMA-specific antibodies and antigen-binding fragments comprise a heavy chain variable domain substantially the same as, or identical to, SEQ ID NO: 43. In some embodiments, the BCMA-specific antibodies and antigen-binding fragments comprise a heavy chain variable domain substantially the same as, or identical to, SEQ ID NO: 43 and a light chain variable domain substantially the same as, or identical to, SEQ ID NO: 28. The heavy chain variable domain and light chain variable domain of antibodies discussed in this paragraph are suitable for inclusion in bispecific constructs in which one arm is an anti-BCMA arm.

In some embodiments, the antibodies or antigen-binding fragments are IgG, or derivatives thereof, e.g., IgG1, IgG2, IgG3, and IgG4 isotypes. In some embodiments wherein the antibody is of IgG1 isotype, the antibody comprises an IgG1 Fc region (SEQ ID NO. 74).

```
                                        SEQ ID NO. 74
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVER

KSCDKATITCPPCPAPELLGGPSVFLFPPKPKDTLMISRTPEVTCVVVDV

SHEDPEVKFNWYWDGVEVHNAKTKPREEQYNSTYRVVSVLTVLHQDWLNG

KEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSR

WQQGNVFSCSVMHEALHNHYTQKSLSLSPGK
```

In some embodiments wherein the antibody is of IgG4 isotype, the antibody contains S228P, L234A, and L235A substitutions in its Fc region (SEQ ID NO. 73).

```
                                        SEQ ID NO. 73
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEAAGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK
```

The specific antibodies defined by CDR and/or variable domain sequence discussed in the above paragraphs may include these IgG Fc regions.

Also disclosed are isolated synthetic polynucleotides that encode the antibodies or antigen-binding fragments that immunospecifically bind to BCMA. The isolated polynucleotides capable of encoding the variable domain segments provided herein may be included on the same, or different, vectors to produce antibodies or antigen-binding fragments.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The BCMA-specific antibodies or antigen-binding fragments described herein include variants having single or multiple amino acid substitutions, deletions, or additions that retain the biological properties (e.g., binding affinity or immune effector activity) of the described BCMA-specific antibodies or antigen-binding fragments. In the context of the present invention the following notations are, unless otherwise indicated, used to describe a mutation, i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Arginine for Lysine in position 409 is designated as: K409R, or the substitution of any amino acid residue for Lysine in position 409 is designated as K409X. In case of deletion of Lysine in position 409 it is indicated by K409*. The skilled person may produce variants having single or multiple amino acid substitutions, deletions, or additions.

These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The BCMA-specific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The BCMA-specific antibodies or antigen-binding fragments described herein have $IC_{50}$ values of at least 5.9 nM for APRIL binding. The $IC_{50}$ of the described BCMA-specific antibodies, or antigen-binding fragments, may be determined by a variety of methods known in the art, such as ELISA-based methods or flow cytometry (FACS). Assays for measuring $IC_{50}$ by ELISA have plate-bound BCMA in the presence and absence of a BCMA specific antibody and varying concentrations of the APRIL are used. A BCMA antibody that blocks the binding of APRIL to BCMA is to "block APRIL as measured by ELISA."

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 Mol. Cell. Biol. 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the BCMA-specific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene, a puromycin resistance gene, a blasticidin resistance gene), glutamate synthase genes, HSV-TK, HSV-TK derivatives for ganciclovir selection, or bacterial purine nucleoside phosphorylase gene for 6-methylpurine selection (Gadi et al., 7 Gene Ther. 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate BCMA-specific antibody or antigen-binding fragment-producing cells. Thus, another aspect features host cells transformed with vectors comprising a nucleic acid sequence encoding an antibody or antigen-binding fragment thereof that specifically binds BCMA, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 Pharmac. Ther. 69-92 (1985)). Calcium phosphate precipitation and polyethylene glycol (PEG)-induced fusion of bacterial protoplasts with mammalian cells may also be used to transform cells.

Cells suitable for use in the expression of the BCMA-specific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Methods of Using BCMA-Specific Antibodies for Treatment

Provided herein are BCMA-specific antibodies or antigen-binding fragments thereof for use in therapy. In particular, these antibodies or antigen-binding fragments may be useful in treating cancer, such as BCMA-expressing cancer. Accordingly, the invention provides a method of treating cancer comprising administering an antibody as described herein, such as BCMA-specific antibodies or antigen-binding fragments. For example, the use may be by interfering with BCMA-receptor interactions or where the antibody is conjugated to a toxin, so targeting the toxin to the BCMA-expressing cancer. In some embodiments BCMA-expressing cancer includes lymphoma, such as multiple myeloma (MM). The antibodies for use in these methods include those described herein above, for example a BCMA-specific antibody or antigen-binding fragment with the features set out in Table 1, for example the CDRs or variable domain sequences, and in the further discussion of these antibodies.

In some embodiments described herein, immune effector properties of the BCMA-specific antibodies may be enhanced or silenced through Fc modifications by techniques known to those skilled in the art. For example, Fc effector functions such as C1q binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor, BCR), etc. may be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of monoclonal antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved Fc.gamma.RIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the .alpha. 1,6-fucosyltrasferase (FUT8) gene (Mori et al., Biotechnol Bioeng 88:901-908, 2004), or coexpression of β-1, 4-N-acetylglucosaminyltransferase III and golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the BCMA antibodies may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

Methods of Detecting BCMA

Provided herein are methods for detecting BCMA in a biological sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the described methods include detecting BCMA in a biological sample by contacting the sample with any of the BCMA-specific antibodies or antigen-binding fragments thereof described herein.

In some embodiments the sample may be contacted with more than one of the BCMA-specific antibodies or antigen-binding fragments described herein. For example, a sample may be contacted with a first BCMA-specific antibody, or antigen-binding fragment thereof, and then contacted with a second BCMA-specific antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

The described BCMA-specific antibodies and antigen-binding fragments may be detectably labeled. In some embodiments labeled antibodies and antigen-binding fragments may facilitate the detection BCMA via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In-DOTA, $^{111}$In-diethylenetriamine-pentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described BCMA-specific antibodies and antigen-binding fragments may be used in a variety of assays to detect BCMA in a biological sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In some embodiments described herein detection of BCMA-expressing cancer cells in a subject may be used to determine that the subject may be treated with a therapeutic agent directed against BCMA.

BCMA is present at detectable levels in blood and serum samples. Thus, provided herein are methods for detecting BCMA in a sample derived from blood, such as a serum sample, by contacting the sample with an antibody, or antigen-binding fragment thereof, that specifically binds BCMA. The blood sample, or a derivative thereof, may be diluted, fractionated, or otherwise processed to yield a sample upon which the described method may be performed. In some embodiments, BCMA may be detected in a blood sample, or a derivative thereof, by any number of assays known in the art, such as, but not limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Methods for Diagnosing Cancer

Provided herein are methods for diagnosing BCMA-expressing cancer in a subject. In some embodiments BCMA-expressing cancer include lymphomas, such as multiple myeloma (MM). In some embodiments, as described above, detecting BCMA in a biological sample, such as a blood sample or a serum sample, provides the ability to diagnose cancer in the subject from whom the sample was obtained. Alternatively, in some embodiments other samples such as a histological sample, a fine needle aspirate sample, resected tumor tissue, circulating cells, circulating tumor cells, and the like, may also be used to assess whether the subject from whom the sample was obtained has cancer. In some embodiments, it may already be known that the subject from whom the sample was obtained has cancer, but the type of cancer afflicting the subject may not yet have been diagnosed or a preliminary diagnosis may be unclear, thus detecting BCMA in a biological sample obtained from the subject can allow for, or clarify, diagnosis of the cancer. For example, a subject may be known to have cancer, but it may not be known, or may be unclear, whether the subject's cancer is BCMA-expressing.

In some embodiments the described methods involve assessing whether a subject is afflicted with BCMA-expressing cancer by determining the amount of BCMA that is present in a biological sample derived from the subject; and comparing the observed amount of BCMA with the amount of BCMA in a control, or reference, sample, wherein a difference between the amount of BCMA in the sample derived from the subject and the amount of BCMA in the control, or reference, sample is an indication that the subject is afflicted with a BCMA-expressing cancer. In another embodiment the amount of BCMA observed in a biological sample obtained from a subject may be compared to levels of BCMA known to be associated with certain forms or stages of cancer, to determine the form or stage of the subject's cancer. In some embodiments the amount of BCMA in the sample derived from the subject is assessed by contacting the sample with an antibody, or an antigen-binding fragment thereof, that immunospecifically binds BCMA, such as the BCMA-specific antibodies described herein. The sample assessed for the presence of BCMA may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments BCMA-expressing cancer includes hematological cancer, such as multiple myeloma (MM). In some embodiments the subject is a human.

In some embodiments the method of diagnosing a BCMA-expressing cancer will involve: contacting a biological sample of a subject with a BCMA-specific antibody, or an antigen-binding fragment thereof (such as those derivable from the antibodies and fragments provided in Table 1), quantifying the amount of BCMA present in the sample that is bound by the antibody or antigen-binding fragment thereof, comparing the amount of BCMA present in the sample to a known standard or reference sample; and determining whether the subject's BCMA levels fall within the levels of BCMA associated with cancer. In an additional embodiment, the diagnostic method can be followed with an additional step of administering or prescribing a cancer-specific treatment. In another embodiment, the diagnostic method can be followed with an additional step of transmitting the results of the determination to facilitate treatment of the cancer. In some embodiments the cancer-specific treatment may be directed against BCMA-expressing cancers, such as the BCMA×CD3 multispecific antibodies described herein.

In some embodiments the described methods involve assessing whether a subject is afflicted with BCMA-expressing cancer by determining the amount of BCMA present in a blood or serum sample obtained from the subject; and comparing the observed amount of BCMA with the amount of BCMA in a control, or reference, sample, wherein a difference between the amount of BCMA in the sample derived from the subject and the amount of BCMA in the control, or reference, sample is an indication that the subject is afflicted with a BCMA-expressing cancer.

In some embodiments the control, or reference, sample may be derived from a subject that is not afflicted with BCMA-expressing cancer. In some embodiments the control, or reference, sample may be derived from a subject that is afflicted with BCMA-expressing cancer. In some embodiments where the control, or reference, sample is derived from a subject that is not afflicted with BCMA-expressing cancer, an observed increase in the amount of BCMA present in the test sample, relative to that observed for the control or reference sample, is an indication that the subject being assessed is afflicted with BCMA-expressing cancer. In some embodiments where the control sample is derived from a subject that is not afflicted with BCMA-expressing cancer, an observed decrease or similarity in the amount of BCMA present in the test sample, relative to that observed for the control or reference sample, is an indication that the subject being assessed is not afflicted with BCMA-expressing cancer. In some embodiments where the control or reference sample is derived from a subject that is afflicted with BCMA-expressing cancer, an observed similarity in the amount of BCMA present in the test sample, relative to that observed for the control or reference sample, is an indication that the subject being assessed is afflicted with BCMA-expressing cancer. In some embodiments where the control or reference sample is derived from a subject that is afflicted with BCMA-expressing cancer, an observed decrease in the amount of BCMA present in the test sample, relative to that observed for the control or reference sample, is an indication that the subject being assessed is not afflicted with BCMA-expressing cancer.

In some embodiments the amount of BCMA in the sample derived from the subject is assessed by contacting the sample with an antibody, or an antigen-binding fragment thereof, that specifically binds BCMA, such as the antibodies described herein. The sample assessed for the presence of BCMA may be derived from a blood sample, a serum sample, circulating cells, circulating tumor cells, cells that are not tissue associated (i.e., free cells), tissues (e.g., surgically resected tumor tissue, biopsies, including fine needle aspiration), histological preparations, and the like.

In various aspects, the amount of BCMA is determined by contacting the sample with an antibody, or antigen-binding fragment thereof, that specifically binds BCMA. In some embodiments, the sample may be contacted by more than one type of antibody, or antigen-binding fragment thereof, that specifically binds BCMA. In some embodiments, the sample may be contacted by a first antibody, or antigen-binding fragment thereof, that specifically binds BCMA and then contacted by a second antibody, or antigen-binding fragment thereof, that specifically binds BCMA. BCMA-specific antibodies or antigen-binding fragments such as those described herein may be used in this capacity.

Various combinations of the BCMA-specific antibodies and antigen-binding fragments can be used to provide a "first" and "second" antibody or antigen-binding fragment to carry out the described diagnostic methods. In some embodiments BCMA-expressing cancer includes lymphomas, such as multiple myeloma (MM).

In certain embodiments, the amount of BCMA is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In various embodiments of the described diagnostic methods a control or reference sample is used. This sample may be a positive or negative assay control that ensures the assay used is working properly; for example, an assay control of this nature might be commonly used for immunohistochemistry assays. Alternatively, the sample may be a standardized reference for the amount of BCMA in a biological sample from a healthy subject. In some embodiments, the observed BCMA levels of the tested subject may be compared with BCMA levels observed in samples from subjects known to have BCMA-expressing cancer. In some embodiments, the control subject may be afflicted with a particular cancer of interest. In some embodiments, the control subject is known to have early stage cancer, which may or may not be BCMA-expressing cancer. In some embodiments, the control subject is known to have intermediate stage cancer, which may or may not be BCMA-expressing cancer. In some embodiments, the control subject is known to have late stage, which may or may not be BCMA-expressing cancer.

Methods for Monitoring Cancer

Provided herein are methods for monitoring BCMA-expressing cancer in a subject. In some embodiments BCMA-expressing cancer includes lymphomas, such as multiple myeloma (MM). In some embodiments the described methods involve assessing whether BCMA-expressing cancer is progressing, regressing, or remaining stable by determining the amount of BCMA that is present in a test sample derived from the subject; and comparing the observed amount of BCMA with the amount of BCMA in a biological sample obtained, in a similar manner, from the subject at an earlier point in time, wherein a difference between the amount of BCMA in the test sample and the earlier sample provides an indication of whether the cancer is progressing, regressing, or remaining stable. In this regard, a test sample with an increased amount of BCMA, relative to the amount observed for the earlier sample, may indicate progression of a BCMA-expressing cancer. Conversely, a test sample with a decreased amount of BCMA, relative to the amount observed for the earlier sample, may indicate regression of a BCMA-expressing cancer.

Accordingly, a test sample with an insignificant difference in the amount of BCMA, relative to the amount observed for the earlier sample, may indicate a state of stable disease for a BCMA-expressing cancer. In some embodiments the amount of BCMA in a biological sample derived from the subject is assessed by contacting the sample with an antibody, or an antibody fragment thereof, that specifically binds BCMA, such as the antibodies described herein. The sample assessed for the presence of BCMA may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the subject is a human.

In some embodiments the methods of monitoring a BCMA-expressing cancer will involve: contacting a biological sample of a subject with a BCMA-specific antibody, or antigen-binding fragment thereof (such as those derivable from the antibodies and fragments provided in Table 1), quantifying the amount of BCMA present in the sample, comparing the amount of BCMA present in the sample to the amount of BCMA determined to be in a biological sample obtained, in a similar manner, from the same subject at an earlier point in time; and determining whether the subject's BCMA level has changed over time. A test sample with an increased amount of BCMA, relative to the amount observed for the earlier sample, may indicate progression of cancer. Conversely, a test sample with a decreased amount of BCMA, relative to the amount observed for the earlier sample, may indicate regression of a BCMA-expressing cancer. Accordingly, a test sample with an insignificant difference in the amount of BCMA, relative to the amount observed for the earlier sample, may indicate a state of stable disease for a BCMA-expressing cancer. In some embodiments, the BCMA levels of the sample may be compared to a known standard or a reference sample, alone or in addition to the BCMA levels observed for a sample assessed at an earlier point in time. In an additional embodiment, the diagnostic method can be followed with an additional step of administering a cancer-specific treatment. In some embodiments the cancer-specific treatment may be directed against BCMA-expressing cancers, such as the BCMA×CD3 multispecific antibodies described herein.

In various aspects, the amount of BCMA is determined by contacting the sample with an antibody, or antigen-binding fragment thereof, that specifically binds BCMA. In some embodiments, the sample may be contacted by more than one type of antibody, or antigen-binding fragment thereof, that specifically binds BCMA. In some embodiments, the sample may be contacted by a first antibody, or antigen-binding fragment thereof, that specifically binds BCMA and then contacted by a second antibody, or antigen-binding fragment thereof, that specifically binds BCMA. Antibodies such as those described herein may be used in this capacity.

Various combinations of the antibodies and antigen-binding fragments described in Table 1 can be used to provide a "first" and "second" antibody or antigen-binding fragment to carry out the described monitoring methods. In some embodiments BCMA-expressing cancer includes a hematological cancer, such as acute myeloid leukemia (AML).

In certain embodiments, the amount of BCMA is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Kits for Detecting BCMA

Provided herein are kits for detecting BCMA in a biological sample. These kits include one or more of the BCMA-specific antibodies described herein, or an antigen-binding fragment thereof, and instructions for use of the kit.

The provided BCMA-specific antibody, or antigen-binding fragment, may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of BCMA can further include, for example, buffers or other reagents for use in an assay for determining the level of BCMA. The instructions can be, for example, printed instructions for performing the assay and/or instructions for evaluating the level of expression of BCMA.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

Multispecific Antibodies

The binding domains of the anti-BCMA antibodies described herein recognize cells expressing BCMA on their surface. As noted above, BCMA expression can be indicative of a cancerous cell. More specific targeting to particular subsets of cells can be achieved by making bispecific molecules, such as antibodies or antibody fragments, which bind to BCMA and to another target, such as CD3. This is achieved by making a molecule which comprises a first region binding to BCMA and a second binding region binding to the other target antigen. The antigen-binding regions can take any form that allows specific recognition of the target, for example the binding region may be or may include a heavy chain variable domain, an Fv (combination of a heavy chain variable domain and a light chain variable domain), a binding domain based on a fibronectin type III domain (such as from fibronectin, or based on a consensus of the type III domains from fibronectin, or from tenascin or based on a consensus of the type III domains from tenascin, such as the Centyrin molecules from Janssen Biotech, Inc., see e.g. WO2010/051274 and WO2010/093627). Accordingly, bispecific molecules comprising two different antigen-binding regions which bind BCMA and another antigen, respectively, are provided.

Some of the multispecific antibodies described herein comprise two different antigen-binding regions which bind BCMA and CD3, respectively. In preferred embodiments, multispecific antibodies that bind BCMA and CD3 (BCMA× CD3-multispecific antibodies) and multispecific antigen-binding fragments thereof are provided. In some embodiments, the BCMA×CD3-multispecific antibody comprises a first heavy chain (HC1) and a first light chain (LC1) that pair to form a first antigen-binding site that immunospecifically binds BCMA and a second heavy chain (HC2) and a second light chain (LC2) that pair to form a second antigen-binding site that immunospecifically binds CD3. In preferred embodiments, the BCMA×CD3-multispecific antibody is a bispecific antibody comprising a BCMA-specific arm comprising a first heavy chain (HC1) and a first light chain (LC1) that pair to form a first antigen-binding site that immunospecifically binds CD3 and a CD3-specific arm comprising second heavy chain (HC2) and a second light chain (LC2) that pair to form a second antigen-binding site that immunospecifically binds BCMA. In some embodiments, the bispecific antibodies of the invention include antibodies having a full length antibody structure. "Full length antibody" as used herein refers to an antibody having two full length antibody heavy chains and two full length antibody light chains. A full length antibody heavy chain (HC) includes heavy chain variable and constant domains VH, CH1, CH2, and CH3. A full length antibody light chain (LC) includes light chain variable and constant domains VL and CL. The full length antibody may be lacking the C-terminal lysine (K) in either one or both heavy chains. The term "Fab-arm" or "half molecule" refers to one heavy chain-light chain pair that specifically binds an antigen. In some embodiments, one of the antigen-binding domains is a non-antibody based binding domain, e.g. a binding domain of based on a fibronectin type 3 domain, e.g. Centyrin.

The BCMA-binding arm of the multispecific antibodies provided herein may be derived from any of the BCMA-specific antibodies described above. In some exemplary embodiments of such BCMA-binding arms, the first antigen-binding region which binds BCMA comprises a heavy chain CDR1, CDR2, and CDR3 derived from an antibody clone as described in Table 1. In some exemplary embodiments of such BCMA-binding arms, the first antigen-binding region which binds BCMA comprises heavy chain CDR1, CDR2, and CDR3 and light chain CDR1, CDR2, and CDR3 derived from an antibody clone as described in Table 1. In some exemplary embodiments of such BCMA-binding arms, the first antigen-binding region which binds BCMA comprises heavy chain CDR1, CDR2, and CDR3 of clone BCMB69, BCMB117, BCMB123, BCMB128, BCMB129, BCMB176, or BCMB177. In some exemplary embodiments of such BCMA-binding arms, the first antigen-binding region which binds BCMA comprises heavy chain CDR1, CDR2, and CDR3 and light chain CDR1, CDR2, and CDR3 of clone BCMB69, BCMB117, BCMB123, BCMB128, BCMB129, BCMB176, or BCMB177. In some exemplary embodiments of such BCMA-binding arms, the first antigen-binding region which binds BCMA comprises a heavy chain variable domain derived from an antibody clone as described in Table 1. In some exemplary embodiments of such BCMA-binding arms, the first antigen-binding region which binds BCMA comprises heavy chain variable domain and light chain variable domain derived from an antibody clone as described in Table 1. In some exemplary embodiments of such BCMA-binding arms, the first antigen-binding region which binds BCMA comprises heavy chain variable domain of clone BCMB69, BCMB117, BCMB123, BCMB128, BCMB129, BCMB176, or BCMB177. In some exemplary embodiments of such BCMA-binding arms, the first antigen-binding region which binds BCMA comprises heavy chain variable domain and light chain variable domain of clone BCMB69, BCMB117, BCMB123, BCMB128, BCMB129, BCMB176, or BCMB177.

Table 3 provides a listing of BCMA×CD3 bispecific antibodies having one heavy and light chain pair specific for BCMA and another heavy and light chain pair specific for CD3, where the particular antibody ID is listed to describe the antigen-specific antibody arms used to produce the described embodiment.

TABLE 3

| BCMA-specific arm = Ab ID | CD3-specific arm =Ab ID |
|---|---|
| BCMB69 | CD3B219 |
| BCMB117 | CD3B219 |
| BCMB123 | CD3B219 |
| BCMB128 | CD3B219 |
| BCMB129 | CD3B219 |

TABLE 3-continued

| BCMA-specific arm = Ab ID | CD3-specific arm =Ab ID |
|---|---|
| BCMB176 | CD3B219 |
| BCMB177 | CD3B219 |

In some embodiments of the bispecific antibodies, the BCMA-binding arm binds also binds cynomolgus BCMA, preferably the extracellular domain thereof.

In some embodiments, the BCMA-binding arm of the multispecific antibody is IgG, or a derivative thereof, e.g., IgG1, IgG2, IgG3, and IgG4 isotypes. In some embodiments wherein the BCMA-binding arm has an IgG4 isotype, it contains S228P, L234A, and L235A substitution(s) in its Fc region.

In some embodiments of the bispecific antibodies, the second antigen-binding arm binds human CD3. In some preferred embodiments, the CD3-specific arm of the BCMA×CD3 bispecific antibody is derived from a CD3-specific antibody that binds and activates human primary T cells and/or cynomolgus monkey primary T cells. In some embodiments, the CD3-binding arm binds to an epitope at the N-terminus of CD3ϵ. In some embodiments, the CD3-binding arm contacts an epitope including the six N-terminal amino acids of CD3ϵ. In some embodiments, the CD3-specific binding arm of the bispecific antibody is derived from the mouse monoclonal antibody SP34, a mouse IgG3/lambda isotype. In some embodiments, the CD3-binding arm comprises the CDRs of antibody SP34. Such CD3-binding arms may bind to CD3 with an affinity of $5\times10^{-7}$M or less, such as $1\times10^{-7}$M or less, $5\times10^{-8}$M or less, $1\times10^{-8}$M or less, $5\times10^{-9}$M or less, or $1\times10^{-9}$M or less. The CD3-specific binding arm may be a humanized version of an arm of mouse monoclonal antibody SP34. Human framework adaptation (HFA) may be used to humanize the anti-CD3 antibody from which the CD3-specific arm is derived. In some embodiments of the bispecific antibodies, the CD3-binding arm comprises a heavy chain and light chain pair selected from Table 2. In other embodiments of the bispecific antibodies, the CD3-binding arm comprises heavy chain CDR1, CDR2, and CDR3 and light chain CDR1, CDR2, and CDR3 sequences set forth in Table 2. For example, the heavy chain and light chain CDR sequences of some embodiments of the CD3-binding arm of the bispecific antibodies described herein can include the following amino acid sequences: Hc CDR1, SEQ ID NO: 59; Hc CDR2: SEQ ID NO: 60; Hc CDR3, SEQ ID NO: 61; Lc CDR1, SEQ ID NO: 62; Lc CDR2: SEQ ID NO: 63; and Lc CDR3, SEQ ID NO: 64.

In some embodiments, the CD3-binding arm is IgG, or a derivative thereof. In some embodiments, the CD3-binding arm is IgG1, IgG2, IgG3, or IgG4. In some embodiments wherein the CD3-binding arm has an IgG4 isotype, it contains S228P, L234A, L235A, F405L, and R409K substitution(s) in its Fc region. In some embodiments, the antibodies or antigen-binding fragments bind CD3ϵ on primary human T cells. In some embodiments, the antibodies or antigen-binding fragments bind CD3ϵ on primary cynomolgus T cells. In some embodiments, the antibodies or antigen-binding fragments bind CD3ϵ on primary human and cynomolgus T cells. In some embodiments, the antibodies or antigen-binding fragments activate primary human CD4+ T cells. In some embodiments, the antibodies or antigen-binding fragments activate primary cynomolgus CD4+ T cells.

In some embodiments are provided a BCMA×CD3 bispecific antibody having a BCMA-binding arm comprising a heavy chain of antibody clone BCMB69, BCMB117, BCMB123, BCMB128, BCMB129, BCMB176, or BCMB177. In some embodiments are provided a BCMA×CD3 bispecific antibody having a BCMA-binding arm comprising a heavy chain and light chain of antibody clone BCMB69, BCMB117, BCMB123, BCMB128, BCMB129, BCMB176, or BCMB177. In some embodiments are provided a BCMA×CD3 bispecific antibody having a CD3-binding arm comprising a heavy chain of antibody clone CD3B219. In some embodiments are provided a BCMA×CD3 bispecific antibody having a CD3-binding arm comprising a heavy chain and light chain of antibody clone CD3B219. In some embodiments are provided a BCMA×CD3 bispecific antibody having a BCMA-binding arm comprising a heavy chain of antibody clone BCMB69, BCMB117, BCMB123, BCMB128, BCMB129, BCMB176, or BCMB177 and a CD3-binding arm comprising a heavy chain of antibody clone CD3B219. In some embodiments are provided a BCMA×CD3 bispecific antibody having a BCMA-binding arm comprising a heavy chain and light chain of antibody clone BCMB69, BCMB117, BCMB123, BCMB128, BCMB129, BCMB176, or BCMB177 and a CD3-binding arm comprising a heavy chain and light chain of antibody clone CD3B219.

An exemplary BCMA×CD3 bispecific antibody is provided in Tables 9.

Different formats of bispecific antibodies have been described and were recently reviewed by Chames and Baty (2009) Curr Opin Drug Disc Dev 12: 276.

In some embodiments, the bispecific antibody of the present invention is a diabody, a cross-body, or a bispecific antibody obtained via a controlled Fab arm exchange as those described in the present invention.

In some embodiments, the bispecific antibodies include IgG-like molecules with complementary CH3 domains to force heterodimerisation; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody)(EMD Serono), the Biclonic (Merus) and the DuoBody® (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules include to ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv).sub.2-Fab (National Research Center for Antibody Medicine—China).

In some embodiments, Fab fusion bispecific antibodies include F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based and domain antibodies include but are not limited to Bispecific T Cell Engager (BITE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Full length bispecific antibodies of the invention may be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope, i.e. an epitope on BCMA and an epitope on CD3.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Inti. Publ. No. WO 2006/028936) may be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob".

Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by the following substitutions (expressed as modified position in the first CH3 domain of the first heavy chain/modified position in the second CH3 domain of the second heavy chain): L351Y_F405AY407V/T394W, T366I_K392M_T394W/F405A_Y407V, T366L_K392M_T394W/F405A_Y407V, L351Y_Y407A/T366A_K409F, L351Y_Y407A/T366V K409F Y407A/T366A_K409F, or T350V_L351Y_F405A Y407V/T350V_T366L_K392L_T394W as described in U.S. Pat. Publ. No. US2012/0149876 or U.S. Pat. Publ. No. US2013/0195849.

In addition to methods described above, bispecific antibodies of the invention may be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in Inti. Pat. Publ. No. WO2011/131746. In the methods, the first monospecific bivalent antibody (e.g., anti-BCMA antibody) and the second monospecific bivalent antibody (e.g., anti-CD3 antibody) are engineered to have certain substitutions at the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing conditions. Exemplary reducing agents that may be used are 2-mercaptoethylamine (2-MEA), dithiothreitol (DTT), dithioerythritol (DTE), glutathione, tris (2-carboxyethyl)phosphine (TCEP), L-cysteine and beta-mercaptoethanol, preferably a reducing agent selected from the group consisting of: 2-mercaptoethylamine, dithiothreitol and tris (2-carboxyethyl)phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 may be used.

In addition to the described BCMA×CD3-multispecific antibodies, also provided are polynucleotide sequences capable of encoding the described BCMA×CD3-multispecific antibodies. Vectors comprising the described polynucleotides are also provided, as are cells expressing the BCMA×CD3-multispecific antibodies provided herein. Also described are cells capable of expressing the disclosed vectors. These cells may be mammalian cells (such as 293F cells, CHO cells), insect cells (such as Sf7 cells), yeast cells, plant cells, or bacteria cells (such as E. coli). The described antibodies may also be produced by hybridoma cells.

Therapeutic Composition and Methods of Treatment Using Multispecific Antibodies and Multispecific Antigen-Binding Fragments Thereof The BCMA bispecific antibodies discussed above, for example the BCMA×CD3 bispecific antibodies discussed above, are useful in therapy. In particular, the BCMA bispecific antibodies are useful in treating cancer. Also provided herein are therapeutic compositions for the treatment of a hyperproliferative disorder in a mammal which comprises a therapeutically effective amount of a multispecific antibody or multispecific antigen-binding fragment described herein and a pharmaceutically acceptable carrier. In preferred embodiments, the multispecific antibody is a BCMA×CD3-multispecific antibody as described herein, or a multispecific antigen-binding fragment thereof, and more preferably a BCMA×CD3-bispecific antibody as described herein, or a BCMA×CD3-bispecific antigen-binding fragment thereof. In one embodiment said pharmaceutical composition is for the treatment of a BCMA-expressing cancer, including (but not limited to) the following: BCMA-expressing B cell cancers, such as multiple myeloma (MM); and other cancers yet to be determined in which BCMA is expressed. Particular bispecific antibodies that may be used to treat cancer, such as hematological cancer, including the specific cancers discussed above, include antibodies BCMB69, BCMB117, BCMB123, BCMB128, BCMB129, BCMB176, or BCMB177 or CD3B219. One example of a useful bispecific antibody for treating cancer, such as hematological cancer, including these specific cancers is BCMB72.

The pharmaceutical compositions provided herein comprise: a) an effective amount of a multispecific antibody or antibody fragment of the present invention, and b) a pharmaceutically acceptable carrier, which may be inert or physiologically active. In preferred embodiments, the multispecific antibody is a BCMA×CD3-multispecific antibody as described herein, or a multispecific antigen-binding fragment thereof, and more preferably a BCMA×CD3-bispecific antibody as described herein, or a BCMA×CD3-bispecific antigen-binding fragment thereof. As used herein, the term "pharmaceutically acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as any combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH.about.7.4, containing or not containing about 1 mg/mL to 25 mg/mL human serum albumin, (2) 0.90% saline (0.9% w/v sodium chloride (NaCl)), and (3) 5% (w/v) dextrose; and may also contain an antioxidant such as tryptamine and a stabilizing agent such as Tween 20®.

The compositions herein may also contain a further therapeutic agent, as necessary for the particular disorder being treated. Preferably, the multispecific antibody or antibody fragment and the supplementary active compound will have complementary activities that do not adversely affect each other. In a preferred embodiment, the further therapeutic agent is cytarabine, an anthracycline, histamine dihydrochloride, or interleukin 2. In a preferred embodiment, the further therapeutic agent is a chemotherapeutic agent.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperinoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The multispecific antibody or antibody fragment may also be orally administered. As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

Also provided herein are methods for killing a BCMA+ cell by administering to a patient in need thereof a multispecific antibody which binds said BCMA and is able to recruit T cells to kill said BCMA+cell (i.e., T cell redirection). Any of the multispecific antibodies or antibody fragments of the invention may be used therapeutically. For example, in one embodiment the BCMA×CD3-multispecific antibody BCMB72 may be used therapeutically to treat cancer in a subject.

In a preferred embodiment, multispecific antibodies or antibody fragments of the invention are used for the treatment of a hyperproliferative disorder in a mammal. In a more preferred embodiment, one of the pharmaceutical compositions disclosed above, and which contains a multispecific antibody or antibody fragment of the invention, is used for the treatment of a hyperproliferative disorder in a mammal. In one embodiment, the disorder is a cancer. In particular, the cancer is a BCMA-expressing cancer, including (but not limited to) the following: BCMA-expressing B-cell cancers, such as multiple myeloma (MM); and other cancers yet to be determined in which BCMA is expressed. In preferred embodiments, the multispecific antibody is a BCMA×CD3-multispecific antibody as described herein, or a multispecific antigen-binding fragment thereof, and more preferably a BCMA×CD3-bispecific antibody as described herein, or a BCMA×CD3-bispecific antigen-binding fragment thereof.

Accordingly, the pharmaceutical compositions of the invention are useful in the treatment or prevention of a variety of cancers, including (but not limited to) the following: a BCMA-expressing cancer, including (but not limited to) the following: BCMA-expressing B cell cancers, such as acute multiple myeloma (MM); and other cancers yet to be determined in which BCMA is expressed.

Similarly, further provided herein is a method for inhibiting the growth of selected cell populations comprising contacting BCMA-expressing target cells, or tissue containing such target cells, with an effective amount of a multispecific antibody or antibody fragment of the present invention, either alone or in combination with other cytotoxic or therapeutic agents, in the presence of a peripheral blood mononuclear cell (PBMC). In preferred embodiments, the multispecific antibody is a BCMA×CD3-multispecific antibody as described herein, or a multispecific antigen-binding fragment thereof, and more preferably a BCMA×CD3-bispecific antibody as described herein, or a BCMA×CD3-bispecific antigen-binding fragment thereof. In a preferred embodiment, the further therapeutic agent is cytarabine, an anthracycline, histamine dihydrochloride, or interleukin 2. In a preferred embodiment, the further therapeutic agent is a chemotherapeutic agent. The method for inhibiting the growth of selected cell populations can be practiced in vitro, in vivo, or ex vivo.

Examples of in vitro uses include treatments of autologous bone marrow prior to their transplant into the same patient in order to kill diseased or malignant cells; treatments of bone marrow prior to its transplantation in order to kill competent T cells and prevent graft-versus-host-disease (GVHD); treatments of cell cultures in order to kill all cells except for desired variants that do not express the target antigen, or to kill variants that express undesired antigen. The conditions of non-clinical in vitro use are readily determined by one of ordinary skill in the art.

Examples of clinical ex vivo use are to remove tumor cells from bone marrow prior to autologous transplantation in cancer treatment. Treatment can be carried out as follows. Bone marrow is harvested from the patient or other individual and then incubated in medium containing serum to which is added the cytotoxic agent of the invention. Concentrations range from about 10 uM to 1 uM, for about 30 min to about 48 hr at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, a therapeutically effective amount of the multispecific antibody or antigen-binding fragment is administered to a subject in need thereof. For example, the BCMA×CD3-multispecific antibodies and multispecific antigen-binding fragments thereof may be useful in the treatment of a BCMA-expressing cancer in a subject in need thereof. In some embodiments, the BCMA-expressing cancer is a B-cell cancer, such as multiple myeloma (MM). In preferred embodiments, the multispecific antibody is a BCMA×CD3-multispecific antibody as described herein, or a multispecific antigen-binding fragment thereof, and more preferably a BCMA×CD3-bispecific antibody as described herein, or a BCMA×CD3-bispecific antigen-binding fragment thereof. In some embodiments, the subject is a mammal, preferably a human. In some embodiments, the multispecific antibody or antigen-binding fragment will be administered as a solution that has been tested for sterility.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the multispecific antibodies and fragments depend on the disease or condition to be treated and may be determined by one skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg.

A physician or veterinarian having ordinary skill in the art may readily determine and prescribe the effective amount of the pharmaceutical composition required. For example, the physician or veterinarian could start doses of the multispecific antibody or fragment employed in the pharmaceutical composition at levels lower than that required in order to achieve the desired therapeutic effect and gradually increase the dosage until the desired effect is achieved. In general, a suitable daily dose of a bispecific antibody of the present invention will be that amount of the compound which is the lowest dose effective to produce a therapeutic effect. Administration may e.g. be parenteral, such as intravenous, intramuscular or subcutaneous. In one embodiment, the multispecific antibody or fragment may be administered by infusion in a weekly dosage of calculated by mg/m$^2$. Such dosages can, for example, be based on the mg/kg dosages provided above according to the following: dose (mg/kg)× 70: 1.8. Such administration may be repeated, e.g., 1 to 8 times, such as 3 to 5 times. The administration may be performed by continuous infusion over a period of from 2 to 24 hr, such as of from 2 to 12 hr. In one embodiment, the multispecific antibody or fragment may be administered by slow continuous infusion over a long period, such as more than 24 hours, in order to reduce toxic side effects.

In one embodiment, the multispecific antibody or fragment may be administered in a weekly dosage of calculated as a fixed dose for up to eight times, such as from four to six times when given once a week. Such regimen may be repeated one or more times as necessary, for example, after six months or twelve months. Such fixed dosages can, for example, be based on the mg/kg dosages provided above, with a body weight estimate of 70 kg. The dosage may be determined or adjusted by measuring the amount of bispecific antibody of the present invention in the blood upon administration by for instance taking out a biological sample and using anti-idiotypic antibodies which target the BCMA antigen binding region of the multispecific antibodies of the present invention.

In one embodiment, the multispecific antibody or fragment may be administered by maintenance therapy, such as, e.g., once a week for a period of six months or more.

A multispecific antibody or fragment may also be administered prophylactically in order to reduce the risk of developing cancer, delay the onset of the occurrence of an event in cancer progression, and/or reduce the risk of recurrence when a cancer is in remission.

The multispecific antibodies and fragments thereof as described herein may also be administered in combination therapy, i.e., combined with other therapeutic agents relevant for the disease or condition to be treated. Accordingly, in one embodiment, the antibody-containing medicament is for combination with one or more further therapeutic agent, such as a chemotherapeutic agent. In some embodiments, the other therapeutic agent is cytarabine, an anthracycline, histamine dihydrochloride, or interleukin 2. Such combined administration may be simultaneous, separate or sequential, in any order. For simultaneous administration the agents may be administered as one composition or as separate compositions, as appropriate.

In one embodiment, a method for treating a disorder involving cells expressing BCMA in a subject, which method comprises administration of a therapeutically effective amount of a multispecific antibody or fragment, such as a BCMA×CD3 bispecific antibody described herein, and radiotherapy to a subject in need thereof is provided. In one embodiment is provided a method for treating or preventing cancer, which method comprises administration of a therapeutically effective amount of a multispecific antibody or fragment, such as a BCMA×CD3 antibody described herein, and radiotherapy to a subject in need thereof. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

Kits

Also provided herein are includes kits, e.g., comprising a described multispecific antibody or antigen-binding fragment thereof and instructions for the use of the antibody or fragemtn for killing of particular cell types. In preferred embodiments, the multispecific antibody is a BCMA×CD3-multispecific antibody as described herein, or a multispecific antigen-binding fragment thereof, and more preferably a BCMA×CD3-bispecific antibody as described herein, or a BCMA×CD3-bispecific antigen-binding fragment thereof. The instructions may include directions for using the multispecific antibody or antigen-binding fragment thereof in vitro, in vivo or ex vivo.

Typically, the kit will have a compartment containing the multispecific antibody or antigen-binding fragment thereof. The multispecific antibody or antigen-binding fragment thereof may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the multispecific antibody or antigen-binding fragment thereof prior to administering to a patient, and tools that aid in administering the multispecific antibody or antigen-binding fragment thereof to a patient.

Diagnostic Uses

The multispecific antibodies and fragments described herein may also be used for diagnostic purposes. Thus, also provided are diagnostic compositions comprising a multispecific antibody or fragments as defined herein, and to its use. In preferred embodiments, the multispecific antibody is a BCMA×CD3-multispecific antibody as described herein, or a multispecific antigen-binding fragment thereof, and more preferably a BCMA×CD3-bispecific antibody as described herein, or a BCMA×CD3-bispecific antigen-binding fragment thereof. In one embodiment, the present invention provides a kit for diagnosis of cancer comprising a container comprising a bispecific BCMA×CD3 antibody, and one or more reagents for detecting binding of the antibody to BCMA. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. For example, the multispecific antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

Exemplary Embodiments of the Described Subject Matter

To better and more fully describe the subject matter herein, this section provides enumerated exemplary embodiments of the subject matter presented.

Enumerated Embodiments:

1. A recombinant antibody, or an antigen-binding fragment thereof, that binds immunospecifically to BCMA, wherein the antibody has a heavy chain and a light chain, said heavy chain comprising:

a. a heavy chain complementarity determining region 1 (CDR1) having the amino acid sequence of SEQ ID NO: 4, a heavy chain CDR2 having the amino acid sequence of SEQ ID NO: 5, and a heavy chain CDR3 having the amino acid sequence of SEQ ID NO: 6;

b. a heavy chain CDR1 having the amino acid sequence of SEQ ID NO: 4, a heavy chain CDR2 having the amino acid sequence of SEQ ID NO: 5, and a heavy chain CDR3 having the amino acid sequence of SEQ ID NO: 6;

c. a heavy chain CDR1 having the amino acid sequence of SEQ ID NO: 7, a heavy chain CDR2 having the amino acid sequence of SEQ ID NO: 5, and a heavy chain CDR3 having the amino acid sequence of SEQ ID NO: 6;

d. a heavy chain CDR1 having the amino acid sequence of SEQ ID NO: 4, a heavy chain CDR2 having the amino acid sequence of SEQ ID NO: 5, and a heavy chain CDR3 having the amino acid sequence of SEQ ID NO: 19;

e. a heavy chain CDR1 having the amino acid sequence of SEQ ID NO: 4, a heavy chain CDR2 having the amino acid sequence of SEQ ID NO: 8, and a heavy chain CDR3 having the amino acid sequence of SEQ ID NO: 6;

f. a heavy chain CDR1 having the amino acid sequence of SEQ ID NO: 13, a heavy chain CDR2 having the amino acid sequence of SEQ ID NO: 5, and a heavy chain CDR3 having the amino acid sequence of SEQ ID NO: 19;

g. a heavy chain CDR1 having the amino acid sequence of SEQ ID NO: 13, a heavy chain CDR2 having the amino acid sequence of SEQ ID NO: 8, and a heavy chain CDR3 having the amino acid sequence of SEQ ID NO: 19.

2. The antibody, or antigen-binding fragment thereof, of embodiment 1, wherein said antibody further comprises a light chain CDR1 having the amino acid sequence of SEQ ID NO: 24, a light chain CDR2 having the amino acid sequence of SEQ ID NO: 25, and a light chain CDR3 having the amino acid sequence of SEQ ID NO: 26.

3. The antibody or antigen-binding fragment of embodiment 1, wherein the heavy chain of the antibody of (a) comprises the amino acid sequence of SEQ ID NO: 27; the heavy chain of the antibody of (b) comprises the amino acid sequence of SEQ ID NO: 57; the heavy chain of the antibody of (f) comprises the amino acid sequence of SEQ ID NO: 34; the heavy chain of the antibody of (k) comprises the amino acid sequence of SEQ ID NO: 39; the heavy chain of the antibody of (l) comprises the amino acid sequence of SEQ ID NO: 40; the heavy chain of the antibody of (m) comprises the amino acid sequence of SEQ ID NO: 58 or the heavy chain of the antibody of (n) comprises the amino acid sequence of SEQ ID NO: 43.

4. The antibody or antigen-binding fragment of embodiment 2 or embodiment 3, wherein the light chain of the antibody comprises the amino acid sequence of SEQ ID NO: 28.

5. The antibody or antigen-binding fragment of any one of embodiments 1 to 4 wherein the antibody or antigen-binding fragment thereof binds to the extracellular domain of human BCMA.

6. The antibody or antigen-binding fragment of any one of embodiments 1 to 5 wherein the antibody or antigen-binding fragment is a human antibody or antigen-binding fragment.

7. The antigen binding fragment of any one of embodiments 1 to 6 wherein the antigen binding fragment is a Fab fragment, a Fab2 fragment, or a single chain antibody.

8. The antibody or antigen-binding fragment of any one of embodiments 1 to 7 wherein the antibody or antigen-binding fragment thereof inhibits the interaction of BCMA and APRIL.

9. The antibody or antigen-binding fragment of embodiment 8, wherein the antibody or antigen-binding fragment exhibits an $IC_{50}$ for the interaction of BCMA and APRIL of about 5.9 nM as measured by ELISA.

10. The antibody or antigen-binding fragment of any one of embodiments 1 to 9 wherein the antibody or antigen-binding fragment thereof is an IgG.

11. The antibody or antigen-binding fragment of any one of embodiments 1 to 10 is an IgG4 isotype.

12. The antibody of embodiment 11 wherein the IgG4 has a S228P substitution, a L234A substitution and a L235A substitution in its Fc region.

13. The antibody or antigen-binding fragment of any one of embodiments 1 to 12 wherein the antibody or antigen-binding fragment thereof immunospecifically binds human BCMA and cross reacts to cynomolgus monkey BCMA.

14. The antibody or antigen-binding fragment of any one of embodiments 1 to 13 wherein the antibody or antigen-binding fragment thereof binds BCMA on the surface of human myeloma cells.

15. The antibody or antigen-binding fragment of any one of embodiments 1 to 14 wherein the antibody or antigen-binding fragment thereof binds BCMA on the surface of human multiple myeloma cells.

16. A recombinant cell expressing the antibody or antigen-binding fragment of any one of embodiments 1 to 15.

17. The cell of embodiment 16 wherein the cell is a hybridoma.

18. The cell of embodiment 16 wherein the antibody is recombinantly produced.

19. A recombinant BCMA×CD3 bispecific antibody or a BCMA×CD3 bispecific binding fragment thereof comprising:

a) a first heavy chain (HC1);

b) a second heavy chain (HC2);

c) a first light chain (LC1); and d) a second light chain (LC2), wherein HC1 is associated with LC1 and HC2 is associated with LC2 and wherein HC1 comprises SEQ ID NO: 59, SEQ ID NO: 60, and SEQ ID NO: 61 and LC1 comprises SEQ ID NO: 62, SEQ ID NO: 63, and SEQ ID NO: 64 to form a first antigen-binding site that immunospecifically binds CD3 and wherein HC2 comprises SEQ ID NO: 4, SEQ ID NO: 5, and SEQ ID NO: 6 a and LC2 comprises SEQ ID NO: 24, SEQ ID NO: 25, and SEQ ID NO: 26 to form a second antigen-binding site that immunospecifically binds BCMA.

20. A recombinant BCMA×CD3 bispecific antibody or fragment thereof of embodiment 19 comprising an HC1 comprising SEQ ID NO: 55, a LC1 comprising SEQ ID NO: 56, a HC2 comprising SEQ ID NO: 65, and a LC2 comprising: a) SEQ ID NO: 66 or b) SEQ ID NO: 76.

21. The BCMA×CD3 bispecific antibody or bispecific binding fragment of embodiment 20 wherein the antibody or bispecific binding fragment is an IgG.

22. The BCMA×CD3 bispecific antibody or bispecific binding fragment of any of embodiments 19, embodiment 20 or embodiment 21 wherein the antibody or bispecific binding fragment is IgG4 isotype.

23. The BCMA×CD3 bispecific antibody or bispecific binding fragment of embodiment 19 to 22 wherein the antibody or bispecific binding fragment immunospecifically binds human BCMA with an affinity of at least 0.22 nM as measured by surface plasmon resonance.

24. The BCMA×CD3 bispecific antibody or bispecific binding fragment of embodiments 19 to 23 wherein the antibody or bispecific binding fragment thereof binds BCMA on the surface of human myeloma cells.

25. The BCMA×CD3 bispecific antibody or bispecific binding fragment of embodiments 19 to 24 wherein the antibody or bispecific binding fragment thereof binds BCMA on the surface of human multiple myeloma cells.

26. The BCMA×CD3 bispecific antibody or bispecific binding fragment of embodiment 19 to 25 wherein the antibody or bispecific binding fragment induces human T-cell activation in vitro with an $EC_{50}$ of less than about 0.37 nM.

27. The BCMA×CD3 bispecific antibody or bispecific binding fragment of embodiment 19 to 26 wherein the antibody or bispecific binding fragment induces T-cell dependent cytotoxicity of BCMA-expressing cells in vitro with an $EC_{50}$ of less than about 0.45 nM.

28. The BCMA×CD3 bispecific antibody or bispecific binding fragment of embodiment 19 to 27 wherein the antibody or bispecific binding fragment is not a BCMA agonist.

29. The BCMA×CD3 bispecific antibody or bispecific binding fragment of embodiment 19 to 28 wherein the antibody or bispecific binding fragment does not alter NF-κB activation at concentrations below 10 nM.

30. A recombinant cell expressing the antibody or bispecific binding fragment of any one of embodiments 19 to 29.

31. The cell of embodiment 30 wherein the cell is a hybridoma.

32. A method for treating a subject having cancer, said method comprising administering a therapeutically effective amount of the BCMA×CD3 bispecific antibody or bispecific binding fragment of any one of embodiments 19 to 29 to a subject in need thereof for a time sufficient to treat the cancer.

33. A method for inhibiting growth or proliferation of cancer cells, said method comprising administering a therapeutically effective amount of the BCMA CD3 bispecific antibody or bispecific binding fragment of any one of embodiments 19 to 29 to inhibit the growth or proliferation of cancer cells.

34. A method of redirecting a T cell to a BCMA-expressing cancer cell, said method comprising administering a therapeutically effective amount of the BCMA×CD3 bispecific antibody or bispecific binding fragment of any one of embodiments 19 to 29 to redirect a T cell to a cancer.

35. The method of embodiment 32, 33, or 34 wherein the cancer is a hematological cancer.

36. The method of embodiment 35 wherein the hematological cancer is a BCMA-expressing B cell cancer.

37. The method of embodiment 36 wherein the BCMA-expressing B cell cancer is multiple myeloma.

38. The method of embodiment 32 further comprising administering a second therapeutic agent.

39. The method of embodiment 38 wherein the second therapeutic agent is a chemotherapeutic agent or a targeted anti-cancer therapy.

40. The method of embodiment 39 wherein the chemotherapeutic agent is cytarabine, an anthracycline, histamine dihydrochloride, or interleukin 2.

41. A pharmaceutical composition comprising the BCMA×CD3 bispecific antibody or bispecific binding fragment of any one of embodiments 19 to 29 and a pharmaceutically acceptable carrier.

42. A method for generating the BCMA×CD3 bispecific antibody or bispecific binding fragment of any one of embodiments 19 to 29 by culturing the cell of any one of embodiments 30 to 31.

43. An isolated synthetic polynucleotide encoding the HC1, the HC2, the LC1 or the LC2 of the BCMA×CD3 bispecific antibody or bispecific binding fragment of any one of embodiments 19 to 29.

44. A kit comprising the BCMA×CD3 bispecific antibody or bispecific binding fragment as defined in any one of embodiments 19 to 29 and/or a polynucleotide as defined in claim 44 and packaging for the same.

BRIEF DESCRIPTION OF THE DRAWINGS

(FIG. 2A) Overview of the epitope location. BCMB69 binds to the concave surface of BCMA (black regions). (FIG. 2B) Interaction map showing direct contacts between BCMA and BCMB69. Residues from all CDRs except CDR-L1 contact BCMA. Van der Waals interactions are shown as dashed lines, H-bonds are solid lines with arrows indicating backbone H bonds and pointing to the backbone atoms. BCMA residues that contact both BCMB69 and APRIL have a black frame. A distance cut-off of 4 Å was used to identify the contact residues (3.5 Å distance threshold for H bonds). (FIG. 2C and FIG. 2D) Close view of BCMA main interactions with the BCMB69 Light (FIG. 2C) and Heavy (FIG. 2D) Chains. H bonds are shown as dashed lines with the distances in Angstroms.

FIG. 3. Epitope and paratope residues of BCMB69. The epitope and paratope residues are shaded, the CDR regions are underlined (Kabat definition), and BCMA residues that differ from human are in bold italic. Only the BCMB69 Fab and extracellular BCMA sequences are shown.

FIG. 5. SPR data for BCMB72 demonstrates that the molecule has binding to human, cyno and mouse BCMA. The Average $K_D$ for cyno and mouse BCMA is about 36-fold and 402-fold, respectively when compared to human BCMA.

FIGS. 8A, 8B, SC, 8D and 8E. BCMB72-dependent T-cell activation in the presence of various MM cell lines. H929 (FIG. 8A), MM.1R (FIG. 8B), RPMI 8226 (FIG. 8C), U266 (FIG. 8D) and Mv4-11 (FIG. 8E) cells were subjected to the indicated antibodies in the presence of T cells from six normal donors (donor averages ±SEM are shown) and Fc blocker (2 mg/mL) for 48 hours. The $EC_{50}$ values are indicated on the graphs. Statistical analysis: In addition to the simple fact of model convergence, the width of the 95% confidence interval about the Log $EC_{50}$ are considered to evaluate adequacy of fit. (The confidence interval about Log $EC_{50}$ is used because it is symmetric; confidence intervals about the $EC_{50}$ itself are not.) An interval less than +/−2 (or a total 95% confidence interval width less than 4) is considered adequate.

FIGS. 9A and 9B. Summary of $EC_{50}$ and maximum T cell activation values from two independent experiments using T cells from multiple normal donors. Individual donor values and donor averages are shown for each cell line and for each experiment. No data=did not test; no fit=software unable to generate a curve; ~ values=approximation based on model extrapolation.

FIGS. 11A and 11B. Summary of $EC_{50}$ and maximum lysis values from two independent experiments using T cells from multiple normal donors. Individual donor values and donor averages are shown for each cell line and for each experiment. No data=did not test; no fit=software unable to generate a curve; ~ values=approximation based on model extrapolation.

FIG. 12B shows the T-cell activation, as assessed by CD25 upregulation on T-cell surface. In general, data points aligned tightly along the generated fit curve and there was little variability between T cell donors and the repeat studies.

FIG. 13. Summary of $EC_{50}$ values for BCMB72-mediated cytokine release. RPMI 8226 cell supernatants from the cytotoxicity experiments (see Example 12, FIG. 8) were collected and analyzed for six different cytokine levels using an MSD based multiplex assay. BCMB72 (BCMA×CD3) and control antibodies (BCMA×null and null×CD3) were used at various concentrations.

FIG. 14A indicates the cytotoxicity potential and FIG. 14B on the right side shows T-cell activation curves that were similar between the various lots of BCMB72.

(FIG. 16A and FIG. 16B), 24 hr. (FIG. 16C and FIG. 16D) and 48 hr (FIG. 16E and FIG. 16F) were analyzed. TNFα induced NF-kB activation in both HEK-NF-kB parent cells and HEK-NF-kB-BCMA cells, whereas, APRIL induction was seen only in BCMA specific cell type. BCMB72 has no effect on the parental cell line and showed activation only at high concentrations in BCMA-expressing cells.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1: Materials

BCMA ECD Molecules

Recombinant human (h) BCMA-Fc fusion protein (catalog #193-BC-050), corresponding to amino acid 1 to 54 of hBCMA (SEQ ID NO:1) and recombinant mouse (m) BCMA-Fc fusion protein (catalog#593-BC-050) corresponding to amino acid 1 to 49 of mBCMA (SEQ ID NO:2) was obtained from R&D Systems. Recombinant cyno BCMA protein prepared from cDNA obtained from gene synthesis techniques (U.S. Pat. No. 6,670,127, U.S. Pat. No. 6,521,427). All proteins were tested for endotoxin prior to use and were biotinylated for phage panning studies. These materials were also used for binding and affinity measurements.

Soluble human BCMA was obtained from AB Biosciences (Catalog no. P011Xp, lot no. 033-013) and was used for characterization studies.

APRIL, BAFF, BAFF-R and TACI Molecules

Soluble hAPRIL (catalog #DY884), hBAFF (catalog #2149-BF), hBAFF-R (catalog #1162-BR), corresponding to amino acids 7 to 71 of hBAFF-R, and hTAC1, corresponding to amino acids 2 to 166 of TACI were obtained from R&D Systems. BAFF-R and TAC1 were biotinylated for SPR studies.

Generation of BCMA Cell Lines

Figure 1A:
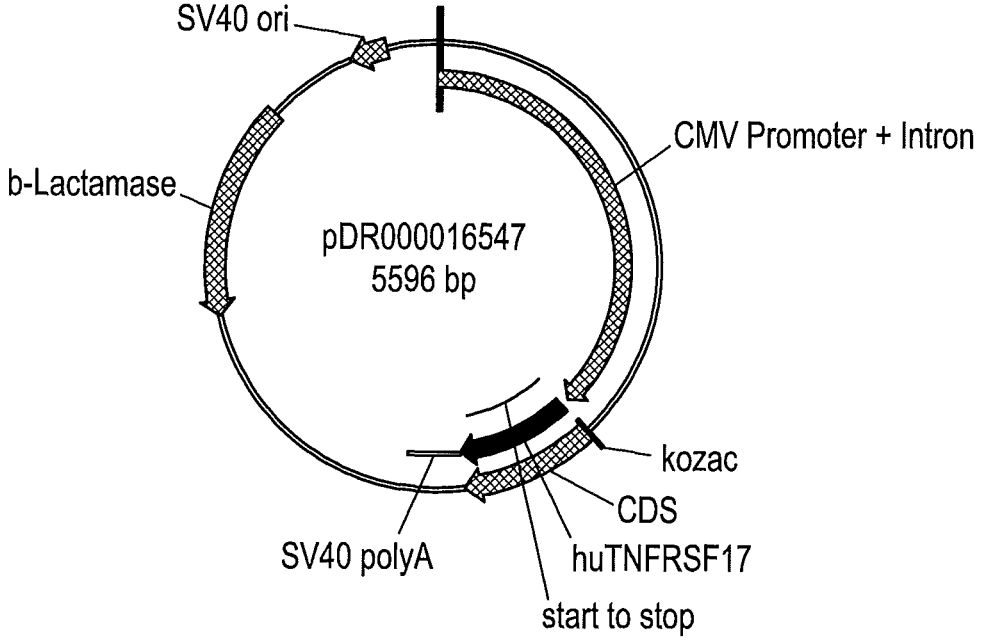
FIGS. 1A and 1B. Vectors used for cloning human BCMA (FIG. 1A) and cyno BCMA (FIG. 1B).
Figure 1B:
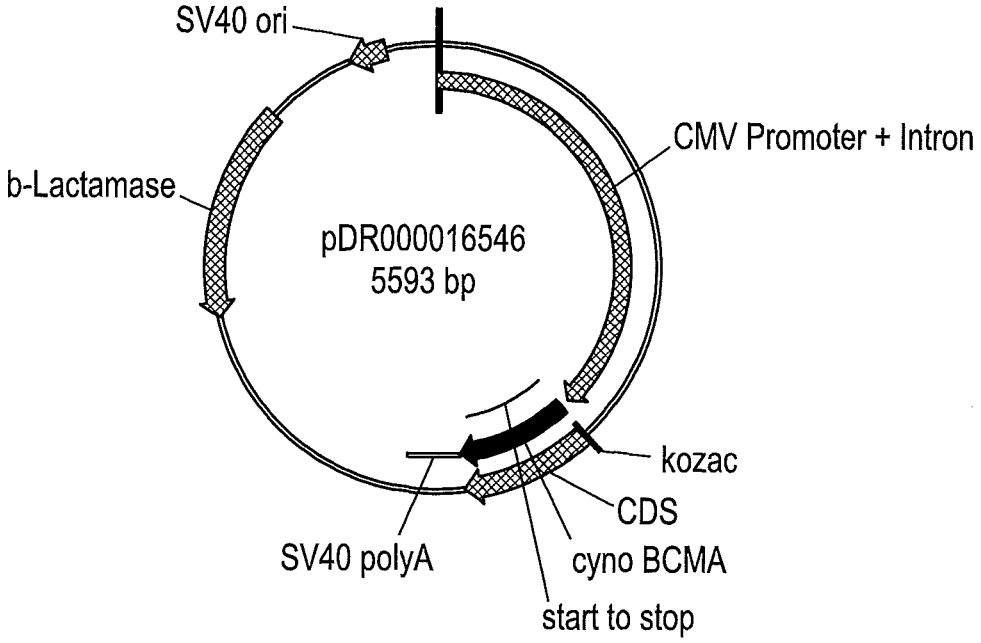
Figure 2A:
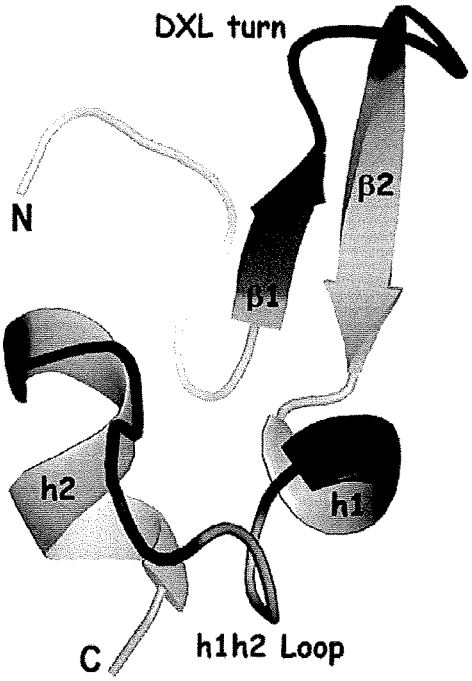
FIGS. 2A, 2B, 2C and 2D. BCMB69 epitope location and interactions between human BCMA and BCMB69.
Figure 2B:
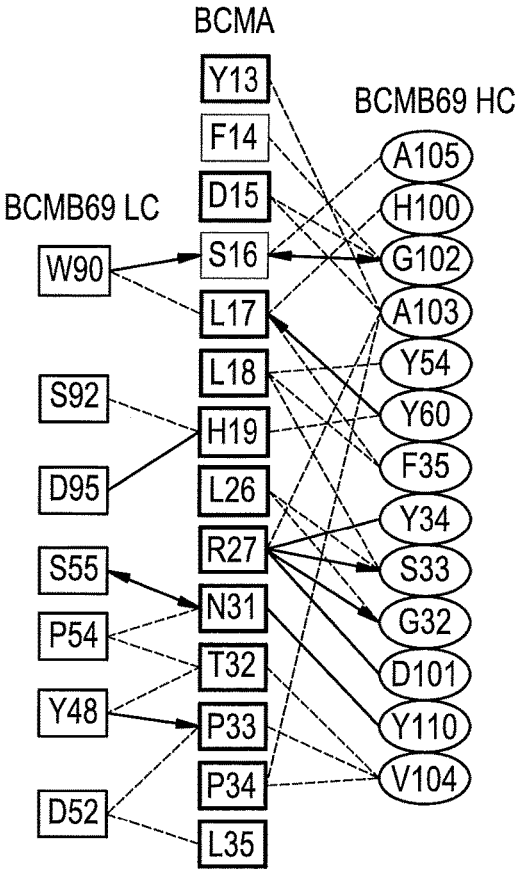
Figure 2C:
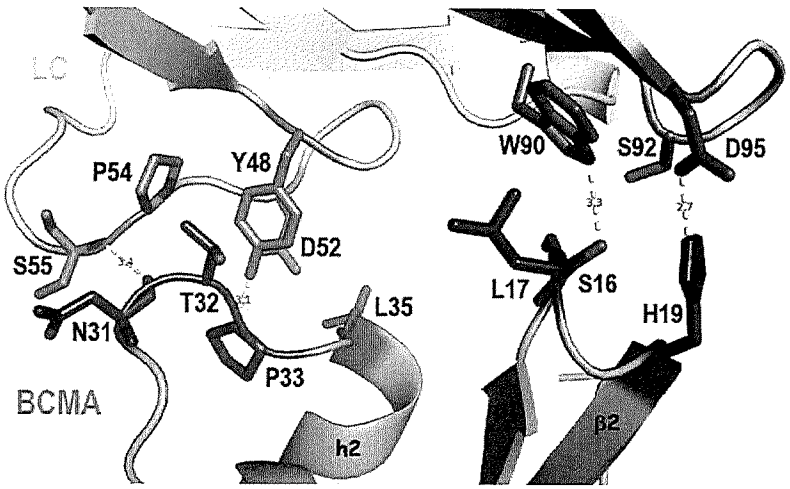
Figure 2D:
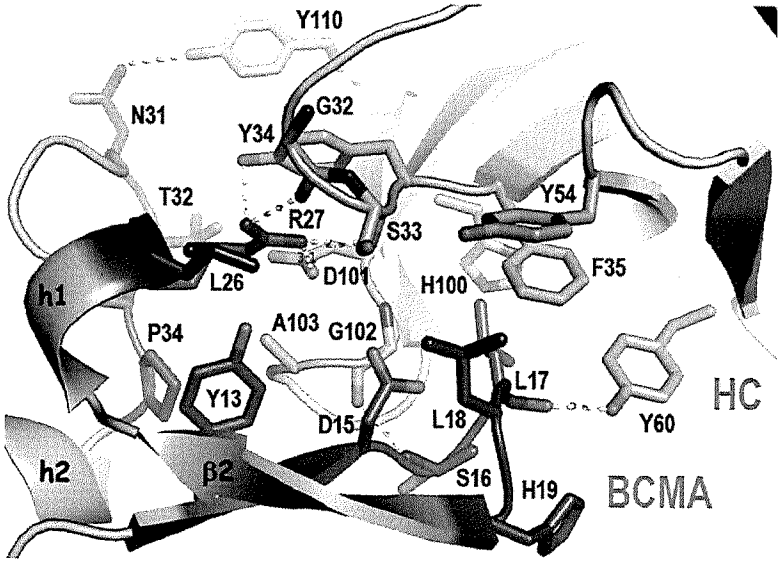

Vectors presenting human BCMA (FIG. 1A) and cyno BCMA (FIG. 1B) were transiently transfected into HEK293 expi cells using standard methods. Transfected 293F adherent cells were selected for stable plasmid integration, then single cell sorted and the BCMA surface receptor expression was quantified by FACS using an anti-human BCMA-PE labeled antibody (R&D Systems FAB 193P).

Example 2: Isolation of Human BCMA Monoclonal Antibody Expressing Hybridomas A human immunoglobulin transgenic rat strain (OmniRat®; OMT, Inc.) was used to develop human BCMA monoclonal antibody expressing hybridoma cells. The OmniRat® contains a chimeric human/rat IgH locus (comprising 22 human $V_H$s, all human D and $J_H$ segments in natural configuration linked to the rat $C_H$ locus) together with fully human IgL loci (12 Vκs linked to Jκ-Cκ and 16 Vλs linked to Jλ-Cλ). (see e.g., Osborn, et al. (2013) J Immunol 190(4): 1481-1490). Accordingly, the rats exhibit reduced expression of rat IgM or κ, and in response to immunization, the introduced human heavy and light chain transgenes undergo class switching and somatic mutation to generate high affinity human IgG monoclonal antibodies. The preparation and use of OmniRat®, and the genomic modifications carried by such rats, is described in PCT Publication WO 14/093908 to Bruggemann et al.

When immunized with recombinant human BCMA (rhBCMA), this transgenic rat produces human IgG antibodies specific to human BCMA.

The immunization scheme was performed as follows: six rats were immunized with hBCMA-Fc fusion. Following a 21 day immunization regimen, spleens and lymph nodes from the immunized rats were harvested and used to generate four total hybridomal libraries. The libraries were titrated and assayed by ELISA to identify mAbs which exhibited binding to biotinylated hBCMA. The mAbs were captured on an MSD Streptavidin plate. After further confirmatory screenings, hybridoma supernatants that exhibited binding specific to human BCMA and cyno BCMA were sequenced, cloned and expressed and converted to both human IgG1 and IgG4.

Example 3: Purification of BCMA Antibodies

The BCMA antibodies in the clarified culture supernatants were captured by MabSelect SuRe Protein A resin and eluted with 100 mM sodium acetate (pH 3.5). The fractions containing the antibodies were pooled and promptly neutralized with 2.5 M Tris HCl (pH 7.2), then buffer exchanged into 1×D-PBS or other desired buffers if specified. The protein concentration was determined by measurement of OD280 on a NanoDrop spectrophotometer and calculated using its absorbance coefficient. The purity and homogeneity of the antibody was assessed by SDS-PAGE and SE-HPLC. An SEC polishing step using Superdex 200 was performed if the monomer falls below 95% per SE-HPLC.

Example 4: Characterization of BCMA Antibodies
Cell Binding to BCMA

Binding of BCMA antibodies to engineered BCMA expressing cells and the cancer cell lines U2392, EJM, MMIR, U266, OPM2, and RPMI-18226 was assessed using a MSD (Mesoscale) cell binding assay and flow cytometry. The object of the screening assay was to identify antibodies that bound to cells expressing BCMA as well as cross reactivity with cells expressing cyno BCMA.

For MSD cell binding assay, cells were immobilized and BCMA antibody samples were assayed in triplicate. Briefly, expression supernatants of purified BCMA antibodies were normalized to 10 μg/mL. 5000 cells per well were plated into a 384 well plate (MA6000, cat. L21XB, MSD) and allowed to adhere for 2 hr. Cells were then blocked with 20% FBS in PBS (Gibco) for 15 mins. Antibody supernatants were then added and left at RT for 1 hr. Cells were washed 3 times with PBS and a ruthenium labeled secondary antibody (Jackson Immuno Research) was then added at 1 μg/mL and incubated for 1 hr at room temperature. A further washing step was then applied and 35 μL per well of MSD Read buffer T (surfactant free) was then added and incubated for 30 min for detection. Plates were then read using MSD Sector 6000. Data were normalized to controls and graphed using GraphPad Prism Version 5. A positive binder was determined to be a hit with a signal 3× greater than background. The assay was repeated for data consistency and top binders were selected for further development.

For flow cytometry, cells were incubated with a viability stain and 100,000 cells were added to a U bottom plate and centrifuged to pellet the cells. The titrated BCMA antibodies were added to the cells. After an incubation period, the cells were pelleted and washed. An AlexaFluor 647 labeled species specific secondary antibody was added to the cells and allowed to incubate. The cells were pelleted and washed several times. The cells were resuspended in an appropriate amount of running buffer and analyzed using a FACS CantoII. Cells were gated by FSC-A versus SSC-A for size, SSC-A versus SSC-H for singlets and for the viability stain. The geoMFI values of the live cell population was graphed and used to calculate $EC_{50}$ values if possible, i.e., if curves were fully sigmoidal.

Inhibition of APRIL Ligand-Binding

The BCMA antibody panel was screened in an APRIL binding competition ELISA. Soluble human April was purchased from R&D systems Catalog # DY884) the ability of anti-BCMA antibodies to block the binding of April to immobilized BCMA was evaluated.

Briefly, 96-well clear maxisorb plates were treated with 100 μL of 0.5 μg/mL of BCMA-ECD made in PBS and incubated at room temperature overnight. The plates were then washed three times with ELISA wash buffer containing 0.05% Tween-20 n PBS (R&D Systems Catalog # WA126), and then blocked with 300 L/well of Reagent Diluent containing 1% BSA5 in PBS (R&D Systems catalog # DY995).). For competitive binding, BCMA antibodies were added to the plate in 100 μL volumes and were incubated for 30 minutes before APRIL addition. After 30 minutes, 1 ng of APRIL was added per well and the plates were incubated overnight at 4° C. Unbound APRIL was washed with ELISA wash buffer and bound biotinylated APRIL was detected using SA-HRP conjugate at an optical density of 450 nm.

Example 5: Hit Evaluation and Selection

After completion of the characterization experiments, the antibody derived from the M2 hybridoma—named BCMB69—was determined to have the following characteristics:

- Binds to recombinant human BCMA
- Binds to recombinant cyno BCMA
- Exhibits weak binding to mouse BCMA
- Binds to both HEK-expressing human BCMA and HEK-expressing cyno BCMA as measured by flow cytometry
- Binds to human cancer lines that express BCMA (U2392, EJM, MMIR, U266, OPM2, and RPMI-18226)
- Blocks APRIL binding with an $IC_{50}$=5.9 nM As a result, BCMB69 (Table 4 and Table 5) was expressed and purified for the purpose of making BCMA×CD3 bispecific antibodies.

TABLE 4

CDR sequences of BCMB69 (relevant SEQ ID NO provided in parenthesis)

| ID | HC-CDR1 | HC-CDR2 | HC-CDR3 | LC-CDR1 | LC-CDR2 | LC-CDR3 |
|---|---|---|---|---|---|---|
| BCMB69 | SGSYFWG (4) | SIYYSGITYYNPSLKS (5) | HDGAVAGLFDY (6) | GGNNIGSKSVH (24) | DDSDRPS (25) | QVWDSSSDHVV (26) |

TABLE 5

$V_H$ and $V_L$ sequences of BCMB69

| mAb AA ID | VH Amino Acid Sequence | SEQ ID NO: | VL Amino Acid Sequence | SEQ ID NO: |
|---|---|---|---|---|
| BCMB69 | QLQLQESGPGLVKPSETLSL<br>TCTVSGGSISSGSYFWGWIR<br>QPPGKGLEWIGSIYYSGITY<br>YNPSLKSRVTISVDTSKNQF<br>SLKLSSVTAADTAVYYCARHD<br>GAVAGLFDYWGQGTLVTVS<br>SA | 27 | SYVLTQPPSVSVAPGQTA<br>RITCGGNNIGSKSVHWYQ<br>QPPGQAPVVVVYDDSDR<br>PSGIPERFSGGNTATL<br>TISRVEAGDEAVYYCQV<br>WDSSSDHVVFGGGTKLT<br>VL | 28 |

Example 6: Crystal Structure of an Anti-BCMA Fab

The crystal structure of one anti-BCMA antibody (BCMB69) was determined in free Fab form, as well as when bound to human BCMA, to characterize the antibody/antigen interactions in atomic details, increase our understanding of the antibody mechanism of action, and support any required antibody engineering efforts.

Materials

His-tagged BCMA Fab (SEQ ID NOs: 75 and 76; hereafter simply BCMB69 Fab) was expressed in HEK293 cells and purified using affinity and size-exclusion chromatographies. The Fab was received in 130 mM NaCl, 20 mM MES, pH 7.4.

Human BCMA extracellular region (residues 5-51 of SEQ ID NO: 1; hereafter simply BCMA) with a C-terminal His tag was expressed using the baculovirus system and purified by affinity and size-exclusion chromatography. The protein was received in 50 mM NaCl, 20 mM Tris pH 8.

Crystallization

BCMA/BCMB69 Fab Complex

The Fab/antigen complex was prepared by mixing BCMA with BCMB69 Fab at a molar ratio of 3.8:1 (excess BCMA) for about 16 h at 4° C. while buffer exchanging to 20 mM Hepes pH 7.5. The complex was then eluted from a monoS 5/50 column with a gradient of 51-63 mM NaCl in 20 mM Hepes pH 7.5 and concentrated to 17 mg/mL. Crystals suitable for X-ray diffraction were obtained from 25% PEG 3 kDa, 0.2M $MgCl_2$, 0.1M Mes pH 6.5 using the sitting drop vapor-diffusion method at 20° C. with micro-seeding.

BCMB69 Fab

The BCMB69 Fab was concentrated to 9 mg/mL without further purification. Crystals suitable for X-ray diffraction were obtained from 2M $(NH_4)_2SO_4$, 5% MPD, 0.1M Mes pH 6.5 using the sitting drop vapor-diffusion method at 20° C.

X-Ray Data Collection and Structure Determination

For X-ray data collection, the crystals were soaked for few seconds in a cryo-protectant solution containing the corresponding mother liquor supplemented with 20% glycerol and then, flash frozen in liquid nitrogen. X-ray diffraction data for the BCMA/BCMB69 complex was collected with a Rayonix 300HS CCD detector at beamline CMCF-08ID of the Canadian Light Source (CLS), while X-ray data for the free BCMB69 Fab was collected with a Dectris Pilatus 6M Pixel Array detector at beamline 17-ID of the Advanced Photon Source (APS) at Argonne National Laboratory. Diffraction data were processed with the program HKL (Otwinowski, Z. & Minor, W. (1997). Processing of X-ray diffraction data collected in oscillation mode. Methods in Enzymology 276: 307-326.).

The structures were solved by molecular replacement (MR) with Phaser (Read, R. J. (2001). Pushing the boundaries of molecular replacement with maximum likelihood. Acta Crystallogr D Biol Crystallogr 57: 1373-82). In the case of the free Fab structure, the search model for MR was the anti-influenza hemagglutinin 5j8 Fab (PDB code: 4M5Y). In the case of the BCMA/Fab complex, the search models for MR were the crystal structures of BCMA (PDB code: 1XU2) and the BCMB69 free Fab structure. The structures were refined with PHENIX (Adams, P. D., Gopal, K., Grosse-Kunstleve, R. W., Hung, L. W., Ioerger, T. R., McCoy, A. J., Moriarty, N. W., Pai, R. K., Read, R. J., Romo, T. D., Sacchettini, J. C., Sauter, N. K., Storoni, L. C. & Terwilliger, T. C. (2004). Recent developments in the PHENIX software for automated crystallographic structure determination. J Synchrotron Radiat 11: 53-5.) and model adjustments were carried out using COOT (Emsley P. & Cowtan, K. (2004). Coot: Model building tools for molecular graphics. Acta Crystallogr. D60: 2126-2132). All other crystallographic calculations were performed with the CCP4 suite of programs (Collaborative Computational Project Number 4, 1994). All molecular graphics were generated with PyMol (DeLano, W. (2002). The PyMOL molecular graphics system. Palo Alto, Calif., USA; Delano Scientific). The data statistics for both the BCMB69 free Fab structure and the complex are shown in Table 6.

TABLE 6

Crystallographic data for the BCMA/BCMB69 Fab complex and free BCMB69 Fab.

| | Complex | Free Fab |
|---|---|---|
| Structure ID in CBIS | PS41 | PS40 |
| Crystal data | | |
| Crystallization solution | | |
| 0.1M Buffer | Mes pH 6.5 | Mes pH 6.5 |
| Precipitant | 25% PEG 3 kDa | 2M $(NH_4)_2SO_4$ |
| Additive | 0.2M $MgCl_2$ | 5% MPD |
| Space group | $P2_1$ | $P2_12_12_1$ |
| Molecules/asymmetric unit | 2 | 1 |
| Unit cell | | |
| a, b, c (Å) | 62.9, 87.1, 88.7 | 64.3, 71.1, 123.0 |
| α, β, γ (°) | 90.0, 94.8, 90.0 | 90.0, 90.0, 90.0 |
| Solvent content (%) | 47 | 56 |
| X-ray data* | | |
| Resolution (Å) | 50.00-2.00 | 50.00-2.70 |
| Highest Resolution Shell (Å) | (2.07-2.00) | (2.75-2.70) |
| Measured reflections | 235,905 | 91,256 |

TABLE 6-continued

Crystallographic data for the BCMA/BCMB69 Fab complex and free BCMB69 Fab.

| | Complex | Free Fab |
|---|---|---|
| Completeness (%) | 99.9 (99.8) | 99.9 (99.9) |
| Redundancy | 3.7 (3.6) | 5.7 (4.8) |
| $R_{sym}$ (%) | 10.0 (52.7) | 14.8 (51.9) |
| <I/σ> | 13.3 (2.9) | 13.5 (3.1) |
| Refinement | | |
| Resolution (Å) | 45.4-2.0 | 34.2-2.7 |
| Number of reflections | 64,157 | 15,890 |
| Number of all atoms | 7,001 | 3,149 |
| Number of waters | 89 | 10 |
| $R_{work}/R_{free}$ (%) | 19.0/23.7 | 18.5/24.0 |
| Bond length RMSD (Å) | 0.009 | 0.004 |
| Bond angle RMSD (°) | 1.190 | 0.869 |
| Mean B-factor (Å$^2$) | 31.0 | 51.1 |
| MolProbity | | |
| Ramachandran favored (%) | 97.32 | 96.86 |
| Ramachandran allowed (%) | 2.68 | 2.90 |
| Ramachandran outliers (%) | 0.00 | 0.24 |
| Rotamer outliers (%) | 0.39 | 0.59 |
| Clash score | 3.20 | 1.96 |

The Epitope, Paratope and Interactions

Figure 4A:
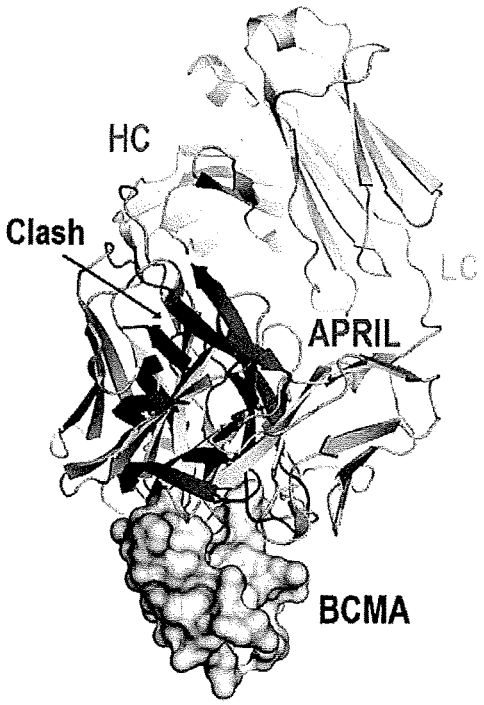
FIGS. 4A and 4B. Regions of clash between BCMB69 Fab and APRIL (FIG. 4A) and BCMB69 Fab BAFF (FIG. 4B). Structural overlay of BCMA/BCMB69 complex onto the BCMA/APRIL and BCMA/BAFF complexes showing regions of clash between the Fab and ligand. The solvent accessible surface of BCMA is displayed. The Fab and ligand molecules are shown as gray and black cartoons, respectively. The overlay was achieved by superposition of equivalent BCMA Ca atoms in both complexes (RMSD of 0.9 Å for APRIL complex and 1.2 Å for BAFF).
Figure 4B:
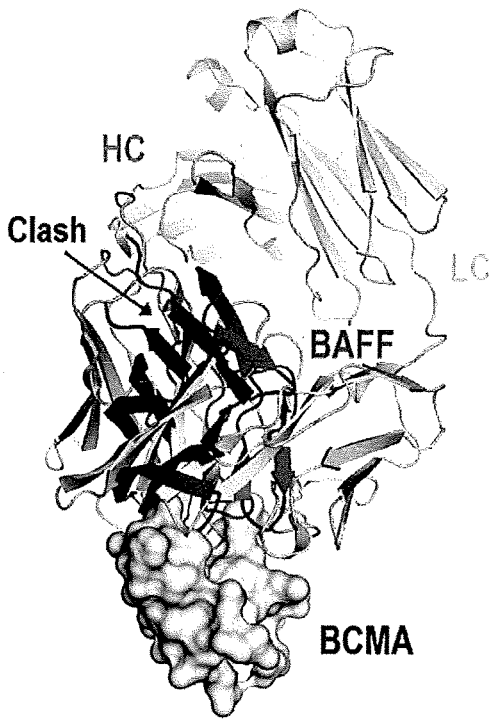

BCMB69 recognizes a conformational epitope composed of residues in the β-hairpin (residues Y13-H19) and helix-loop-helix (residues L26, R27, and N31-L35) regions of BCMA (FIGS. 3, 4A and 4B). The BCMB69 epitope comprises an area of about 830 Å$^2$ on BCMA and contains the ligand-binding DXL motif (residues D15-L18 in the type I turn of the β-hairpin), which protrudes into a shallow cavity lined by the antibody complementarity determining regions (CDRs). Leucine 17, at the tip of the DXL turn, is completely buried in the antibody cavity and has extensive interactions with BCMB69. Another prevalent epitope residue is Arg27, which is on the $3_{10}$-helix h1 and makes several hydrogen bond contacts with the heavy chain CDRs.

The BCMB69 paratope is composed of residues from all CDRs except CDR-L1 (FIGS. 2A, 2B, 2C, 2D and 3). The heavy chain has twice the number of contacts with BCMA compared to the light chain. Small side chains in the CDR-H3 loop tip (102-GAVAG-106) (SEQ ID NO: 77) facilitate CDR-H3 insertion into BCMA and establishment of extensive antibody/antigen contacts (40% of total contacts are made by CDR-H3). The BCMB69 CDRs pack onto a concave surface of the BCMA chair-like structure with CDR-L2 (residues Y48, D52, P54, S55), CDR-H1 (residues G32-Y34), and CDR-H3 (D101, A103, V104, Y110) contacting the "seat" formed by the h1 helix and h1h2 loop, while CDR-L3 (residues W90, S92, D95), CDR-H1 (F35), CDR-H2 (Y54, Y60), and CDR-H3 (H100, G102, A103, A105) interact with the "back" formed by the BCMA β-hairpin. Leu35, the only epitope residue in a "chair leg" (h2 helix), has van der Waals contacts with CDR-L2 residue D52.

BCMA has a small (about 50 residues) and compact extracellular domain. There is limited surface available for binding of non-competing antibodies or ligands to BCMA. Most of the BCMB69 epitope residues are also the binding residues for APRIL (12 out of 14 epitope residues) and BAFF (9 out of 14 residues). In the case of APRIL, which is BCMA highest affinity ligand, the only epitope residues not shared are F14 and S16 (FIG. 2B), while for BAFF the not-shared residues are F14, L26, T32, P33, and L35. The DXL loop is buried by both ligands and BCMB69.

Proposed Mechanisms of Action of BCMB69

BCMB69 is a candidate for redirection of T-cells to MM cancer cells. Killing of cancer cells mediated by a BCMB69×anti-CD3 bispecific antibody is not expected to be impaired by the structure and location of the BCMB69 epitope. The accessible location of the epitope allows binding of the BCMB69 Fab arm to the membrane-bound BCMA, while the other Fab arm is still bound to CD3 in the T-cell membrane.

BCMB69 can also disrupt the APRIL and BAFF signaling pathways in plasma cells through steric occlusion and direct competition for the BCMA binding site. The overlay of the BCMA/BCMB69 structure onto the BCMA/APRIL and BCMA/BAFF structures (Liu, Y., Hong, X., Kappler, J., Jiang, L., Zhang, R., Xu, L., Pan, C. H., Martin, W. E., Murphy, R. C., Shu, H. B., Dai, S. & Zhang, G. (2003). Nature 423: 49-56; Hymowitz, S. G., Patel, D. R., Wallweber, H. J. A., Runyon, S., Yan, M., Yin, J., Shriver, S. K., Gordon, N.C., Pan, B., Skelton, N. J., Kelley, R. F. & Starovasnik, M. A. (2005). J. Biol. Chem. 280: 7218-7227.) shows regions of clash between BCMB69 and APRIL, BAFF (FIG. 2B and FIGS. 4A and 4B), making it impossible for BCMA to bind simultaneously to antibody and natural ligand. APRIL and BAFF can signal using other receptors, such as TACI and BAFF-R, and BCMA knock-out mice are still viable. Therefore, blocking the APRIL and BAFF activity through BCMA occlusion may not be critically toxic for MM patients.

Example 7: Structure-Based Design of BCMB69 Mutants

Computational assessment of post-translational modification motifs and aggregation risk of the unbound BCMB69 variable domain reveals a medium risk of isomerization for the D101-G102 residues (CDR-H3) and a 486 Å$^2$ hydrophobic patch in the CDR region that might pose an aggregation risk. The most exposed hydrophobic residues in the patch are 158 (CDR-H2), F35 (CDR-H1), and V104 (CDR-H3; V104 was relevant in the Fv homology model, but not in the Fab crystal structure). To remove the isomerization and aggregation risks in the BCMB69 variable domain, various mutations were rationally designed (Table 7).

TABLE 7

Panel of BCMB69 mutants

| Set | Clone ID | Mutation | Goal |
|---|---|---|---|
| 1 | BCMB117 | G152A$^L$ | Remove isomerization and decrease hydrophobicity |
| 1 | BCMB118 | G102A$^H$, F35Y$^H$, V104T$^H$ | Remove isomerization and decrease hydrophobicity |
| 1 | BCMB119 | D101E$^H$, F35Y$^H$, V104T$^H$ | Remove isomerization and decrease hydrophobicity |
| 1 | BCMB120 | D101S$^H$, F35Y$^H$, V104T$^H$ | Remove isomerization and decrease hydrophobicity |
| 1 | BCMB121 | G32S$^H$, F35Y$^H$, I58S$^H$, P37K$^L$, V44L$^L$, V83D$^L$ | VH and VL germline mutations to decrease hydrophobicity |
| 1 | BCMB122 | G32S$^H$, F35Y$^H$, I58S$^H$ | VH germline mutations to decrease hydrophobicity |
| 1 | BCMB123 | G32S$^H$ | Access effect of single mutation, decrease hydrophobicity |

TABLE 7-continued

Panel of BCMB69 mutants

| Set | Clone ID | Mutation | Goal |
|---|---|---|---|
| 1 | BCMB124 | F35Y$^{H}$ | Access effect of single mutation, decrease hydrophobicity |
| 1 | BCMB125 | D101E$^{H}$ | Access effect of single mutation, remove isomerization |
| 1 | BCMB126 | D101S$^{H}$ | Access effect of single mutation, remove isomerization |
| 1 | BCMB127 | G102A$^{H}$ | Access effect of single mutation, remove isomerization |
| 1 | BCMB128 | V104T$^{H}$ | Access effect of single mutation, decrease hydrophobicity |
| 1 | BCMB129 | I58S$^{H}$ | Access effect of single mutation, decrease hydrophobicity |
| 1 | BCMB130 | G102A$^{H}$, F35Y$^{H}$, I58S$^{H}$ | Remove isomerization and decrease hydrophobicity |
| 1 | BCMB131 | D101E$^{H}$, F35Y$^{H}$, I58S$^{H}$ | Remove isomerization and decrease hydrophobicity |
| 2 | BCMB176 | G32S$^{H}$, V104T$^{H}$, G152A$^{L}$ | VH and VL germline mutations to Decrease hydrophobicity |
| 2 | BCMB177 | I58R$^{H}$, G32S$^{H}$, V104T$^{H}$, G152A$^{L}$ | VH and VL germline mutations to Decrease hydrophobicity |
| 2 | BCMB178 | I58W$^{H}$, G32S$^{H}$, V104T$^{H}$, G152A$^{L}$ | VH and VL germline mutations to decrease hydrophobicity |
| 2 | BCMB179 | D101Q$^{H}$, G32S$^{H}$, V104T$^{H}$, G152A$^{L}$ | Disrupt Isomerization and hydrophobicity, |
| 2 | BCMB180 | D101H$^{H}$, G32S$^{H}$, V104T$^{H}$, G152A$^{L}$ | Disrupt isomerization and hydrophobicity |
| 2 | BCMB181 | D101W$^{H}$, G32S$^{H}$, V104T$^{H}$, G152A$^{L}$ | VH and VL germline mutations to decrease hydrophobicity and Remove isomerization |
| 2 | BCMB182 | D101Y$^{H}$, G32S$^{H}$, V104T$^{H}$, G152A$^{L}$ | VH and VL germline mutations to decrease hydrophobicity and Remove isomerization |
| 2 | BCMB183 | I58R$^{H}$, D101Q$^{H}$, G32S$^{H}$, V104T$^{H}$, G152A$^{L}$ | VH and VL germline mutations to decrease hydrophobicity and Remove isomerization |
| 2 | BCMB184 | I58R$^{H}$, D101H$^{H}$, G32S$^{H}$, V104T$^{H}$, G152A$^{L}$ | VH and VL germline mutations to decrease hydrophobicity and Remove isomerization |
| 2 | BCMB185 | I58R$^{H}$, D101Y$^{H}$, G32S$^{H}$, V104T$^{H}$, G152A$^{L}$ | VH and VL germline mutations to decrease hydrophobicity and Remove isomerization |
| 2 | BCMB186 | I58W$^{H}$, D101Q$^{H}$, G32S$^{H}$, V104T$^{H}$, G152A$^{L}$ | VH and VL germline mutations to decrease hydrophobicity and Remove isomerization |
| 2 | BCMB187 | I58W$^{H}$, D101H$^{H}$, G32S$^{H}$, V104T$^{H}$, G152A$^{L}$ | VH and VL germline mutations to decrease hydrophobicity and Remove isomerization |
| 2 | BCMB188 | I58W$^{H}$, D101Y$^{H}$, G32S$^{H}$, V104T$^{H}$, G152A$^{L}$ | VH and VL germline mutations to decrease hydrophobicity and Remove isomerization |

The CDR sequences and the VH and VL sequences for the structure-based BCMB69 mutants are depicted in Tables 8 and 9 respectively.

TABLE 8

CDR Sequences of BCMB69 mutants (relevant SEQ ID NO provided in parenthesis)

| ID | HC-CDR1 | HC-CDR2 | HC-CDR3 | LC-CDR1 | LC-CDR2 | LC-CDR3 |
|---|---|---|---|---|---|---|
| BCMB117 | SGSYFWG (4) | SIYYSGITYYNPSLKS (5) | H**DG**AVAGLFDY (6) | GGNNIGSKSVH (24) | DDSDRPS (25) | QVWDSSSDHVV (26) |
| BCMB118 | SGSYFWG (4) | SIYYSGITYYNPSLKS (5) | HDAATAGLEDY (9) | GGNNIGSKSVH (24) | DDSDRPS (25) | QVWDSSSDHVV (26) |
| BCMB119 | SGSYFWG (4) | SIYYSGITYYNPSLKS (5) | HEGATAGLFDY (12) | GGNNIGSKSVH (24) | DDSDRPS (25) | QVWDSSSDHVV (26) |
| BCMB120 | SGSYFWG (4) | SIYYSGITYYNPSLKS (5) | HSGATAGLFDY ((5) | GGNNIGSKSVH (24) | DDSDRPS (25) | QVWDSSSDHVV (26) |
| BCMB121 | SSSYYWG (7) | SIYYSGSTYYNPSLKS (8) | H**DG**AVAGLFDY (6) | GGNNIGSKSVH (24) | DDSDRPS (25) | QVWDSSSDHVV (26) |
| BCMB122 | SSSYYWG (7) | SIYYSGSTYYNPSLKS (8) | H**DG**AVAGLFDY (6) | GGNNIGSKSVH (24) | DDSDRPS (25) | QVWDSSSDHVV (26) |
| BCMB123 | SSSYYWG (7) | SIYYSGITYYNPSLKS (5) | H**DG**AVAGLFDY (6) | GGNNIGSKSVH (24) | DDSDRPS (25) | QVWDSSSDHVV (26) |
| BCMB124 | SGSYYWG (10) | SIYYSGITYYNPSLKS (5) | H**DG**AVAGLFDY (6) | GGNNIGSKSVH (24) | DDSDRPS (25) | QVWDSSSDHVV (26) |
| BCMB125 | SGSYFWG (4) | SIYYSGITYYNPSLKS (5) | HEGAVAGLFDY (16) | GGNNIGSKSVH (24) | DDSDRPS (25) | QVWDSSSDHVV (26) |
| BCMB126 | SGSYFWG (4) | SIYYSGITYYNPSLKS (5) | HSGAVAGLEDY (17) | GGNNIGSKSVH (24) | DDSDRPS (25) | QVWDSSSDHVV (26) |
| BCMB127 | SGSYFWG (4) | SIYYSGITYYNPSLKS (5) | HDAAVAGLFDY (18) | GGNNIGSKSVH (24) | DDSDRPS (25) | QVWDSSSDHVV (26) |

TABLE 8-continued

CDR Sequences of BCMB69 mutants (relevant SEQ ID NO provided in parenthesis)

| ID | HC-CDR1 | HC-CDR2 | HC-CDR3 | LC-CDR1 | LC-CDR2 | LC-CDR3 |
|---|---|---|---|---|---|---|
| BCMB128 | SGSYFWG (4) | SIYYSGITYYNPSLKS (5) | HDGATAGLFDY (19) | GGNNIGSKSVH (24) | DDSDRPS (25) | QVWDSSSDHVV (26) |
| BCMB129 | SGSYFWG (4) | SIYYSGSTYYNPSLKS (8) | H**DG**AVAGLFDY (6) | GGNNIGSKSVH (24) | DDSDRPS (25) | QVWDSSSDHVV (26) |
| BCMB130 | SGSYYWG (10) | SIYYSGSTYYNPSLKS (8) | HDAAVAGLFDY (18) | GGNNIGSKSVH (24) | DDSDRPS (25) | QVWDSSSDHVV (26) |
| BCMB131 | SGSYYWG (10) | SIYYSGSTYYNPSLKS (8) | HEGAVAGLFDY (16) | GGNNIGSKSVH (24) | DDSDRPS (25) | QVWDSSSDHVV (26) |
| BCMB176 | SSSYFWG (13) | SIYYSGITYYNPSLKS (5) | HDGATAGLFDY (19) | GGNNIGSKSVH (24) | DDSDRPS (25) | QVWDSSSDHVV (26) |
| BCMB177 | SSSYFWG (13) | SIYYSGSTYYNPSLKS (8) | HDGATAGLFDY (19) | GGNNIGSKSVH (24) | DDSDRPS (25) | QVWDSSSDHVV (26) |
| BCMB178 | SSSYFWG (13) | SIYYSGWTYYNPSLKS (11) | HDGATAGLFDY (19) | GGNNIGSKSVH (24) | DDSDRPS (25) | QVWDSSSDHVV (26) |
| BCMB179 | SSSYFWG (13) | STYYSGITYYNPSLKS (5) | HQGATAGLFDY (20) | GGNNIGSKSVH (24) | DDSDRPS (25) | QVWDSSSDHVV (26) |
| BCMB180 | SSSYFWG (13) | SIYYSGITYYNPSLKS (5) | HHGATAGLFDY (21) | GGNNIGSKSVH (24) | DDSDRPS (25) | QVWDSSSDHVV (26) |
| BCMB181 | SSSYFWG (13) | SIYYSGITYYNPSLKS (5) | HWGATAGLFDY (22) | GGNNIGSKSVH (24) | DDSDRPS (25) | QVWDSSSDHVV (26) |
| BCMB182 | SSSYFWG (13) | SIYYSGITYYNPSLKS (5) | HYGATAGLFDY (23) | GGNNIGSKSVH (24) | DDSDRPS (25) | QVWDSSSDHVV (26) |
| BCMB183 | SSSYFWG (13) | SIYYSGRTYYNPSLKS (14) | HQGATAGLFDY (20) | GGNNIGSKSVH (24) | DDSDRPS (25) | QVWDSSSDHVV (26) |
| BCMB184 | SSSYFWG (13) | SIYYSGRTYYNPSLKS (14) | HHGATAGLFDY (21) | GGNNIGSKSVH (24) | DDSDRPS (25) | QVWDSSSDIAVV (26) |
| BCMB185 | SSSYFWG (13) | STYYSGRTYYNPSLKS (14) | HYGATAGLFDY (23) | GGNNIGSKSVH (24) | DDSDRPS (25) | QVWDSSSDIFVV (26) |
| BCMB186 | SSSYFWG (13) | SIYYSGWTYYNPSLKS (11) | HQGATAGLFDY (20) | GGNNIGSKSVH 24) | DDSDRPS (25) | QVWDSSSDHVV (26) |
| BCMB187 | SSSYFWG (13) | SIYYSGWTYYNPSLKS (11) | HHGATAGLFDY (21) | GGNNIGSKSVH (24) | DDSDRPS (25) | QVWDSSSDHVV (26) |
| BCMB188 | SSSYFWG (13) | SIYYSGWTYYNPSLKS (11) | HYGATAGLFDY (23) | GGNNIGSKSVH (24) | DDSDRPS (25) | QVWDSSSDHVV (26) |

TABLE 9

Vh and Vl sequences of BCMB69 mutants

| mAb AA ID | VH Amino Acid Sequence | SEQ ID NO: | VL Amino Acid Sequence | SEQ ID NO: |
|---|---|---|---|---|
| BCBM117 | QLQLQESGPGLVKPSETLSL TCTVSGGSISSGSYFWGWIR QPPGKGLEWIGSIYYSGITYY NPSLKSRVTISVDTSKNQFSL KLSSVTAADTAVYYCARH DGAVAGLFDYWGQGTLVT VSSA | 57 | SYVLTQPPSVSVAPGQTA RITCGGNNIGSKSVHWYQ QPPGQAPVVVVYDDSDR PSGIPERFSGSNSGNTATL TISRVEAGDEAVYYCQV WDSSSDHVVFGGGTKLT VL | 28 |
| BCBM118 | QLQLQESGPGLVKPSETLSL TCTVSGGSISSGSYYWGWIR QPPGKGLEWIGSIYYSGITYY NPSLKSRVTISVETSKNQFSL KLSSVTAADTAVYYCARHD AATAGLFDYWGQGTLVTVS SA | 29 | SYVLTQPPSVSVAPGQTA RITCGGNNIGSKSVHWYQ QPPGQAPVVVVYDDSDR PSGIPERFSGSNSGNTATL TISRVEAGDEAVYYCQV WDSSSDHVVFGGGTKLT VL | 28 |

TABLE 9-continued

Vh and Vl sequences of BCMB69 mutants

| mAb AA ID | VH Amino Acid Sequence | SEQ ID NO: | VL Amino Acid Sequence | SEQ ID NO: |
|---|---|---|---|---|
| BCBM119 | QLQLQESGPGLVKPSETLSL<br>TCTVSGGSISSGSYYWGWIR<br>QPPGKGLEWIGSIYYSGITYY<br>NPSLKSRVTISVDTSKNQFSL<br>KLSSVTAADTAVYYCARHE<br>GATAGLFDYWGQGTLVTVS<br>SA | 31 | SYVLTQPPSVSVAPGQTA<br>RITCGGNNIGSKSVHWYQ<br>QPPGQAPVVVVYDDSDR<br>PSGIPERFSGSNSGNTATL<br>TISRVEADGEAVYYCQV<br>WDSSSDHVVFGGGTKLT<br>VL | 28 |
| BCBM120 | QLQLQESGPGLVKPSETLSL<br>TCTVSGGSISSGSYYWGWIR<br>QPPGKGLEWIGSIYYSGITYY<br>NPSLKSRVTISVDTSKNQFSL<br>KLSSVTAADTAVYYCARHS<br>GATAGLFDYWGQGTLVTVS<br>SA | 32 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM121 | QLQLQESGPGLVKPSETLSL<br>TCTVSGGSISSSSYYWGWIR<br>QPPGKGLEWIGSIYYSGSTY<br>YNPSLKSRVTISVDTSKNQFS<br>LKLSSVTAADTAVYYCARH<br>DGAVAGLFDYWGQGTLVT<br>VSSA | 33 | SYVLTQPPSVSVAPGQTA<br>RITCGGNNIGSKSVHWYQ<br>QKPGQAPVLVVYDDSDR<br>PSGIPERFSGSNSGNTATL<br>TISRVEAGDEADYYCQV<br>WDSSSDHVVFGGGTKLT<br>VL | 30 |
| BCBM122 | QLQLQESGPGLVKPSETLSL<br>TCTVSGGSISSSSYYWGWIR<br>QPPGKGLEWIGSIYYSGSTY<br>YNPSLKSRVTISVDTSKNQFS<br>LKLSSVTAADTAVYYCARH<br>DGAVAGLFDYWGQGTLVT<br>VSSA | 33 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM123 | QLQLQESGPGLVKPSETLSL<br>TCTVSGGSISSSSYFWGWIR<br>QPPGKGLEWIGSIYYSGITYY<br>NPSLKSRVTISVDTSKNQFSL<br>KLSSVTAADTAVYYCARHD<br>GAVAGLFDYWGQGTLVTVS<br>SA | 34 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM124 | QLQLQESGPGLVKPSETLSL<br>TCTVSGGSISSGSYYWGWIR<br>QPPGKGLEWIGSIYYSGITYY<br>NPSLKSRVTISVDTSKNQFSL<br>KLSSVTAADTAVYYCARHD<br>GAVAGLFDYWGQGTLVTVS<br>SA | 35 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM125 | QLQLQESGPGLVKPSETLSL<br>TCTVSGGSISSGSYFWGWIR<br>QPPGKGLEWIGSIYYSGITYY<br>NPSLKSRVTISVDTSKNQFSL<br>KLSSVTAADTAVYYCARHE<br>GAVAGLFDYWGQGTLVTVS<br>SA | 36 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM126 | QLQLQESGPGLVKPSETLSL<br>TCTVSGGSISSGSYFWGWIR<br>QPPGKGLEWIGSIYYSGITYY<br>NPSLKSRVTISVDTSKNQFSL<br>KLSSVTAADTAVYYCARHS<br>GAVAGLFDYWGQGTLVTVS<br>SA | 37 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM127 | QLQLQESGPGLVKPSETLSL<br>TCTVSGGSISSGSYFWGWIR<br>QPPGKGLEWIGSIYYSGITYY<br>NPSLKSRVTISVDTSKNQFSL<br>KLSSVTAADTAVYYCARHD<br>AAVAGLFDYWGQGTLVTVS<br>SA | 38 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM128 | QLQLQESGPGLVKPSETLSL<br>TCTVSGGSISSGSYFWGWIR | 39 | SYVLTQPPSVSVAPGQTA<br>RITCGGNNIGSKSNGWYQ | 28 |

TABLE 9-continued

Vh and Vl sequences of BCMB69 mutants

| mAb AA ID | VH Amino Acid Sequence | SEQ ID NO: | VL Amino Acid Sequence | SEQ ID NO: |
|---|---|---|---|---|
| | QPPGKGLEWIGSIYYSGITYY<br>NPSLKSRVTISVDTSKNQFSL<br>KLSSVTAADTAVYYCARHD<br>GATAGLFDYWGQGTLVTVS<br>SA | | QPPGQAPVVVVYDDSDR<br>PSGIPERFSGSNSGNTATL<br>TISRVEAGDEAVYYCQV<br>WDSSSDHVVFGGGTKLT<br>VL | |
| BCBM129 | QLQLQESGPGLVKPSETLSL<br>TCTVSGGSISSGSYFWGWIR<br>QPPGKGLEWIGSIYYSGSTY<br>YNPSLKSRVTISVDTSKNQFS<br>LKLSSVTAADTAVYYCARH<br>DGAVAGLFDYWGQGTLVT<br>VSSA | 40 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM130 | QLQLQESGPGLVKPSETLSL<br>TCTVSGGSISSGSYYWGWIR<br>QPPGKGLEWIGSIYYSGSTY<br>YNPSLKSRVTISVDTSKNQFS<br>LKLSSVTAADTAVYYCARH<br>DAAVAGLFDYWGQGTLVT<br>VSSA | 41 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM131 | QLQLQESGPGLVKPSETLSL<br>TCTVSGGSISSGSYYWGWIR<br>QPPGKGLEWIGSIYYSGSTY<br>YNPSLKSRVTISVDTSKNQFS<br>LKLSSVTAADTAVYYCARH<br>EGAVAGLFDYWGQGTLVTV<br>SSA | 42 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM176 | QLQLQESGPGLVKPSETLSL<br>TCTVSGGSISSSSYFWGWIR<br>QPPGKGLEWIGSIYYSGITYY<br>NPSLKSRVTISVDTSKNQFSL<br>KLSSVTAADTAVYYCARH<br>DGATAGLFDYWGQGTLVTV<br>SSA | 58 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM177 | QLQLQESGPGLVKPSETLSL<br>TCTVSGGSISSSSYFWGWIR<br>QPPGKGLEWIGSIYYSGRTY<br>YNPSLKSRVTISVDTSKNQFS<br>LKLSSVTAADTAVYYCARH<br>DGATAGLFDYWGQGTLVTV<br>SSA | 43 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM178 | QLQLQESGPGLVKPSETLSL<br>TCTVSGGSISSSSYFWGWIR<br>QPPGKGLEWIGSIYYSGWTY<br>YNPSLKSRVTISVDTSKNQFS<br>LKLSSVTAADTAVYYCARH<br>DGATAGLFDYWGQGTLVTV<br>SSA | 44 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM179 | QLQLQESGPGLVKPSETLSL<br>TCTVSGGSISSSSYFWGWIR<br>QPPGKGLEWIGSIYYSGITYY<br>NPSLKSRVTISVDTSKNQFSL<br>KLSSVTAADTAVYYCARHQ<br>GATAGLFDYWGQGTLVTVS<br>SA | 45 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM180 | QLQLQESGPGLVKPSETLSL<br>TCTVSGGSISSSSYFWGWIR<br>QPPGKGLEWIGSIYYSGITYY<br>NPSLKSRVTISVDTSKNQFSL<br>KLSSVTAADTAVYYCARHH<br>GATAGLFDYWGQGTLVTVS<br>SA | 46 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM181 | QLQLQESGPGLVKPSETLSL<br>TCTVSGGSISSSSYFWGWIR<br>QPPGKGLEWIGSIYYSGITYY<br>NPSLKSRVTISVDTSKNQFSL<br>KLSSVTAADTAVYYCARHW | 47 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV | 28 |

TABLE 9-continued

Vh and Vl sequences of BCMB69 mutants

| mAb AA ID | VH Amino Acid Sequence | SEQ ID NO: | VL Amino Acid Sequence | SEQ ID NO: |
|---|---|---|---|---|
| | KLSSVTAADTAVYYCARHW<br>GATAGLFDYWGQGTLVTVS<br>SA | | WDSSSDHVVFGGGTKLT<br>VL | |
| BCBM182 | QLQLQESGPGLVKPSETLSL<br>TCTVSGGSISSSSYFWGWIR<br>QPPGKGLEWIGSIYYSGITYY<br>NPSLKSRVTISVDTSKNQFSL<br>KLSSVTAADTAVYYCARHY<br>GATAGLFDYWGQGTLVTVS<br>SA | 48 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM183 | QLQLQESGPGLVKPSETLSL<br>TCTVSGGSISSSSYFWGWIR<br>QPPGKGLEWIGSIYYSGRTY<br>YNPSLKSRVTISVDTSKNQFS<br>LKLSSVTAADTAVYYCARH<br>QGATAGLFDYWGQGTLVTV<br>SSA | 49 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM184 | QLQLQESGPGLVKPSETLSL<br>TCTVSGGSISSSSYFWGWIR<br>QPPGKGLEWIGSIYYSGRTY<br>YNPSLKSRVTISVDTSKNQFS<br>LKLSSVTAADTAVYYCARH<br>HGATAGLFDYWGQGTLVTV<br>SSA | 50 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM185 | QLQLQESGPGLVKPSETLSL<br>TCTVSGGSISSSSYFWGWIR<br>QPPGKGLEWIGSIYYSGRTY<br>YNPSLKSRVTISVDTSKNQFS<br>LKLSSVTAADTAVYYCARH<br>YGATAGLFDYWGQGTLVTV<br>SSA | 51 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM186 | QLQLQESGPGLVKPSETLSL<br>TCTVSGGSISSSSYFWGWIR<br>QPPGKGLEWIGSIYYSGWTY<br>YNPSLKSRVTISVDTSKNQFS<br>LKLSSVTAADTAVYYCARH<br>QGATAGLFDYWGQGTLVTV<br>SSA | 52 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM187 | QLQLQESGPGLVKPSETLSL<br>TCTVSGGSISSSSYFWGWIR<br>QPPGKGLEWIGSIYYSGWTY<br>YNPSLKSRVTISVDTSKNQFS<br>LKLSSVTAADTAVYYCARH<br>HGATAGLFDYWGQGTLVTV<br>SSA | 53 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |
| BCBM188 | QLQLQESGPGLVKPSETLSL<br>TCTVSGGSISSSSYFWGWIR<br>QPPGKGLEWIGSIYYSGWTY<br>YNPSLKSRVTISVDTSKNQFS<br>LKLSSVTAADTAVYYCARH<br>YGATAGLFDYWGQGTLVTV<br>SSA | 54 | SYVLTQPPSVSVAPGQTA<br>RITCGGNNIGSKSNGWYQ<br>QPPGQAPVVVVYDDSDR<br>PSGIPERFSGSNSGNTATL<br>TISRVEAGDEAVYYCQV<br>WDSSSDHVVFGGGTKLT<br>VL | 28 |

Thus, in addition to BCMB69, 28 mutants were expressed and purified as described in Example 3 and characterized for binding to BCMA-expressing cells by flow cytometry as described in Example 4. Seven of the 28 mutants bound to cells expressing BCMA and were moved forward for the purpose of making a BCMA×CD3 bispecific panel.

Example 8: Preparation of BCMA and CD3 Antibodies in a Bispecific Format in IgG4 S228P, L234A, L235A BCMA antibodies were expressed as IgG4, having Fc substitutions S228P, L234A, and L235A (numbering according to EU index). A monospecific anti-CD3 antibody CD3B19 was also generated comprising the heavy and light chains having the sequences of SEQ ID NO: 55 and SEQ ID NO: 56, respectively.

The monospecific antibodies were purified using standard methods using a Protein A column (HiTrap MabSelect SuRe column). After elution, the pools were dialyzed into D-PBS, pH 7.2.

Bispecific BCMA×CD3 antibodies were generated by combining a monospecific CD3 mAb and a monospecific BCMA mAb in in-vitro Fab arm exchange (as described in WO2011/131746). Briefly, at about 1-20 mg/mL at a molar ratio of 1:1 of anti-BCMA/anti-CD3 antibody (or in some cases 6% extra of one parental antibody to deplete another) in PBS, pH 7-7.4 and 75 mM 2-mercaptoethanolamine (2-MEA) was mixed together and incubated at 31° C. for 5 hours, followed by removal of the 2-MEA via dialysis, diafiltration, tangential flow filtration and/or spinned cell filtration using standard methods. The formation of the bispecific BCMA×CD3 antibodies is analyzed by either cation exchange (CEX) HPLC or hydrophobic interaction chromatography (HIC) HPLC. If desired, the bispecific BCMA×CD3 antibody was polished by preparative CEX or HIC to remove the residual parental(s)

Heavy and Light chains for representative BCMA×CD3 bispecific antibodies are shown below in Table 10. BCMB178 had poor expression when combined with the CD3 arm, and as a result, was not further characterized.

TABLE 10

Heavy and Light Chain Sequences for Bispecific Antibodies

| Ab | | Amino Acid Sequence |
|---|---|---|
| BCMB72 | Heavy chain 1<br>CD3B219<br>(SEQ ID NO: 55) | EVQLVESGGGLVQPGGSLRLSCAASGFTFNTYAMN<br>WVRQAPGKGLEWVARIRSKYNNYATYYAASVKGRF<br>TISRDDSKNSLYLQMNSLKTEDTAVYYCARHGNFGN<br>SYVSWFAYWGQGTLVTVSSASTKGPSVFPLAPCSRS<br>TSESTAALGCLVKDYFPEPVTVSWNSGALTSGVHTFP<br>AVLQSSGLYSLSSVVTVPSSSLGTKTYTCNVDHKPSN<br>TKVDKRVESKYGPPCPPCPAPEAAGGPSVFLFPPKPK<br>DTLMISRTPEVTCVVVDVSQEDPEVQFNWYVDGVEV<br>HNAKTKPREEQFNSTYRVVSVLTVLHQDWLNGKEY<br>KCKVSNKGLPSSIEKTISKAKGQPREPQVYTLPPSQEE<br>MTKNQVSLTCLVKGFYPSDIAVEWESNGQPENNYKT<br>TPPVLDSDGSFLLYSKLTVDKSRWQEGNVFSCSVMH<br>EALHNHYTQKSLSLSLGK |
| | Light chain 1<br>CD3B219<br>(SEQ ID NO: 56) | QTVVTQEPSLTVSPGGTVTLTCRSSTGAVTTSNYAN<br>WVQQKPGQAPRGLIGGTNKRAPGTPARFSGSLLGGK<br>AALTLSGVQPEDEAEYYCALWYSNLWVFGGGTKLT<br>VLGQPKAAPSVTLFPPSSEELQANKATLVCLISDFYPG<br>AVTVAWKADSSPVKAGVETTTPSKQSNNKYAASSY<br>LSLTPEQWKSHRSYSCQVTHEGSTVEKTVAPTECS |
| | Heavy chain 2<br>BCMB69<br>(SEQ ID NO: 65) | QLQLQESGPGLVKPSETLSLTCTVSGGSISSGSYFWG<br>WIRQPPGKGLEWIGSIYYSGITYyNPSLKSRVTISVD<br>TSKNQFSLKLSSVTAADTAVYYCARHDGAVAGLFDY<br>WGQGTLVTVSSASTKGPSVFPLAPCSRSTSESTAALG<br>CLVKDYFPEPVTVSWNSGALTSGVHTFPAVLQSSGL<br>YSLSSVVTVPSSSLGTKTYTCNVDHKPSNTKVDKRV<br>ESKYGPPCPPCPAPEAAGGPSVFLFPPKPKDTLMISRT<br>PEVTCVVDVSQEDPEVQFNWYVDGVEVHNAKTKP<br>REEQFNSTYRVVSVLTVLHQDWLNGKEYKCKVSNK<br>GLPSSIEKTISKAKGQPREPQVYTLPPSQEEMTKNQVS<br>LTCLVKGFYPSDIAVEWESNGQPENNYKTTPPVLDSD<br>GSFFLYSRLTVDKSRWQEGNVFSCSVMHEALHNHYT<br>QKSLSLSLGK |
| | Light chain 2<br>BCMB69<br>(SEQ ID NO: 76) | SYVLTQPPSVSVAPGQTARITCGGNNIGSKSVHWYQ<br>QPPGQAPVVVVYDDSDRPSGIPERFSGSNSGNTATLTI<br>SRVEAGDEAVYYCQVWDSSSDHVVFGGGTKLTVLG<br>QPKAAPSVTLFPPSSEELQANKATLVCLISDFYPGAVT<br>VAWKGDSSPVKAGVETTTPSKQSNNKYAASSYLSLT<br>PEQWKSHRSYSCQVTHEGSTVEKTVAPTECS |
| BC3B7 | Heavy chain 1<br>CD3B219<br>(SEQ ID NO: 55) | EVQLVESGGGLVQPGGSLRLSCAASGFTFNTYAMN<br>WVRQAPGKGLEWVARIRSKYNNYATYYAASVKGRF<br>TISRDDSKNSLYLQMNSLKTEDTAVYYCARHGNFGN<br>SYVSWFAYWGQGTLVTVSSASTKGPSVFPLAPCSRS<br>TSESTAALGCLVKDYFPEPVTVSWNSGALTSGVHTFP<br>AVLQSSGLYSLSSVVTVPSSSLGTKTYTCNVDHKPSN<br>TKVDKRVESKYGPPCPPCPAPEAAGGPSVFLFPPKPK<br>DTLMISRTPEVTCVVVDVSQEDPEVQFNWYVDGVEV<br>HNAKTKPREEQFNSTYRVVSVLTVLHQDWLNGKEY<br>KCKVSNKGLPSSIEKTISKAKGQPREPQVYTLPPSQEE<br>MTKNQVSLTCLVKGFYPSDIAVEWESNGQPENNYKT<br>TPPVLDSDGSFLLYSKLTVDKSRWQEGNVFSCSVMH<br>EALHNHYTQKSLSLSLGK |
| | Light chain 1<br>CD3B219<br>(SEQ ID NO: 56) | QTVVTQEPSLTVSPGGTVTLTCRSSTGAVTTSNYAN<br>WVQQKPGQAPRGLIGGTNKRAPGTPARFSGSLLGGK<br>AALTLSGVQPEDEAEYYCALWYSNLWVFGGGTKLT<br>VLGQPKAAPSVTLFPPSSEELQANKATLVCLISDFYPG<br>AVTVAWKADSSPVKAGVETTTPSKQSNNKYAASSY<br>LSLTPEQWKSHRSYSCQVTHEGSTVEKTVAPTECS |

TABLE 10-continued

| Heavy and Light Chain Sequences for Bispecific Antibodies | | |
|---|---|---|
| Ab | | Amino Acid Sequence |
| | Heavy chain 2<br>BCMB117<br>(SEQ ID NO: 67) | QLQLQESGPGLVKPSETLSLTCTVSGGSISSGSYFWG<br>WIRQPPGKGLEWIGSIYYSGITYYNPSLKSRVTISVDT<br>SKNQFSLKLSSVTAADTAVYYCARHDGAVAGLFDY<br>WGQGTLVTVSSASTKGPSVFPLAPCSRSTSESTAALG<br>CLVKDYFPEPVTVSWNSGALTSGVHTFPAVLQSSGL<br>YSLSSVVTVPSSSLGTKTYTCNVDHKPSNTKVDKRV<br>ESKYGPPCPPCPAPEAAGGPSVFLFPPKPKDTLMISRT<br>PEVTCVVVDVSQEDPEVQFNWYVDGVEVHNAKTKP<br>REEQFNSTYRVVSVLTVLHQDWLNGKEYKCKVSNK<br>GLPSSIEKTISKAKGQPREPQVYTLPPSQEEMTKNQVS<br>LTCLVKGFYPSDIAVEWESNGQPENNYKTTPPVLDSD<br>GSFFLYSRLTVDKSRWQEGNVFSCSVMHEALHNHYT<br>QKSLSLSLGK |
| | Light chain 2<br>BCMB117<br>(SEQ ID NO: 66) | SYVLTQPPSVSVAPGQTARITCGGNNIGSKSVHWYQ<br>QPPGQAPVVVVYDDSDRPSGIPERFSGSNSGNTATLTI<br>SRVEAGDEAVYYCQVWDSSSDHVVFGGGTKLTVLG<br>QPKAAPSVTLFPPSSEELQANKATLVCLISDFYPGAVT<br>VAWKADSSPVKAGVETTTPSKQSNNKYAASSYLSLT<br>PEQWKSHRSYSCQVTHEGSTVEKTVAPTECS |
| BC3B8 | Heavy chain 1<br>CD3B219<br>(SEQ ID NO: 55) | EVQLVESGGGLVQPGGSLRLSCAASGFTFNTYAMN<br>WVRQAPGKGLEWVARIRSKYNNYATYYAASVKGRF<br>TISRDDSKNSLYLQMNSLKTEDTAVYYCARHGNFGN<br>SYVSWFAYWGQGTLVTVSSASTKGPSVFPLAPCSRS<br>TSESTAALGCLVKDYFPEPVTVSWNSGALTSGVHTFP<br>AVLQSSGLYSLSSVVTVPSSSLGTKTYTCNVDHKPSN<br>TKVDKRVESKYGPPCPPCPAPEAAGGPSVFLFPPKPK<br>DTLMISRTPEVTCVVVDVSQEDPEVQFNWYVDGVEV<br>HNAKTKPREEQFNSTYRVVSVLTVLHQDWLNGKEY<br>KCKVSNKGLPSSIEKTISKAKGQPREPQVYTLPPSQEE<br>MTKNQVSLTCLVKGFYPSDIAVEWESNGQPENNYKT<br>TPPVLDSDGSFLLYSKLTVDKSRWQEGNVFSCSVMH<br>EALHNHYTQKSLSLSLGK |
| | Light chain 1<br>CD3B219<br>(SEQ ID NO: 56) | QTVVTQEPSLTVSPGGTVTLTCRSSTGAVTTSNYAN<br>WVQQKPGQAPRGLIGGTNKRAPGTPARFSGSLLGGK<br>AALTLSGVQPEDEAEYYCALWYSNLWVFGGGTKLT<br>VLGQPKAAPSVTLFPPSSEELQANKATLVCLISDFYPG<br>AVTVAWKADSSPVKAGVETTTPSKQSNNKYAASSY<br>LSLTPEQWKSHRSYSCQVTHEGSTVEKTVAPTECS |
| | Heavy chain 2<br>BCMB123<br>(SEQ ID NO: 68) | QLQLQESGPGLVKPSETLSLTCTVSGGSISSSSYFWG<br>WIRQPPGKGLEWIGSIYYSGITYYNPSLKSRVTISVDT<br>SKNQFSLKLSSVTAADTAVYYCARHDGAVAGLFDY<br>WGQGTLVTVSSASTKGPSVFPLAPCSRSTSESTAALG<br>CLVKDYFPEPVTVSWNSGALTSGVHTFPAVLQSSGL<br>YSLSSVVTVPSSSLGTKTYTCNVDHKPSNTKVDKRV<br>ESKYGPPCPPCPAPEAAGGPSVFLFPPKPKDTLMISRT<br>PEVTCVVVDVSQEDPEVQFNWYVDGVEVHNAKTKP<br>REEQFNSTYRVVSVLTVLHQDWLNGKEYKCKVSNK<br>GLPSSIEKTISKAKGQPREPQVYTLPPSQEEMTKNQVS<br>LTCLVKGFYPSDIAVEWESNGQPENNYKTTPPVLDSD<br>GSFFLYSRLTVDKSRWQEGNVFSCSVMHEALHNHYT<br>QKSLSLSLGK |
| | Light chain 2<br>BCMB123<br>(SEQ ID NO: 66) | SYVLTQPPSVSVAPGQTARITCGGNNIGSKSVHWYQ<br>QPPGQAPVVVVYDDSDRPSGIPERFSGSNSGNTATLTI<br>SRVEAGDEAVYYCQVWDSSSDHVVFGGGTKLTVLG<br>QPKAAPSVTLFPPSSEELQANKATLVCLISDFYPGAVT<br>VAWKADSSPVKAGVETTTPSKQSNNKYAASSYLSLT<br>PEQWKSHRSYSCQVTHEGSTVEKTVAPTECS |
| BC3B9 | Heavy chain 1<br>CD3B219<br>(SEQ ID NO: 55) | EVQLVESGGGLVQPGGSLRLSCAASGFTFNTYAMN<br>WVRQAPGKGLEWVARIRSKYNNYATYYAASVKGRF<br>TISRDDSKNSLYLQMNSLKTEDTAVYYCARHGNFGN<br>SYVSWFAYWGQGTLVTVSSASTKGPSVFPLAPCSRS<br>TSESTAALGCLVKDYFPEPVTVSWNSGALTSGVHTFP<br>AVLQSSGLYSLSSVVTVPSSSLGTKTYTCNVDHKPSN<br>TKVDKRVESKYGPPCPPCPAPEAAGGPSVFLFPPKPK<br>DTLMISRTPEVTCVVVDVSQEDPEVQFNWYVDGVEV<br>HNAKTKPREEQFNSTYRVVSVLTVLHQDWLNGKEY<br>KCKVSNKGLPSSIEKTISKAKGQPREPQVYTLPPSQEE<br>MTKNQVSLTCLVKGFYPSDIAVEWESNGQPENNYKT<br>TPPVLDSDGSFLLYSKLTVDKSRWQEGNVFSCSVMH<br>EALHNHYTQKSLSLSLGK |
| | Light chain 1<br>CD3B219<br>(SEQ ID NO: 56) | QTVVTQEPSLTVSPGGTVTLTCRSSTGAVTTSNYAN<br>WVQQKPGQAPRGLIGGTNKRAPGTPARFSGSLLGGK<br>AALTLSGVQPEDEAEYYCALWYSNLWVFGGGTKLT<br>VLGQPKAAPSVTLFPPSSEELQANKATLVCLISDFYPG |

TABLE 10-continued

| Heavy and Light Chain Sequences for Bispecific Antibodies | | |
|---|---|---|
| Ab | | Amino Acid Sequence |
| | | AVTVAWKADSSPVKAGVETTTPSKQSNNKYAASSY<br>LSLTPEQWKSHRSYSCQVTHEGSTVEKTVAPTECS |
| | Heavy chain 2<br>BCMB128<br>(SEQ ID NO: 69) | QLQLQESGPGLVKPSETLSLTCTVSGGSISSSYFWG<br>WIRQPPGKGLEWIGSIYYSGITYYNPSLKSRVTISVDT<br>SKNQFSLKLSSVTAADTAVYYCARHDGATAGLFDY<br>WGQGTLVTVSSASTKGPSVFPLAPCSRSTSESTAALG<br>CLVKDYFPEPVTVSWNSGALTSGVHTFPAVLQSSGL<br>YSLSSVVTVPSSSLGTKTYTCNVDHKPSNTKVDKRV<br>ESKYGPPCPPCPAPEAAGGPSVFLFPPKPKDTLMISRT<br>PEVTCVVVDVSQEDPEVQFNWYVDGVEVHNAKTKP<br>REEQFNSTYRVVSVLTVLHQDWLNGKEYKCKVSNK<br>GLPSSIEKTISKAKGQPREPQVYTLPPSQEEMTKNQVS<br>LTCLVKGFYPSDIAVEWESNGQPENNYKTTPPVLDSD<br>GSFFLYSRLTVDKSRWQEGNVFSCSVMHEALHNHYT<br>QKSLSLSLGK |
| | Light chain 2<br>BCBM128<br>(SEQ ID NO: 66) | SYVLTQPPSVSVAPGQTARITCGGNNIGSKSVHWYQ<br>QPPGQAPVVVVYDDSDRPSGIPERFSGSNSGNTATLTI<br>SRVEAGDEAVYYCQVWDSSSDHVVFGGGTKLTVLG<br>QPKAAPSVTLFPPSSEELQANKATLVCLISDFYPGAVT<br>VAWKADSSPVKAGVETTTPSKQSNNKYAASSYLSLT<br>PEQWKSHRSYSCQVTHEGSTVEKTVAPTECS |
| BC3B10 | Heavy chain 1<br>CD3B219<br>(SEQ ID NO: 55) | EVQLVESGGGLVQPGGSLRLSCAASGFTFNTYAMN<br>WVRQAPGKGLEWVARIRSKYNNYATYYAASVKGRF<br>TISRDDSKNSLYLQMNSLKTEDTAVYYCARHGNFGN<br>SYVSWFAYWGQGTLVTVSSASTKGPSVFPLAPCSRS<br>TSESTAALGCLVKDYFPEPVTVSWNSGALTSGVHTFP<br>AVLQSSGLYSLSSVVTVPSSSLGTKTYTCNVDHKPSN<br>TKVDKRVESKYGPPCPPCPAPEAAGGPSVFLFPPKPK<br>DTLMISRTPEVTCVVVDVSQEDPEVQFNWYVDGVEV<br>HNAKTKPREEQFNSTYRVVSVLTVLHQDWLNGKEY<br>KCKVSNKGLPSSIEKTISKAKGQPREPQVYTLPPSQEE<br>MTKNQVSLTCLVKGFYPSDIAVEWESNGQPENNYKT<br>TPPVLDSDGSFLLYSKLTVDKSRWQEGNVFSCSVMH<br>EALHNHYTQKSLSLSLGK |
| | Light chain 1<br>CD3B219<br>(SEQ ID NO: 56) | QTVVTQEPSLTVSPGGTVTLTCRSSTGAVTTSNYAN<br>WVQQKPGQAPRGLIGGTNKRAPGTPARFSGSLLGGK<br>AALTLSGVQPEDEAEYYCALWYSNLWVFGGGTKLT<br>VLGQPKAAPSVTLFPPSSEELQANKATLVCLISDFYPG<br>AVTVAWKADSSPVKAGVETTTPSKQSNNKYAASSY<br>LSLTPEQWKSHRSYSCQVTHEGSTVEKTVAPTECS |
| | Heavy chain 2<br>BCMB129<br>(SEQ ID NO: 70) | QLQLQESGPGLVKPSETLSLTCTVSGGSISSGSYFWG<br>WIRQPPGKGLEWIGSIYYSGSTYYNPSLKSRVTISVDT<br>SKNQFSLKLSSVTAADTAVYYCARHDGAVAGLFDY<br>WGQGTLVTVSSASTKGPSVFPLAPCSRSTSESTAALG<br>CLVKDYFPEPVTVSWNSGALTSGVHTFPAVLQSSGL<br>YSLSSVVTVPSSSLGTKTYTCNVDHKPSNTKVDKRV<br>ESKYGPPCPPCPAPEAAGGPSVFLFPPKPKDTLMISRT<br>PEVTCVVVDVSQEDPEVQFNWYVDGVEVHNAKTKP<br>REEQFNSTYRVVSVLTVLHQDWLNGKEYKCKVSNK<br>GLPSSIEKTISKAKGQPREPQVYTLPPSQEEMTKNQVS<br>LTCLVKGFYPSDIAVEWESNGQPENNYKTTPPVLDSD<br>GSFFLYSRLTVDKSRWQEGNVFSCSVMHEALHNHYT<br>QKSLSLSLGK |
| | Light chain 2<br>BCMB129<br>(SEQ ID NO: 66) | SYVLTQPPSVSVAPGQTARITCGGNNIGSKSVHWYQ<br>QPPGQAPVVVVYDDSDRPSGIPERFSGSNSGNTATLTI<br>SRVEAGDEAVYYCQVWDSSSDHVVFGGGTKLTVLG<br>QPKAAPSVTLFPPSSEELQANKATLVCLISDFYPGAVT<br>VAWKADSSPVKAGVETTTPSKQSNNKYAASSYLSLT<br>PEQWKSHRSYSCQVTHEGSTVEKTVAPTECS |
| BC3B11 | Heavy chain 1<br>CD3B219<br>(SEQ ID NO: 55) | EVQLVESGGGLVQPGGSLRLSCAASGFTFNTYAMN<br>WVRQAPGKGLEWVARIRSKYNNYATYYAASVKGRF<br>TISRDDSKNSLYLQMNSLKTEDTAVYYCARHGNFGN<br>SYVSWFAYWGQGTLVTVSSASTKGPSVFPLAPCSRS<br>TSESTAALGCLVKDYFPEPVTVSWNSGALTSGVHTFP<br>AVLQSSGLYSLSSVVTVPSSSLGTKTYTCNVDHKPSN<br>TKVDKRVESKYGPPCPPCPAPEAAGGPSVFLFPPKPK<br>DTLMISRTPEVTCVVVDVSQEDPEVQFNWYVDGVEV<br>HNAKTKPREEQFNSTYRVVSVLTVLHQDWLNGKEY<br>KCKVSNKGLPSSIEKTISKAKGQPREPQVYTLPPSQEE<br>MTKNQVSLTCLVKGFYPSDIAVEWESNGQPENNYKT<br>TPPVLDSDGSFLLYSKLTVDKSRWQEGNVFSCSVMH<br>EALHNHYTQKSLSLSLGK |

TABLE 10-continued

| Heavy and Light Chain Sequences for Bispecific Antibodies | | |
|---|---|---|
| Ab | | Amino Acid Sequence |
| | Light chain 1<br>CD3B219<br>(SEQ ID NO: 56) | QTVVTQEPSLTVSPGGTVTLTCRSSTGAVTTSNYAN<br>WVQQKPGQAPRGLIGGTNKRAPGTPARFSGSLLGGK<br>AALTLSGVQPEDEAEYYCALWYSNLWVFGGGTKLT<br>VLGQPKAAPSVTLFPPSSEELQANKATLVCLISDFYPG<br>AVTVAWKADSSPVKAGVETTTPSKQSNNKYAASSY<br>LSLTPEQWKSHRSYSCQVTHEGSTVEKTVAPTECS |
| | Heavy chain 2<br>BCMB176<br>(SEQ ID NO: 71) | QLQLQESGPGLVKPSETLSLTCTVSGGSISSSSYFWG<br>WIRQPPGKGLEWIGSIYYSGITYYNPSLKSRVTISVDT<br>SKNQFSLKLSSVTAADTAVYYCARHDGATAGLFDY<br>WGQGTLVTVSSASTKGPSVFPLAPCSRSTSESTAALG<br>CLVKDYFPEPVTVSWNSGALTSGVHTFPAVLQSSGL<br>YSLSSVVTVPSSSLGTKTYTCNVDHKPSNTKVDKRV<br>ESKYGPPCPPCPAPEAAGGPSVFLFPPKPKDTLMISRT<br>PEVTCVVVDVSQEDPEVQFNWYVDGVEVHNAKTKP<br>REEQFNSTYRVVSVLTVLHQDWLNGKEYKCKVSNK<br>GLPSSIEKTISKAKGQPREPQVYTLPPSQEEMTKNQVS<br>LTCLVKGFYPSDIAVEWESNGQPENNYKTTPPVLDSD<br>GSFFLYSRLTVDKSRWQEGNVFSCSVMHEALHNHYT<br>QKSLSLSLGK |
| | Light chain 2<br>BCBM176<br>(SEQ ID NO: 66) | SYVLTQPPSVSVAPGQTARITCGGNNIGSKSVHWYQ<br>QPPGQAPVVVVYDDSDRPSGIPERFSGSNSGNTATLTI<br>SRVEAGDEAVYYCQVWDSSSDHVVFGGGTKLTVLG<br>QPKAAPSVTLFPPSSEELQANKATLVCLISDFYPGAVT<br>VAWKADSSPVKAGVETTTPSKQSNNKYAASSYLSLT<br>PEQWKSHRSYSCQVTHEGSTVEKTVAPTECS |
| BC3B12 | Heavy chain 1<br>CD3B219<br>(SEQ ID NO: 55) | EVQLVESGGGLVQPGGSLRLSCAASGFTFNTYAMN<br>WVRQAPGKGLEWVARIRSKYNNYATYYAASVKGRF<br>TISRDDSKNSLYLQMNSLKTEDTAVYYCARHGNFGN<br>SYVSWFAYWGQGTLVTVSSASTKGPSVFPLAPCSRS<br>TSESTAALGCLVKDYFPEPVTVSWNSGALTSGVHTFP<br>AVLQSSGLYSLSSVVTVPSSSLGTKTYTCNVDHKPSN<br>TKVDKRVESKYGPPCPPCPAPEAAGGPSVFLFPPKPK<br>DTLMISRTPEVTCVVVDVSQEDPEVQFNWYVDGVEV<br>HNAKTKPREEQFNSTYRVVSVLTVLHQDWLNGKEY<br>KCKVSNKGLPSSIEKTISKAKGQPREPQVYTLPPSQEE<br>MTKNQVSLTCLVKGFYPSDIAVEWESNGQPENNYKT<br>TPPVLDSDGSFLLYSKLTVDKSRWQEGNVFSCSVMH<br>EALHNHYTQKSLSLSLGK |
| | Light chain 1<br>CD3B219<br>(SEQ ID NO: 56) | QTVVTQEPSLTVSPGGTVTLTCRSSTGAVTTSNYAN<br>WVQQKPGQAPRGLIGGTNKRAPGTPARFSGSLLGGK<br>AALTLSGVQPEDEAEYYCALWYSNLWVFGGGTKLT<br>VLGQPKAAPSVTLFPPSSEELQANKATLVCLISDFYPG<br>AVTVAWKADSSPVKAGVETTTPSKQSNNKYAASSY<br>LSLTPEQWKSHRSYSCQVTHEGSTVEKTVAPTECS |
| | Heavy chain 2<br>BCMB177<br>(SEQ ID NO: 72) | QLQLQESGPGLVKPSETLSLTCTVSGGSISSSSYFWG<br>WIRQPPGKGLEWIGSIYYSGRTYYNPSLKSRVTISVD<br>TSKNQFSLKLSSVTAADTAVYYCARHDGATAGLFDY<br>WGQGTLVTVSSASTKGPSVFPLAPCSRSTSESTAALG<br>CLVKDYFPEPVTVSWNSGALTSGVHTFPAVLQSSGL<br>YSLSSVVTVPSSSLGTKTYTCNVDHKPSNTKVDKRV<br>ESKYGPPCPPCPAPEAAGGPSVFLFPPKPKDTLMISRT<br>PEVTCVVVDVSQEDPEVQFNWYVDGVEVHNAKTKP<br>REEQFNSTYRVVSVLTVLHQDWLNGKEYKCKVSNK<br>GLPSSIEKTISKAKGQPREPQVYTLPPSQEEMTKNQVS<br>LTCLVKGFYPSDIAVEWESNGQPENNYKTTPPVLDSD<br>GSFFLYSRLTVDKSRWQEGNVFSCSVMHEALHNHYT<br>QKSLSLSLGK |
| | Light chain 2<br>BCMB177<br>(SEQ ID NO: 66) | SYVLTQPPSVSVAPGQTARITCGGNNIGSKSVHWYQ<br>QPPGQAPVVVVYDDSDRPSGIPERFSGSNSGNTATLTI<br>SRVEAGDEAVYYCQVWDSSSDHVVFGGGTKLTVLG<br>QPKAAPSVTLFPPSSEELQANKATLVCLISDFYPGAVT<br>VAWKADSSPVKAGVETTTPSKQSNNKYAASSYLSLT<br>PEQWKSHRSYSCQVTHEGSTVEKTVAPTECS |

Example 9: BCMA Affinity Determinations for BCMA Antibodies and BCMA×CD3 Bispecifics Surface Plasmon Resonance (SPR) was used to measure the human BCMA affinity values of BCMA antibodies used for the generation of CD3 bispecifics. The protocol followed for SPR was similar to that described in Example 4. The results shown in Table 11 indicate that all samples bound to monomeric BCMA antigen with varying affinities. The parental mAb (BCMB69) had a binding affinities of ~1.4 nM. BCMB117 and BCMB128 had affinities in the range of BCMB69, whereas BCMB123, BCMB129, BCMB176 and BCMB177 had relatively weaker affinities (3 to 15-fold) due to faster off-rates. In order to assess data reproducibility, all the samples were run at least in triplicates and standard deviations are reported.

TABLE 11

Binding affinities of anti-BCMA mAbs with monomeric human BCMA by SPR

| mAbs | $k_{on}$ ($\times 10^6$ 1/Ms) | $k_{off}$ ($\times 10^{-3}$ 1/s) | $K_D$ (nM) |
|---|---|---|---|
| BCMB69 | 2.74 ± 0.02 | 3.95 ± 0.19 | 1.44 ± 0.05 |
| BCMB117 | 2.57 ± 0.21 | 3.42 ± 0.25 | 1.34 ± 0.20 |
| BCMB123 | 2.14 ± 0.04 | 11.0 ± 1.33 | 5.12 ± 0.69 |
| BCMB128 | 4.20 ± 0.13 | 8.70 ± 0.61 | 2.07 ± 0.21 |
| BCMB129 | 1.54 ± 0.06 | 8.43 ± 0.44 | 5.47 ± 0.13 |
| BCMB176 | 4.00 ± 0.05 | 28.8 ± 1.25 | 7.18 ± 0.22 |
| BCMB177 | 2.80 ± 0.22 | 56.6 ± 5.54 | 20.2 ± 1.57 |

SPR was also used to measure affinity values of BCMA×CD3 bispecific antibodies for human and cyno BCMA. The results in Table 12 indicate that all samples bound to Fc-BCMA antigens with varying affinities. BC3B7 and BC3B9 had affinities in the range of BCMB72 for human BCMA whereas the remaining bispecifics had 2-3 fold weaker affinities when compared to BCMB72. For cyno Fc-BCMA, BC3B7 and BC3B9 had 2-3 fold tighter affinities than BCMB72 ($K_D$ 0.65-0.37 nM, respectively), whereas the remaining mAbs retained similar binding as BCMB72 ($K_D$~0.8-1.2 nM). In order to assess data reproducibility, all the samples were run at least in triplicates and standard deviations are reported.

TABLE 12

Binding affinities of BCMA × CD3 antibodies for Fc-BCMA by SPR

| BCMA × CD3 | Fc-BCMA | $k_{on1}$ ($\times 10^6$ 1/Ms) | $k_{off1}$ ($\times 10^{-3}$ 1/s) | $K_{D1}$ (nM) | $k_{on2}$ ($\times 10^{-3}$ 1/s) | $k_{off2}$ ($\times 10^{-4}$ 1/s) | Final $K_D$ (nM) |
|---|---|---|---|---|---|---|---|
| BCMB72 | Hu | 1.35 ± 0.11 | 2.08 ± 0.80 | 1.51 ± 0.45 | 6.56 ± 1.27 | 2.79 ± 0.55 | 0.06 ± 0.01 |
| (B69 × B219) | Cy | 1.26 ± 0.12 | 4.83 ± 0.28 | 3.87 ± 0.57 | 1.06 ± 0.10 | 7.85 ± 1.04 | 1.65 ± 0.26 |
| BC3B7 | Hu | 1.48 ± 0.09 | 1.58 ± 0.30 | 1.07 ± 0.20 | 4.97 ± 0.67 | 2.94 ± 0.54 | 0.06 ± 0.01 |
| (B117 × B219) | Cy | 1.38 ± 0.07 | 4.17 ± 0.19 | 3.04 ± 0.25 | 1.50 ± 0.06 | 4.15 ± 0.53 | 0.65 ± 0.04 |
| BC3B8 | Hu | 1.35 ± 0.08 | 1.23 ± 0.24 | 0.91 ± 0.16 | 3.13 ± 0.48 | 5.94 ± 0.82 | 0.14 ± 0.01 |
| (B123 × B219) | Cy | 1.09 ± 0.05 | 7.34 ± 0.21 | 6.77 ± 0.48 | 1.94 ± 0.08 | 3.26 ± 0.43 | 0.97 ± 0.09 |
| BC3B9 | Hu | 2.58 ± 0.14 | 2.05 ± 0.75 | 0.79 ± 0.25 | 5.06 ± 1.12 | 3.64 ± 0.36 | 0.05 ± 0.01 |
| (B128 × B219) | Cy | 2.18 ± 0.06 | 4.23 ± 0.23 | 1.94 ± 0.14 | 1.60 ± 0.09 | 3.76 ± 0.52 | 0.37 ± 0.04 |
| BC3B10 | Hu | 1.02 ± 0.07 | 1.55 ± 0.31 | 1.50 ± 0.22 | 4.53 ± 0.64 | 5.31 ± 1.20 | 0.16 ± 0.03 |
| (B129 × B219) | Cy | 0.93 ± 0.04 | 6.36 ± 0.28 | 6.84 ± 0.48 | 1.65 ± 0.07 | 3.59 ± 0.50 | 1.22 ± 0.17 |
| BC3B11 | Hu | 2.26 ± 0.16 | 1.32 ± 0.15 | 0.58 ± 0.07 | 2.52 ± 0.32 | 6.89 ± 1.17 | 0.12 ± 0.02 |
| (B176 × B219) | Cy | 1.93 ± 0.10 | 6.83 ± 0.11 | 3.56 ± 0.23 | 1.47 ± 0.04 | 3.95 ± 0.76 | 0.75 ± 0.11 |
| BC3B12 | Hu | 1.78 ± 0.09 | 1.29 ± 0.05 | 0.72 ± 0.05 | 1.29 ± 0.15 | 5.57 ± 0.38 | 0.22 ± 0.03 |
| (B177 × B219) | Cy | 1.48 ± 0.10 | 8.31 ± 0.30 | 5.65 ± 0.46 | 1.46 ± 0.07 | 3.37 ± 0.43 | 1.06 ± 0.15 |

The binding affinities of anti-BCMA×CD3 bispecific antibody (BCMB72) with Fc-fusion BCMA proteins (human, cyno and mouse) were measured by Surface Plasmon Resonance (SPR) using a Biacore T200 system (GE Healthcare, NJ).

The flow-cells 2, 3 and 4 of a streptavidin-derivatized sensor chip (GE Healthcare, Prod# BR-1005-31) were immobilized with biotinylated Fc-fusion human, cyno or mouse BCMA, respectively (BCMA immobilized levels between 12-16 response units (RU); Fc-BCMA proteins: human (R&D Systems; Prod#193-FC), cyno (in-house; Cat# BCMW6.001) and mouse (R&D Systems; Prod#593-BC) were biotinylated in-house). No protein was immobilized on flow-cell 1 and was used as a reference surface. Binding kinetics experiments were performed at 25° C. in running buffer (PBS pH 7.4, 0.005% P20, 3 mM EDTA). BCMB72 was prepared in running buffer starting from 100 nM to 0.16 nM at 5-fold dilutions. These solutions were injected for 5 min (association phase) at 50 μL/min and the dissociation was monitored for 15 min by flowing running buffer. The chip surface was regenerated by short injections of glycine (pH 1.5) and running buffer at 100 μL/min. Binding kinetics analysis of BCMB72 interactions with Fc-BCMA was performed by double referencing of the data by subtracting the curves generated by buffer injection from the reference-subtracted curves for analyte injections. Global kinetics fitting of the sensorgrams was performed using a Two-State binding Model using Biacore T200 Evaluation Software (GE Healthcare, NJ). The binding affinity results from the Two-State binding model for different BCMA species are reported as First Complex ($K_{D1}$) and Final Complex ($K_D$) (FIG. 5).

Example 10: Target-Specific T-Cell Activation and Cytotoxic Potency of BCMA×CD3 Antibodies in the Presence of Immortalized Cell Lines of Multiple Myeloma Background The activation of T-cells mediated by BCMA×CD3 antibodies was evaluated. Briefly, BCMB72 (BCMA×CD3) and control antibodies (BCMA×null and null×CD3) were diluted to 800 μg/ml in PBS. The titration was prepared in 4-fold serial dilutions in PBS in a 96-well U-bottom plate. The last column was left as PBS alone (vehicle control).

Target cells were cultured in antibiotic-free RPMI 1640 medium supplemented with GlutaMAX, 10% FBS and 25 mM HEPES (culture medium). On the set-up day (Day 1), target cells were counted and 10 million cells were centrifuged at 1350 rpm for 3 minutes after which, the supernatants were discarded. CellTrace FCSE proliferation stain was reconstituted in 18 μl of sterile DMSO and 1 μl of the solution was diluted in 10 ml of sterile PBS. Cell pellets were resuspended in 1 ml of CFSE dilution and incubated at room temperature for 8 minutes hidden from direct light. After the incubation, 1 ml of HI FBS was added to cell suspension to quench the surplus CFSE. Cells were washed twice in RPMI-1640 with 10% FBS. After reconstitution in 10 ml of RPMI, cells were counted and cell viability was recoded in a spreadsheet. Cells were diluted to 2.2×10^5/ml and incubated at 37° C. until use.

Pan T cells from normal donors were thawed in 37° C. water bath, after which the contents of the freeze vials were transferred to 50-ml conical vials and reconstituted in 15 ml of cold culture medium. Cells were then centrifuged at 1350 rpm at 4° C. for 3 minutes. The supernatants were discarded and cell pellets were reconstituted in 5 to 10 ml of culture medium. T cells were counted and the viability was recorded. Cells were then reconstituted in culture medium to 1.1×10^6/ml.

2×10^5 target cells were added to wells of a 96-well U-bottom plate, followed by Fc blocker (to final concentration of 2 mg/ml). All cell lines were incubated at room temperature for 10 minutes to block Fc receptor activity. 1×10^5 T cells were added to the wells (5:1 effector:target ratio). After target and T cells were mixed, 20 μl of BCMA×CD3 antibodies dilutions were added to each well. The plates were incubated at 37° C. with 5% $CO_2$ for 48 hours.

Two days later, the plates were centrifuged at 1350 rpm for 3 minutes at 4° C. and 100 μl of supernatants were transferred to a separate plate and stored at −80° C. for cytokine release assay. Cells were washed in 200 μl of PBS and incubated in 50 μl of near-IR Live/Dead stain (1:200 dilution) and anti-CD25 PE antibody (1:50 dilution) for 20 minutes at room temperature. Then, the cells were washed once in 200 μl of FACS buffer and finally reconstituted in 150 μl of FACS buffer. Cells were analyzed using FACSCanto II and FlowJo 7.6 for target cytotoxicity (% target) and T cell activation CD25+ (% live T cells). Graphing and fitting of data were done in GraphPad Prism 6 using nonlinear regression with variable slope (four parameters) function using least squares method.

FIGS. 8A, 8B, 8C, 8D and 8E shows that BCMB72 promotes consistent target-specific T cell activation, as assessed by CD25 upregulation on T cell surface. Fc blocker was used to prevent Fc receptor-dependent binding of antibodies to target cells. In general, data points aligned tightly along the generated fit curve and there was little variability between T cell donors. Maximal activation of 45-85% was achieved for $BCMA^+$ cells and 4-10% (equivalent to background levels) for $BCMA^-$ cells. The summary of the $EC_{50}$ and maximum T cell activation values from two independent experiments using T cells from multiple normal donors is shown in FIGS. 9A and 9B.

FIGS. 10A, 10B, 10C, 10D and 10E shows that BCMB72 had consistently strong cytotoxicity against $BCMA^+$ cell lines. Fc blocker was used to prevent Fc receptor-dependent binding of BCMB72 to target cells. In general, data points aligned tightly along the generated fit curve and there was little variability between T cell donors. Maximal lysis of 62-97% was achieved for $BCMA^+$ cells and 4-18% for $BCMA^-$ cells. The summary of the $EC_{50}$ and maximum lysis values from two independent experiments using T cells from multiple normal donors is shown in FIGS. 11A and 11B.

Figure 12A:
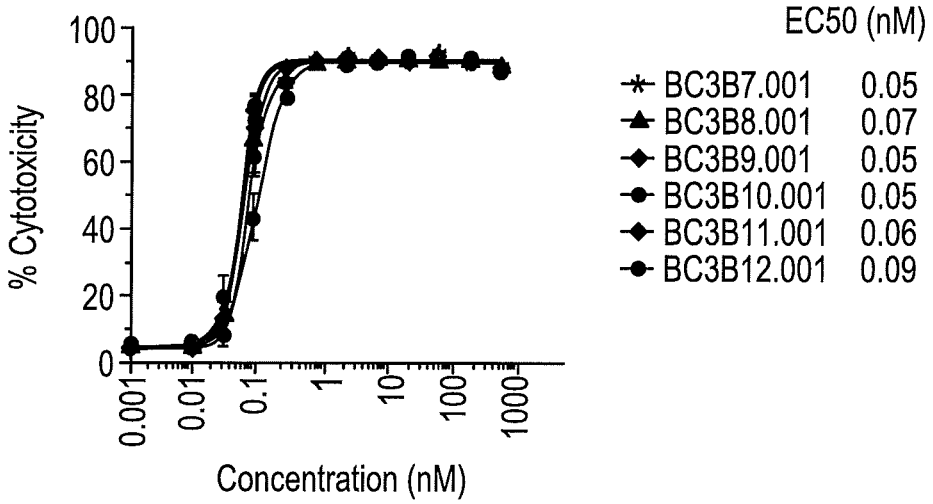
FIGS. 12A and 12B. Cytotoxicity and T cell activation in H929 cells. BCMA×CD3 bispecific antibodies (Mutant molecules of BCMB72) were tested in a T-cell mediated cytotoxicity assay. BCMA-positive cell line (H929) was incubated with various concentrations the antibodies for 48 hours in presence of exogenous human T cells from normal donors (donor ID's: M5763 and M6576). After 48 hour incubation cell killing was measured by flow cytometry based approach (FACS) and reported as % cytotoxicity in FIG. 12A.
Figure 12B:
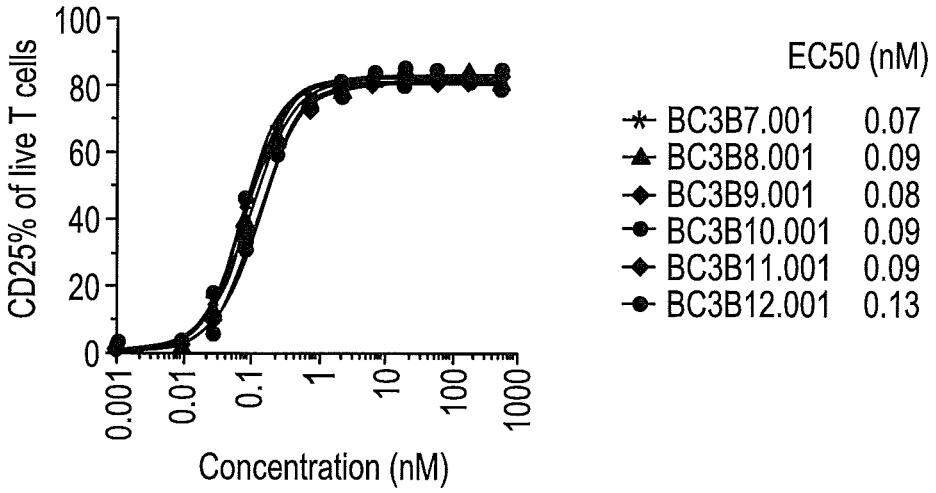

The other six BCMA×CD3 antibodies showed maximal cytotoxicity of 83 to 93% (FIG. 12 A) and T cell activation in the range of 74 to 83% for $BCMA^+$ H929 cells using two different donor T cells (FIG. 12B). These six BCMA×CD3 antibody molecules are potent in killing the BCMA+ target cell at an $EC_{50}$ value ranging from 0.04 to 0.09 nM.

Example 11: Binding Efficiency of BCMB72 on BCMA+ Cell Lines

The $EC_{50}$ values for BCMB72 binding to various BCMA+ cell lines of malignant background was assessed. Briefly, the bispecific antibody BCMB72 (BCMA×CD3) was diluted to 750 μg/ml in PBS. The titration was prepared in 3-fold serial dilutions in PBS in a 96-well U-bottom plate. The last column was left as PBS alone (vehicle control). H929 target cells were cultured in antibiotic-free RPMI 1640 medium supplemented with GlutaMAX, 10% FBS and 25 mM HEPES (culture medium). For the assay, target cell density and viability were measured and cells were then centrifuged at 1000 rpm for 5 minutes at 4° C. Cell pellets were then washed in 10 ml of PBS and centrifuged again at 1000 rpm for 5 minutes. Cells were resuspended in PBS at $5.5\times10^5$ cells/ml and 90 μl of cell suspension was aliquoted per well of a 96-well U-Bottom plate, followed by 10 μl/well of BCMB72 dilutions. The plates were incubated at 4° C. for 1 hour in the dark, then centrifuged at 1000 rpm for 5 minutes and supernatants were discarded. Cell pellets were washed twice in 200 μl of FACS buffer. PE labeled secondary antibody against human IgG4 Fc was dissolved in FACS buffer at 1:25 and 50 μl of the mix was added to the corresponding wells. Samples were incubated for 20 minutes at 4° C., washed in FACS buffer as described above, and reconstituted in 150 μl of FACS buffer for analysis on FACSCanto II. Data were analyzed using FlowJo 7.6 for BCMB72 binding and graphing and fitting of data were done in GraphPad Prism 6 using nonlinear regression with variable slope function using least squares method.

Figure 6:
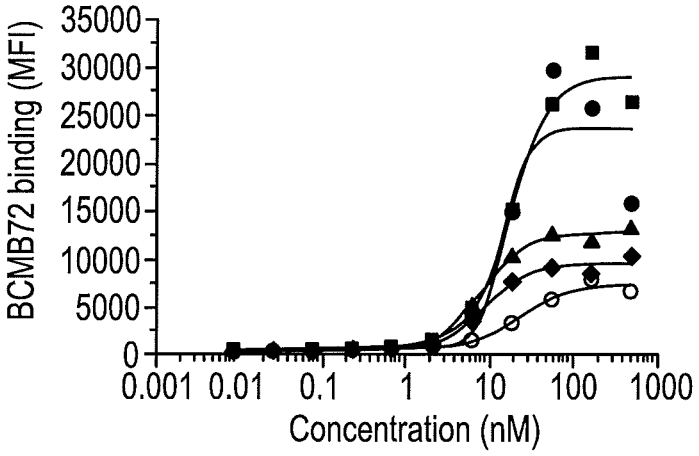
FIG. 6. $EC_{50}$ determination for BCMB72 binding on $BCMA^+$ cell lines. Cell lines were stained for BCMA using BCMB72. Geometrical mean fluorescence intensities of BCMB72 binding to cells are shown. $EC_{50}$ are indicated in the legend. Saturation was achieved at a concentration of around 100 nM. The mean fluorescence intensity was considered to derive the $EC_{50}$ values for U2932 ($EC_{50}$=7.92 nM), MM1R ($EC_{50}$=8.74 nM), H929 ($EC_{50}$=14.7 nM), EJM ($EC_{50}$=17.5 nM) and LP1 ($EC_{50}$=22.3 nM) cells. Graphing and fitting of data were done in GraphPad Prism 6 using nonlinear regression with variable slope (four parameters) function.

As seen in FIG. 6, BCMB72 is able to bind to all of the BCMA+ cell lines that were examined. The $EC_{50}$ for binding to H929 cells was 14.7 nM, to MM. 1R cells was 9.74 nM, to EJM cells was 17.5 nM, to LP1 cells was 22.3 nM and to U-2932 cells was 7.92 nM.

Example 12: Analysis of BCMA Expression and BCMB72 Binding in Ex Vivo Whole Blood from Normal Human Donors The expression of BCMA and BCMB72 binding on leukocytes was assessed in ex vivo whole blood from three normal human donors. Briefly, fresh peripheral blood from normal human donors was stored in heparin-coated tubes prior to the experiment. The blood was pipetted into 96-well U-Bottom plate in 100 μl aliquots. Staining antibodies were prepared in a master mix, as indicated in the experimental spreadsheet. Master mix was added directly to blood, along with antibodies against BCMA or BCMB72. After 30 minute incubation at room temperature, the plate with the blood was centrifuged at 1350 rpm for 3 minutes at 4° C. The supernatant plasma was discarded and the pellets were subjected to four consecutive rounds of RBC lysis, with 5 minute incubations between each wash. After lysis was complete, pellets were washed once with PBS and then stained in PBS with 1:200 Live/Dead near-IR stain and 1:50 anti-IgG4 PE (only for wells with BCMB72). The plates were further incubated for 15 minutes at room temperature. Later the samples were washed with 200 μl of FACS buffer and finally reconstituted in 150 μl of FACS buffer for analysis on LSRFortessa. Approximately 100,000 events were collected from each well. Analysis was done in FlowJo 7.6.

Figure 7:
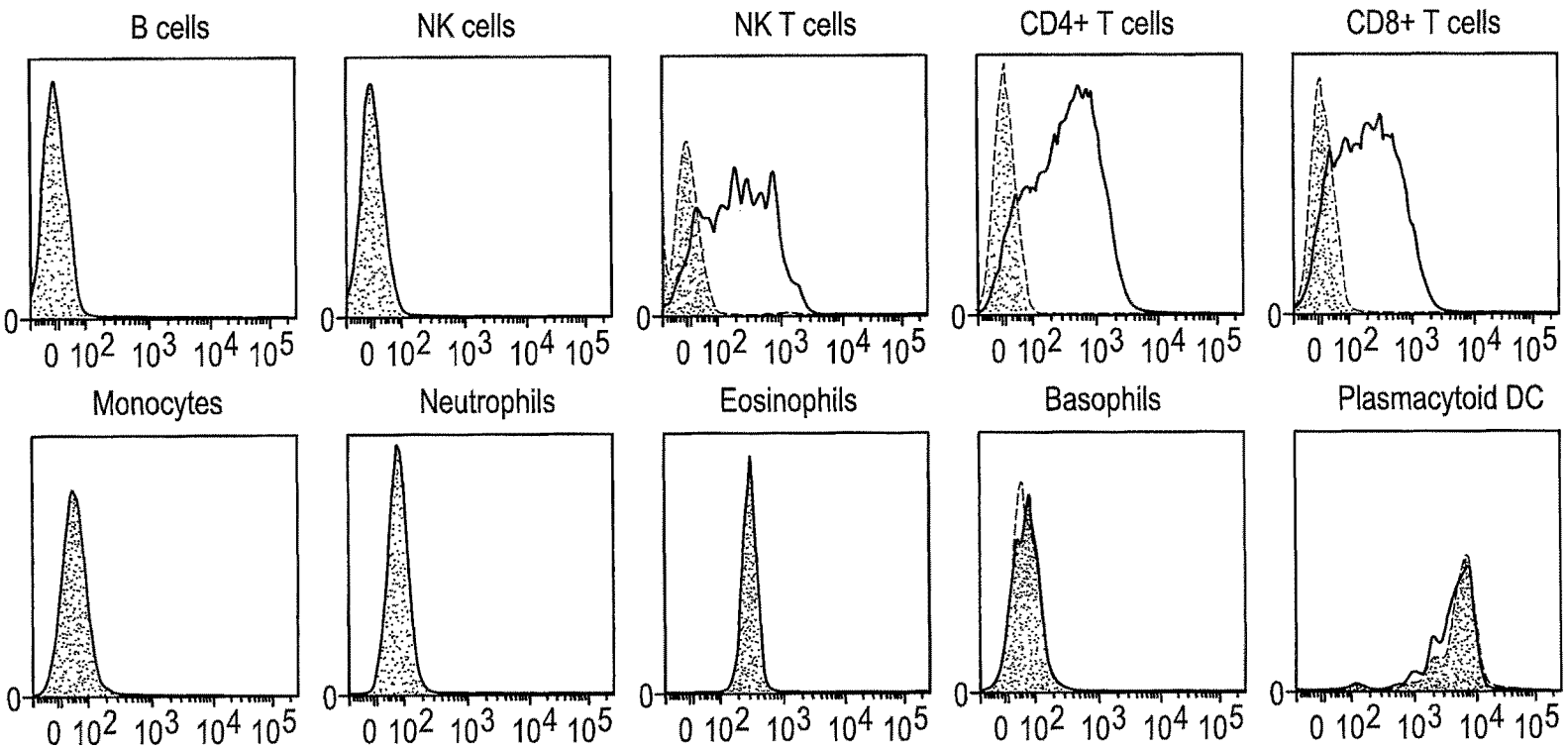
FIG. 7. BCMB72 binding profile in whole blood. Whole blood from three normal human donors was stained with monoclonal or polyclonal antibodies against BCMA or BCMB72. Gating analysis was performed to identify lymphocytes in the leukocyte population using standard cell specific markers. Staining intensity for one representative donor is shown in the panels, where solid black lines are antibodies of interest and dotted lines with filled gray are the corresponding isotype. No BMCA expression was observed on lymphocytes, monocytes, granulocytes or plasmacytoid DCs in three normal donors. BCMB72 showed binding to CD3+ T cells in all three donors with varying intensity between donors. BCMB72 did not bind to any other cell type tested in this assay.
Figure 10A:
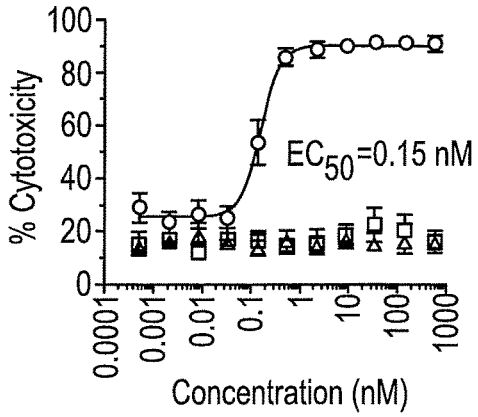
FIGS. 10A, 10B, 10C, 10D and 10E. T-cell mediated BCMB72-dependent cytotoxicity of various multiple myeloma cell lines. H929 (FIG. 10A), MM.1R (FIG. 10B), RPMI 8226 (FIG. 10C), U266 (FIG. 10D) and Mv4-11 (FIG. 10E) cells were subjected to the indicated antibody concentration in the presence of T cells from six normal donors (donor averages ±SEM are shown) and Fc blocker (2 mg/mL) for 48 hours. The $EC_{50}$ values are indicated on the graphs. Statistics analysis: In addition to the simple fact of model convergence, the width of the 95% confidence interval about the Log $EC_{50}$ is considered to evaluate adequacy of fit. (The confidence interval about Log $EC_{50}$ is used because it is symmetric; confidence intervals about the $EC_{50}$ itself are not.) An interval less than +/−2 (or a total 95% confidence interval width less than 4) is considered adequate.
Figure 10B:
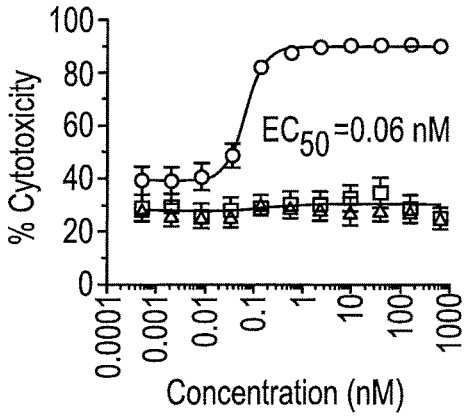
Figure 10C:
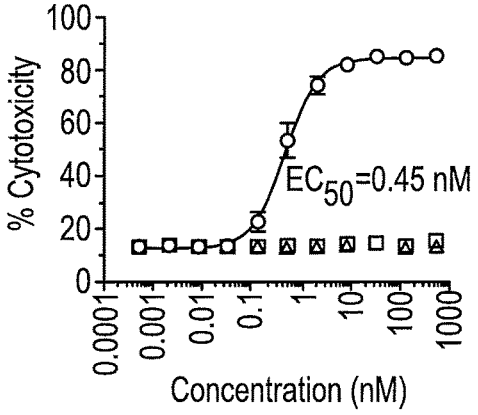
Figure 10D:
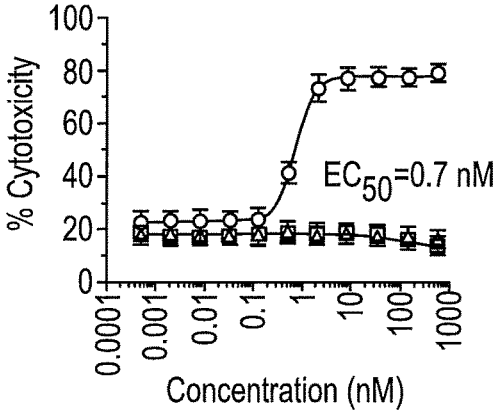
Figure 10E:
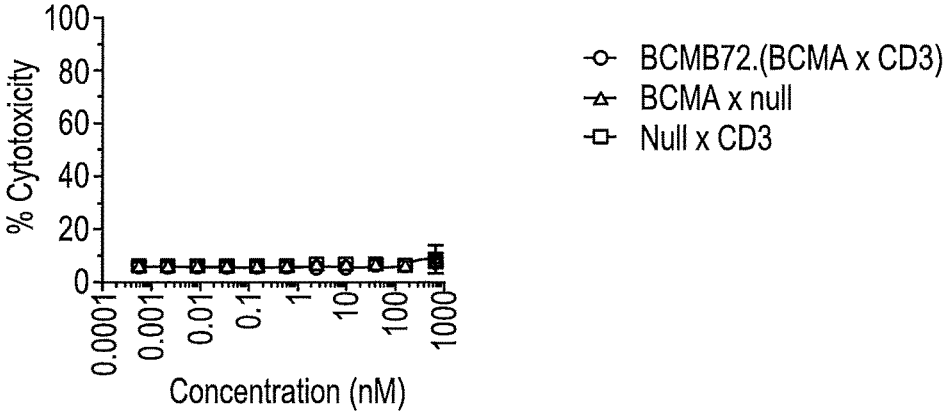

As shown in FIG. 7, no BMCA expression was observed on lymphocytes, monocytes, granulocytes or plasmacytoid DCs in three normal donors. BCMB72 showed binding to CD3+ T cells in all three donors with varying intensity between donors. BCMB72 did not bind to any other cell type tested in this assay.

Example 13: BCMB72 Effect on Cytokine Profile

The cytokine profile in the supernatant from the T cell mediated killing assays was assessed using BCMB72 and the control antibodies. T cells and antibodies were plated as in the T-cell mediated cytotoxicity assay (see Example 10). After 48 hours incubation, cell supernatants were harvested and different (10/30 Plex) cytokines were measured using an MSD based ELISA. Cytokine levels were expressed as pg/mL and graphing and fitting of data were done in GraphPad Prism 6 using nonlinear regression with variable slope (four parameters) function. The $EC_{50}$ values of six cytokines from RPMI8226 cell line using six T cell donors are shown in FIG. 13. The data show significant cytokine release resulting from T cell activation. Low/no cytokine release was observed with control antibodies (data not shown).

Example 14: Functional Comparison of HEK- and CHO-Produced (Transient & Stable Cell Lines) BCMB72 in T-Cell Activation and T-Cell Mediated Target Cell Killing Bispecific antibodies produced in different cells and under different modes of expression may vary in activity. Thus, the in vitro efficacy of BCMB72 produced in HEK (transient expression) or CHO cells (transient or stable expression) was evaluated.

BCMB72 was diluted to 800 μg/ml in PBS. As indicated in each experiment, the titration was prepared either in 3-fold or 4-fold serial dilutions in PBS in a 96-well U-bottom plate. The last column was left as PBS alone (vehicle control).

H929 target cells were cultured in antibiotic-free RPMI 1640 medium supplemented with GlutaMAX, 10% FBS and 25 mM HEPES (culture medium). On the set-up day (Day 1), cells were counted and 10 million cells were centrifuged at 1350 rpm for 3 minutes and the supernatants were discarded. CellTrace FCSE proliferation stain was reconstituted in 18 μl of sterile DMSO and 1 μl of the solution was diluted in 10 ml of sterile PBS. H929 cell pellet was resuspended in 1 ml of CFSE dilution and incubated at room temperature for 8 minutes hidden from direct light. After the incubation, 1 ml of HI FBS was added to cell suspension to quench the surplus CFSE. Cells were washed twice in 1640 RPMI with 10% FBS. After reconstitution in 10 ml of RPMI, cells were counted and cell viability was recoded in a spreadsheet. Cells were diluted to the indicated concentration and incubated at 37° C. until use.

T cells from normal donors were thawed in 37° C. water bath, after which the contents of the vial were transferred to a 50-ml conical vial and reconstituted in 15 ml of cold culture medium. Cells were then centrifuged at 1350 rpm at 4° C. for 3 minutes. The supernatants were discarded and cell pellets were reconstituted in 5 to 10 ml of culture medium. T cells were counted and reconstituted in culture medium to the appropriate concentration (see spreadsheet for each experiment).

H929 cells were added to wells, followed by T cells (5:1 Effector:Target ratio). In this set of studies no Fc blocker was used. After target and T cells were mixed, 20 μl of BCMB72 dilutions was added to each well. The plates were incubated at 37° C. with 5% $CO_2$ for 48 hours. After 2 days the plates containing cells were centrifuged and the supernatants were either discarded or stored for cytokine release assay. Cells were washed in 200 μl of PBS and incubated in 50 μl of near-IR Live/Dead stain (1:200 dilution) and anti-CD25 PE antibody (1:50 dilution) for 20 minutes at room temperature. Then, the cells were washed once in 200 μl of FACS buffer and finally reconstituted in 150 μl of FACS buffer. Cells were run by flow cytometry on the same day using FACSCanto II and analyzed in FlowJo 7.6 for target cytotoxicity (% target) and T cell activation CD25+ (% live T cells). Graphing and fitting of data were done in GraphPad Prism 6 using nonlinear regression with variable slope (four parameters) function and least squares method.

Figure 14A:
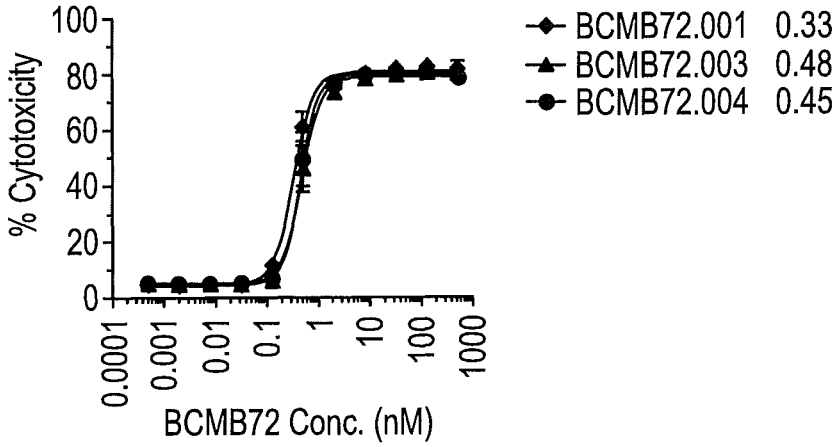
FIGS. 14A and 14B. T-cell mediated BCMB72-dependent cytotoxicity assay was performed using BCMA positive H929 cell line. Cells were subjected to BCMB72 at various concentrations in the presence of T cells from multiple normal donors (summary of three donors M7197, M5137 and M6457 is shown as representative) and Fc blocker (2 mg/mL) for 48 hours. The effector/target (E/T) ratio was 5:1.
Figure 14B:
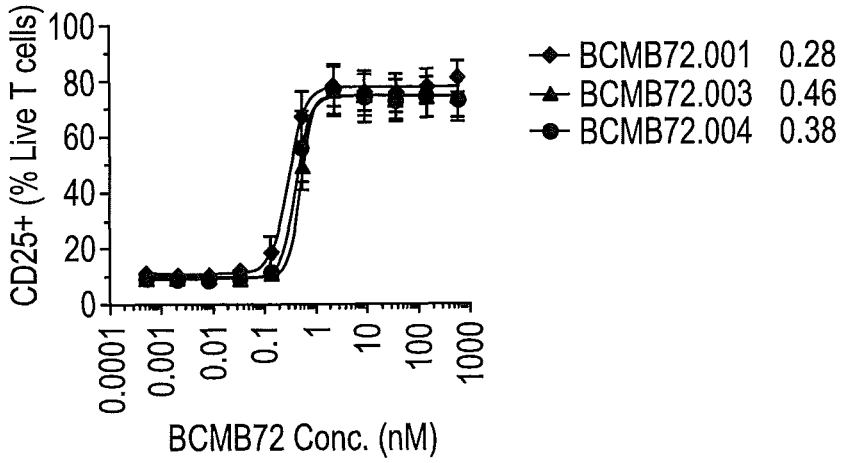

As seen in FIGS. 14A and 14B, BCMB72 produced in HEK cells and those produced in CHO cells perform virtually identically in T cell redirection assay in terms of cytotoxicity to target cells and stimulation to T cells. Maximal killing of 85% and T cell activation of 80% were generally achieved. Average $EC_{50}$ values for cytotoxicity were 0.29 nM for BCMB72 produced in HEK cells and 0.42-0.47 nM for BCMB72 produced in CHO cells. Average $EC_{50}$ values for T cell activation were 0.28 nM for BCMB72 produced in HEK cells and 0.37-0.41 nM for BCMB72 produced in CHO cells. Comparative analysis using Student's T-test showed no statistical significance between $EC_{50}$ values.

Example 15: P38 Signaling Activation by BCMB72

Both BAFF and APRIL bind to two receptors BCMA (B cell maturation antigen, TNFRSF 17) and TACI (transmembrane activator and CAML interactor, TNFRSF 13b). Engagement of BCMA activates JNK and P38 MAPK signaling pathway. It is possible that the BCMA×CD3 bispecific antibody, BCMB72, may exert an agonistic effect toward BCMA. This study included two parts. 1. Developing a simple western analysis assay to monitor the P38a MAPK changes in H929 or MM1.R cells after APRIL or BAFF treatment. 2. Using the newly developed assay to check whether BCMB72 has any agonistic effect toward BCMA.

Cell Treatment

H929 or MM1.R cells were seeded at 1.5e6/ml in serum free RPMI medium for 24 hr at 37° C. in the presence of 5% $CO_2$ prior to the treatment. On the day of the treatment, cells were spun down and resuspended in serum free RPMI at 1.5e6/ml. For time course assay, cells were aliquotted into 5 ml per tube for 10 tubes. Each tube of cells was treated with 1000 ng/ml of APRIL (R&D Systems cat#5860-AP-010) or 1000 ng/ml of BAFF (R&D Systems cat#2149-BF-010) for 0, 5, 15, 30 and 60 min, respectively at 37° C. in the presence of 5% $CO_2$. After incubation, cells were immediately pelleted and frozen in −80° C. for making cell lysate. For BCMB72 agonist effect assay, the H929 cell treatment groups were listed in Table 13. The BCMB72 agonist effect assay was conducted twice.

TABLE 13

Treatment groups for BCMB72 agonist effect assay

| Sample | Treatment (15 min) |
|---|---|
| 1 | APRIL 0 ng/ml |
| 2 | APRIL 1000 ng/ml |
| 3 | BAFF 0 ng/ml |
| 4 | BAFF 1000 ng/ml |
| 5 | BCMB72 0 ng/ml |
| 6 | BCMB72 10 ng/ml |
| 7 | BCMB72 100 ng/ml |
| 8 | BCMB72 1000 ng/ml |
| 9 | BCMB72 10000 ng/ml |

Cell Lysate Preparation for Simple Western Analysis

Cells were lysed with RIPA buffer, containing phosphatase and protease inhibitors. Protein concentration was measured on a SpectraMax Plus 384 microplate reader (Molecular Devices, Sunnyvale, Calif., USA) using BioRad DC Protein Assay (BioRad #500-0112) and bovine serum albumin standards.

Simple Western Analysis

Simple Western analyses were performed with Wes-Rabbit (12-230 KDa) Master kit (ProteinSimple # PS-MK01) according to the ProteinSimple user manual. In brief, cell lysate samples were mixed with a master mix to a final concentration of 1× sample buffer, 1× fluorescent molecular weight marks, and 40 mM dithiothreitol (DTT) and then heated at 95° C. for 5 min. The samples, blocking reagent, primary antibodies phosphor-p38 MAPK (ThermoFisher: VWR# MA5-15182) or Actin-beta (Cell Signaling, #8457S), HRP-conjugated secondary antibodies, chemiluminescent substrate, and separation and stacking matrices were also dispensed to designated wells in a Simple Wes microplates, After plate loading, the separation electrophoresis and immunodetection steps took place in the capillary system and were fully automated. During electrophoresis, proteins were separated on the basis of molecular weight through the stacking and separation matrices and immobilized on the capillary wall using proprietary photoactivated capture chemistry. Primary antibodies were diluted 1:50 with antibody diluent II (ProteinSimple #042-203). Target proteins were immunoprobed with primary antibodies for 60 min, followed by HRP-conjugated secondary antibodies. Simon-simple Western analysis is carried out at room temperature, and instrument default settings were used. The digital image was analyzed with Compass software (ProteinSimple), and the quantified data of the detected protein were reported as molecular weight, signal/peak intensity, and peak area.

Results

Figure 15:
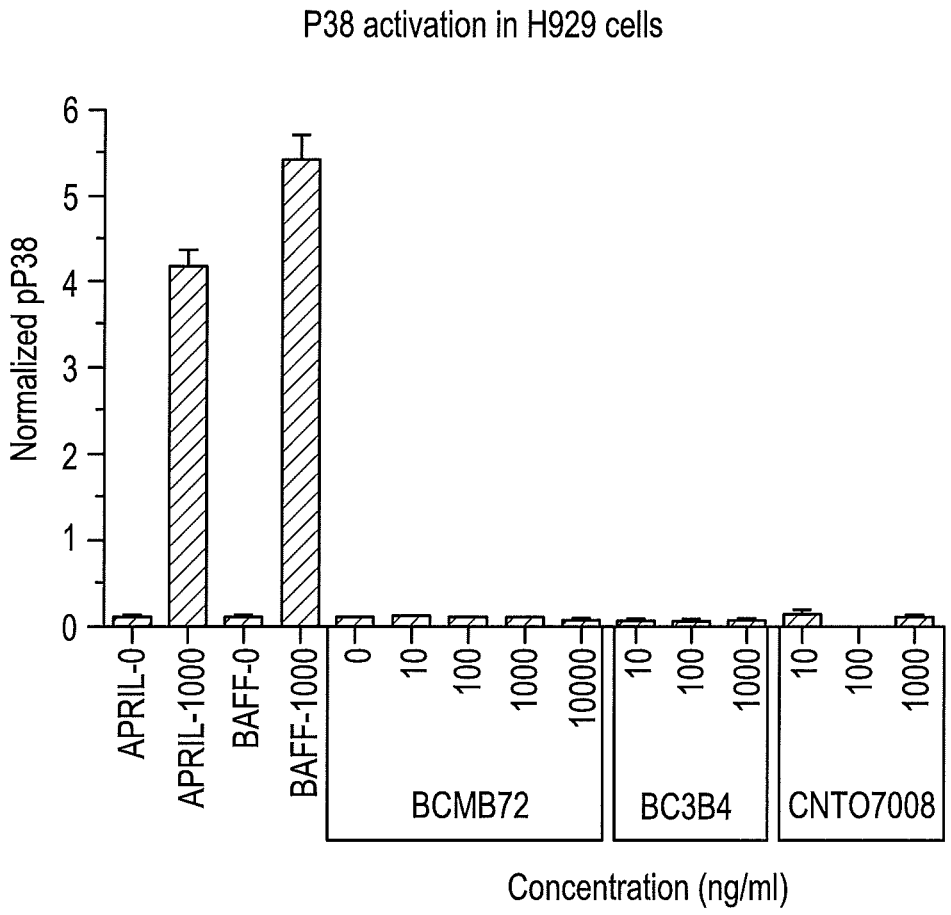
FIG. 15. H929 cells were treated with BCMB72 (BCMA×CD3) and control antibodies (BCMA×null and null×CD3) for 30 minutes at the doses indicated on the X-axis in the above graph and total protein was analyzed using Simple Western analysis method according to the standard protocol as per ProteinSimple user manual. Data were normalized using actin as a housekeeping gene and ratios were plotted on Y-axis. APRIL and BAFF induced phosphorylation of P38 as expected and the antibodies have no stimulatory effect at any concentration tested.
Figure 16A:
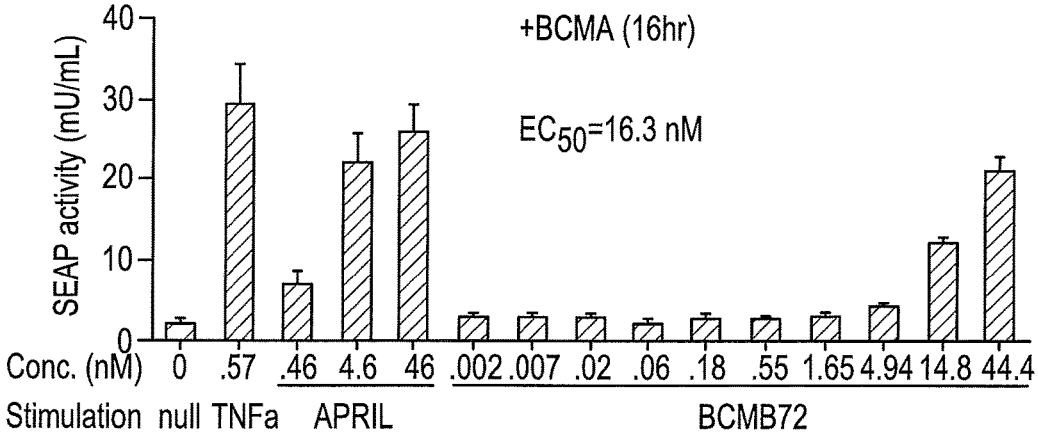
FIGS. 16A, 16B, 16C, 16D, 16E and 16F. HEK-NFκB cells expressing BCMA (FIG. 16A, FIG. 16C and FIG. 16E) or parent cells (FIG. 16B, FIG. 16D and FIG. 16F) were stimulated with TNFα and various concentrations of APRIL or BCMB72. Three time points, 16 hr.
Figure 16B:
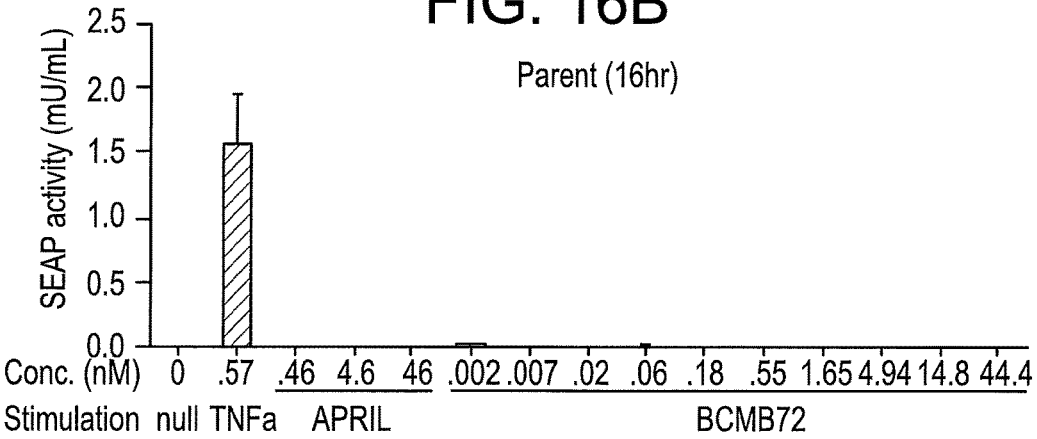
Figure 16C:
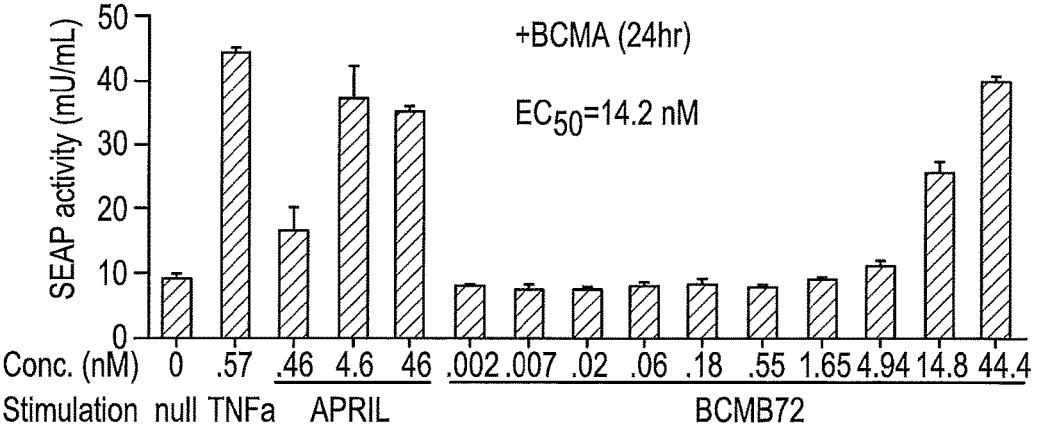
Figure 16D:
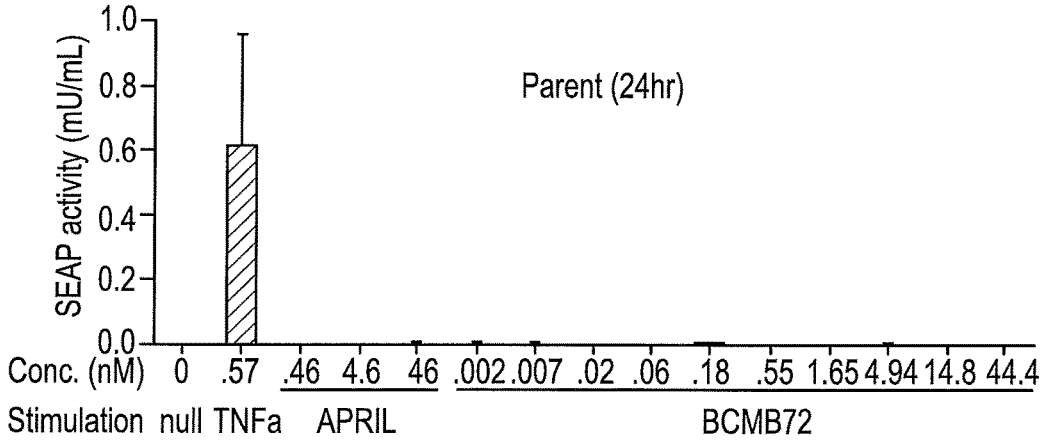
Figure 16E:
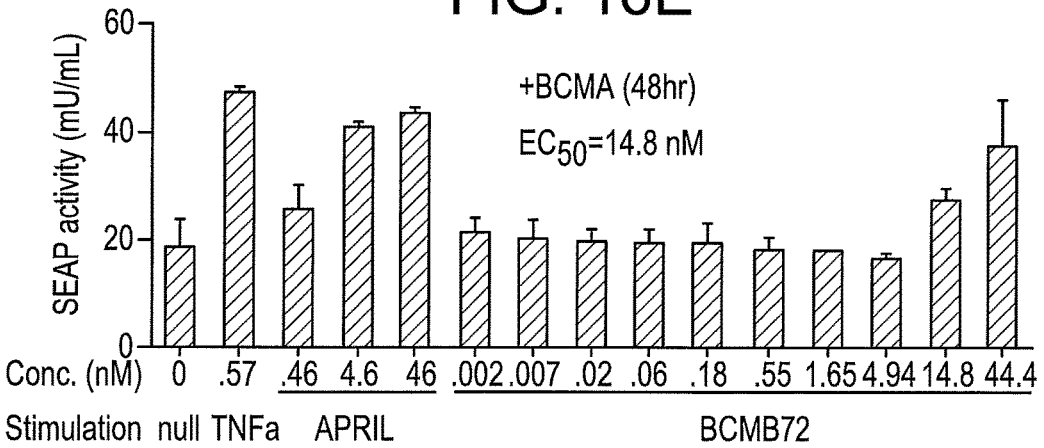
Figure 16F:
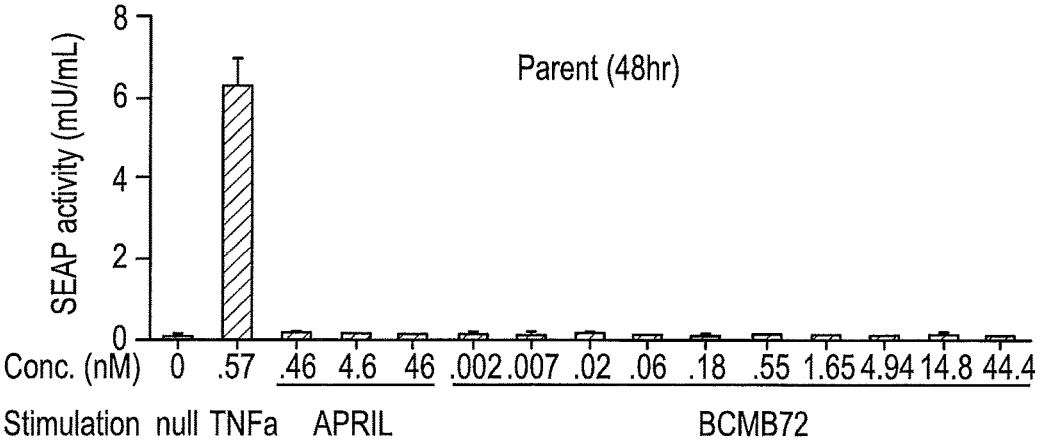

Based on the information obtained from the time course study, a BCMB72 agonist assay was performed with H929 cells using 15 min incubation end point. p38 MAPK signals were normalized by human beta Actin signals. The mean of normalized p38 MAPK signals from two assays are shown in FIG. 15. The BCMB72 agonist assay demonstrated that BCMB72 has no agonistic effect toward BCMA in H929 cells.

Example 16: NFκB Signaling by BCMB72

BCMA is a surface receptor that can elicit NF-κB signaling in response to endogenous ligands. The effect of BCMB72 binding to BCMA on NF-κB pathway activation was evaluated using BCMA-expressing reporter cell line that expresses alkaline phosphatase (SEAP) under NFκB promoter.

Cells were cultured in DMEM medium supplemented with GlutaMAX and 10% FBS (culture media). In the evening prior to experiment cells were harvested by trypsinization (5 minutes in pre-warmed 0.25% Trypsin at 37° C.) and washed in 30 ml of culture media. Cells were then centrifuged at 1,000 rpm for 5 minutes at 4° C. and reconstituted in serum-free DMEM (with GlutaMax) at 2.5×10^5 cells/ml. 5×10^4 cells were added to wells of a 96-well flat bottom plate and incubated at 37° C. for 16 hours.

The next morning, various stimulatory reagents (TNFα, APRIL, BCMB72) were added to the corresponding wells (see experimental plate maps) and plates were incubated at 37° C. for additional 16 hr, 24 hr or 48 hr, which represented early, middle and late time points of signaling, respectively. After each time point, 10 μl of conditioned culture media was collected from wells, transferred to a 96-well solid plate provided in the SEAP kit (Cayman, 600272), and covered with the lid. SEAP standards were prepared by diluting bulk standard (5 U/ml) 1:10 in serum-free DMEM (with GlutaMax) and then preparing 1:2 serial dilutions; the dilution range is 50-0.78 mU/ml. The plate with the samples was incubated at 65° C. for 30 minutes to inactivate endogenous alkaline phosphatase; SEAP expressed in this assay is stable under these incubation conditions. 10 μl of standard dilutions were added to the appropriate wells after the plates were incubated at room temperature. 50 μl of substrate solution was added to all wells and the samples were briefly agitated to distribute the solution in the wells. Samples were incubated for 20-30 minutes and chemiluminescence was assessed using PerkinElmer EnVision 2104 Multilabel Reader. All luminescence readings were converted to activity unit concentrations based on standard curve and the values were analyzed in Microsoft Excel 2010 and imported to Graph Prism 6 for graphical analysis.

FIGS. 16A, 16B, 16C, 16D, 16E and 16F demonstrates that whereas APRIL was able to stimulate BCMA at concentrations as low as 0.46 nM, in general, BCMB72 did not activate NF-κB pathway in BCMA-transduced cells at concentrations below 10 nM. Modest BCMB72-dependent activation was observed at high (44-133 nM) BCMB72 concentrations.

Example 17: Effect of Exogenous Addition of Extracellular Domain of BCMA on T Cells Activation in the Absence of Target Cells BCMA extracellular domain (ECD) can form trimers in solution. Therefore, the possibility exists that multiple bispecific antibodies can bind to BCMA ECD trimers and cross-link TCR complexes in the absence of target cells. This could in turn activate T cells in a target-independent fashion. This study examined whether exogenously added ECD of BCMA can trigger T cell activation at the level of CD25 expression without interaction with target cells.

BCMB72 (BCMA×CD3) and a control (null×CD3) were diluted to 800 μg/ml in PBS. The titration was prepared in 3-fold serial dilutions in PBS in a 96-well U-bottom plate. The last column was left as PBS alone (vehicle control).

Soluble BCMA ECD (sBCMA) was diluted to 36 μg/ml (6.67 μM) in PBS. The titration was prepared in 3-fold serial dilutions in PBS in a 96-well U-bottom plate. The top well was left as PBS alone (vehicle control).

Pan T cells from normal donors were thawed in 37° C. water bath, after which the contents of the freeze vials were transferred to 50-ml conical vials and reconstituted in 30 ml of cold culture medium. Cells were then centrifuged at 1350 rpm at 4° C. for 3 minutes. The supernatants were discarded and cell pellets were reconstituted in 10 ml of culture medium. T cells were counted and the viability was recorded. Cells were then reconstituted in culture medium to 0.525×10^6/ml.

1×10^5 T cells (190 μl) were added to the wells, followed by 5 μl of sBCMA dilutions and 5 μl of BCMB72 dilutions. Plates were incubated at 37° C. with 5% $CO_2$ for 48 hours.

After two day, the plates were centrifuged at 1500 rpm for 3 minutes at 4° C. and supernatants were discarded. Cell pellets were washed in 200 μl of PBS and incubated in 50 μl of near-IR Live/Dead stain (1:200 dilution) and anti-CD25 PE antibody (1:50 dilution) for 20 minutes at room temperature. Then, the cells were washed once in 200 μl of FACS buffer and finally reconstituted in 150 μl of FACS buffer. Cells were analyzed using FACSCanto II and FlowJo 7.6 for T cell activation CD25+ (% live T cells). Graphing and fitting of data were done in GraphPad Prism 6 using non-linear regression with least squares fitting method.

Figure 17A:
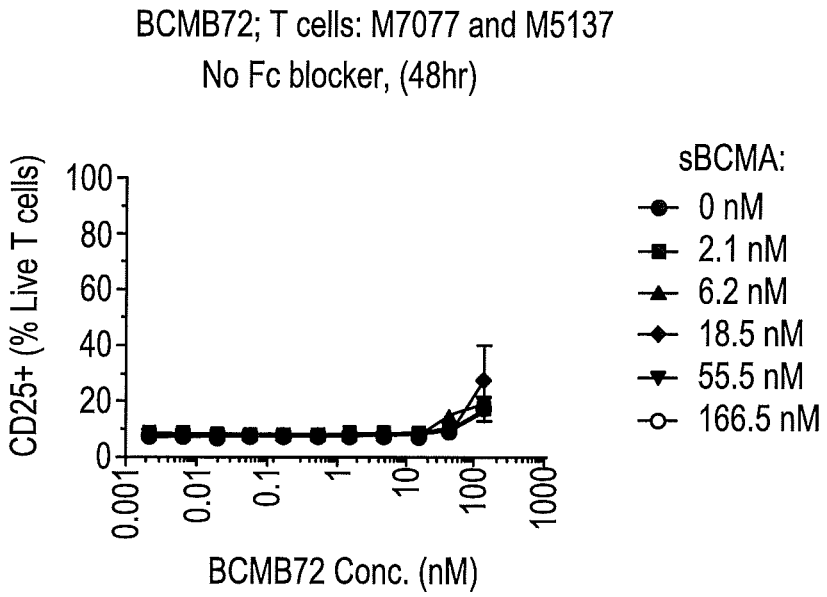
FIGS. 17A and 17B. T cells do not exhibit sBCMA-mediated and BCMB72-dependent activation. BCMB72 (FIG. 17A) and a null×CD3 control antibody (FIG. 17B) were titrated in with the T cells from two normal donors (M7077 and M5137) in the presence of various doses of soluble BCMA ECD. Data: Mean±SEM.
Figure 17B:
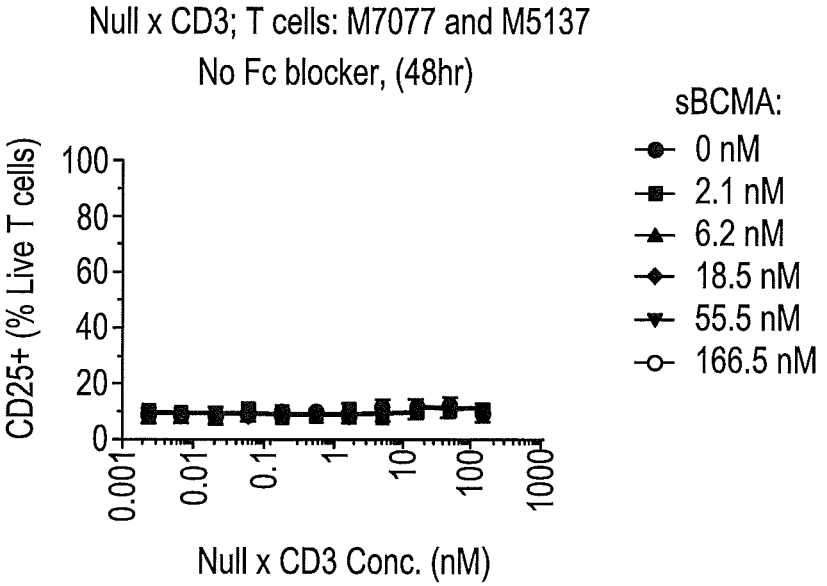

T cells from normal donors did not exhibit sBCMA ECD-mediated activation in the presence of BCMB72. Weak activation of a small percentage of T cells (10-15%) was observed at high concentrations (>40 nM) of BCMB72 in a sBCMA-independent fashion (FIGS. 17A and 17B).

Example 18: Effect of Soluble ECD of BCMA, APRIL, and BAFF on T Cell Activation and BCMB72-Dependent Cytotoxicity Soluble BCMA ECD can serve as a sink for BCMA×CD3 antibodies, while APRIL and BAFF can be competitive inhibitors of interaction between surface receptor and BCMA×CD3 antibodies. The effects of soluble BCMA ECD and endogenous liganda APRIL and BAFF on in vitro cytotoxic potency of BCMB72-dependent cell killing were assessed in T cell redirection assays using immortalized cell line H929 and pan T cells from normal donor M7077.

BCMB72 was diluted to 800 μg/ml in PBS. The titration was prepared in 3-fold serial dilutions in PBS in a 96-well U-bottom plate. The last column was left as PBS alone (vehicle control). Soluble BCMA ECD was diluted to 9 μg/ml and APRIL and BAFF were diluted to 10 μg/ml. The titrations for both reagents were prepared in 3-fold serial dilutions in PBS in a 96-well U-bottom plate.

H929 target cells were cultured in antibiotic-free RPMI 1640 medium supplemented with GlutaMAX, 10% FBS and 25 mM HEPES (culture medium). On the set-up day (Day 1), target cells were counted and 10 million cells were centrifuged at 1350 rpm for 3 minutes after which, the supernatants were discarded. CellTrace FCSE proliferation stain was reconstituted in 18 μl of sterile DMSO and 1 μl of the solution was diluted in 10 ml of sterile PBS. Cell pellets were resuspended in 1 ml of CFSE dilution and incubated at room temperature for 8 minutes hidden from direct light. After the incubation, 1 ml of HI FBS was added to cell suspension to quench the surplus CFSE. Cells were washed twice in RPMI-1640 with 10% FBS. After reconstitution in 10 ml of RPMI, cells were counted and cell viability was recoded in a spreadsheet. Cells were diluted to 2.2×10^5/ml and incubated at 37° C. until use.

Pan T cells from normal donor were thawed in 37° C. water bath, after which the contents of the freeze vials were transferred to 50-ml conical vials and reconstituted in 30 ml of cold culture medium. Cells were then centrifuged at 1350 rpm at 4° C. for 3 minutes. The supernatants were discarded and cell pellets were reconstituted in 10 ml of culture medium. T cells were counted and the viability was recorded. Cells were then reconstituted in culture medium to 1.1×10^6/ml.

2×10^5 of H929 cells were added to wells of a 96-well U-bottom plate; no incubation with Fc blocker was necessary in this study. 1×10^5 T cells were added to the wells (5:1 Effector:Target ratio). After target and T cells were mixed, 20 μl of either sBCMA, APRIL or BAFF were added to the wells followed by 5 μl of antibody dilutions. Plates were incubated at 37° C. with 5% $CO_2$ for 48 hours.

After 2 days, the plates were centrifuged at 1500 rpm for 3 minutes at 4° C. and the supernatants were discarded. Cells were washed in 200 μl of PBS and incubated in 50 μl of near-IR Live/Dead stain (1:200 dilution) and anti-CD25 PE antibody (1:50 dilution) for 20 minutes at room temperature. Then, the cells were washed once in 200 μl of FACS buffer and finally reconstituted in 150 μl of FACS buffer. Cells were analyzed using FACSCanto II and FlowJo 7.6 for target cytotoxicity (% target) and T cell activation CD25+ (% live T cells). Graphing and fitting of data were done in GraphPad Prism 6 using nonlinear regression with variable slope (four parameters) function using least squares method.

Figure 18A:
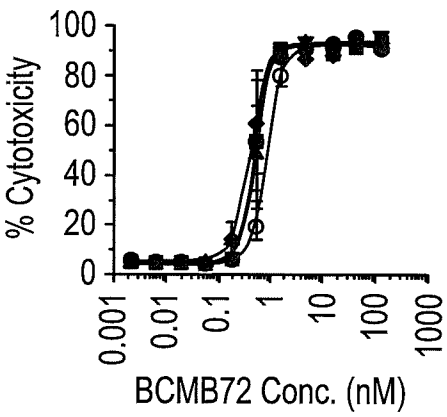
FIGS. 18A, 18B, 18C, 18D, 18E and 18F. Effect of soluble factors, sBCMA, APRIL and BAFF on T cell activation and T cell mediated cytotoxic potential of BCMB72 in H929 cells. Cells were subjected to a killing assay for 48 hours using donor T cells (M7077 & M6521) and BCMB72. Target cytotoxicity is depicted in the graphs on the left and T cell activation is shown in the graphs on the right (n=2). The $EC_{50}$ values for each treatment are indicated in the legends. Cell cytotoxicity in the presence of sBCMA (FIG. 18A), APRIL (FIG. 18B) and BAFF (FIG. 18C) are shown. T cell activation in the presence of sBCMA (FIG. 18D), APRIL (FIG. 18E) and BAFF (FIG. 18F) are shown. Data: Mean±SEM.
Figure 18B:
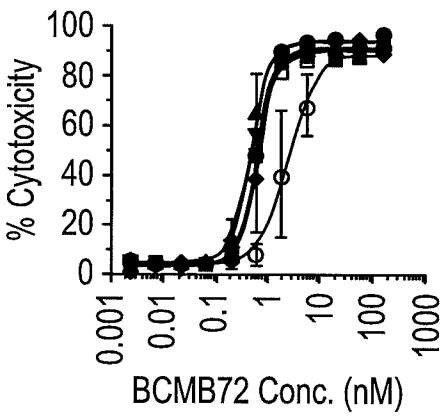
Figure 18C:
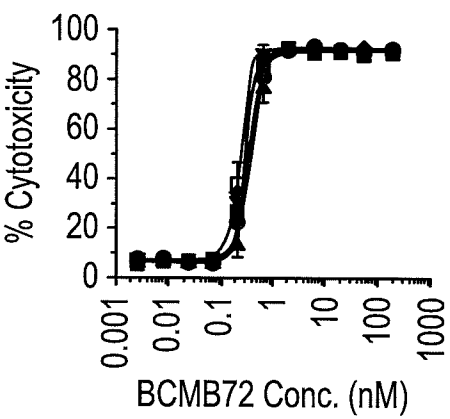
Figure 18D:
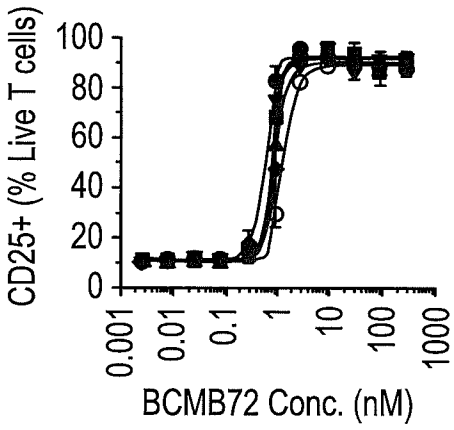
Figure 18E:
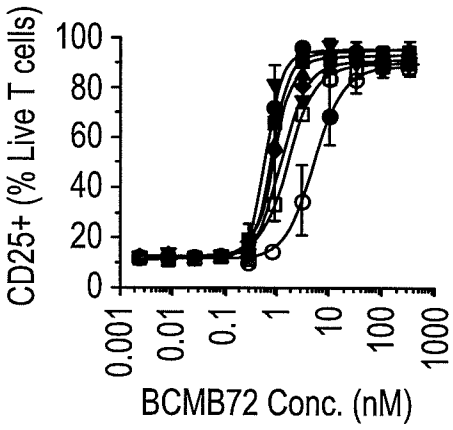
Figure 18F:
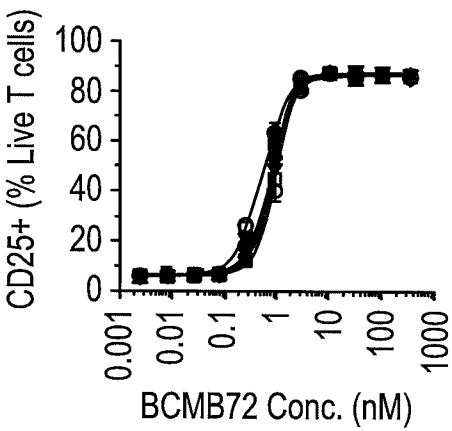

BCMB72 was able to exert cytotoxicity on H929 cells in the presence of soluble BCMA ECD, with only minor effect (2-fold increase) on $EC_{50}$ at high doses (>160 nM) of sBCMA ECD; T cell activation was similarly affected (see FIGS. 18A and 18D). APRIL increased the $EC_{50}$ values for cell cytotoxicity and T cell activation six-fold at high doses (46 nM), while minimally affecting the assay at lower doses (see FIGS. 18B and 18E). Maximal killing was not affected by sBCMA or APRIL. In contrast, exogenous BAFF had no impact on BCMB72-mediated cytotoxicity at concentrations up to 51 nM (see FIG. 18C). The T cell activation potential in all cases correlated well with the killing data, as expected (see FIG. 18F).

Example 19: Competition of BCMB72, APRIL and BAFF for Binding to BCMA In Vitro

The two TNF ligands, APRIL and BAFF can bind to BCMA and induce a signaling cascade leading to cell survival and proliferation. The extracellular domain of BCMA is a short 54 amino acid fragment that binds to these two ligands as well as the antibodies raised against this motif. Here, the competitive nature of these ligands against BCMB72 was assessed.

The assay was setup in an ELISA based format. In preparation for the competition assay, BCMA-Fc was to be labeled with MSD SulfoTag. 50 ug vial of BCMA-Fc was reconstituted in 500 uL PBS to yield 0.1 mg/mL (3.125 uM monomer). 150 nmol NHS-sulfoTag was dissolved in 50 uL water to yield 3 mM solution. 5.2 uL 3 mM NHS-SulfoTag (15.6 nmol) was added to 500 uL BCMA-Fc (1.56 nmol monomer) for a 10× excess labeling reaction. Reaction was left for 2 hr at RT in the dark. 50 uL 1M tris was added to quench the unreacted NHS. Excess Sulfotag and tris was removed by buffer exchange over PBS equilibrated 2 mL 7 k MWCO Zeba spin column. Final volume was ~630 uL, therefore, final SulfoTag-BCMA-Fc is used as 2.5 uM.

For the competition assay, anti-BAFF (100 ug) and anti-APRIL (100 ug) were reconstituted in 200 uL PBS to yield 0.5 mg/mL stock solutions. 30 uL (6 ug) of anti-APRIL and anti-BAFF were each diluted in 2.97 mL PBS to yield 2 ug/mL solutions. To every well of a 96 well MSD high bind plate. 25 uL 2 ug/mL anti-APRIL was added. To every well of a second 96 well MSD high bind plate, 25 uL 2 ug/mL anti-BAFF was added. Plates were kept at 4 C overnight to immobilize antibodies. Plates coated with anti-APRIL and anti-BAFF were dumped, and 300 uL/well SuperBlock added. After 1 hr at RT of blocking, plates were washed 3× with PBS-T. 10 ug of each recombinant APRIL and BAFF were resuspended in 100 uL PBS to yield 0.1 mg/mL solutions. 3 mL 2 ug/mL solutions of each APRIL and BAFF were made by diluting 60 uL freshly reconstituted protein in 2.94 mL SuperBlock. 25 uL 2 ug/mL APRIL was added to each well of anti-APRIL coated plate, and 25 uL 2 ug/mL BAFF was added to each well of anti-BAFF coated plate. After 1 hr capture at RT, plates were washed 3× with PBS-T. 500 ug anti-BCMA (R&D Sys Mab193) was reconstituted in 1 mL PBS to yield stock solution of 0.5 mg/mL (3.3 uM). Anti-BCMA Mab193, BCMB72.004, and a control antibody (null×CD3), were diluted to 1 uM in superblock. An 11 pt threefold serial dilution series was prepared by mixing 100 uL antibody in 200 uL SuperBlock. 6 mL 30 nM SulfoTag-BCMA-FC was prepared by diluting 72 uL protein from above in 5.928 mL SuperBlock. 25 uL each antibody from step 11 was added to each well of the APRIL/BAFF captured plates according to plate map below in FIGS. 1A and 1B. 25 uL 30 nM Sulfotag-BCMA-Fc was added to each well of both plates. After 1 hr at RT, plates were washed 3× with PBS-T. 150 uL 1×MSD read buffer T was added to every well, and plates scanned in sector 6000 imager. The experiment was repeated exactly as described above to give a second independent set of results.

Figure 19A:
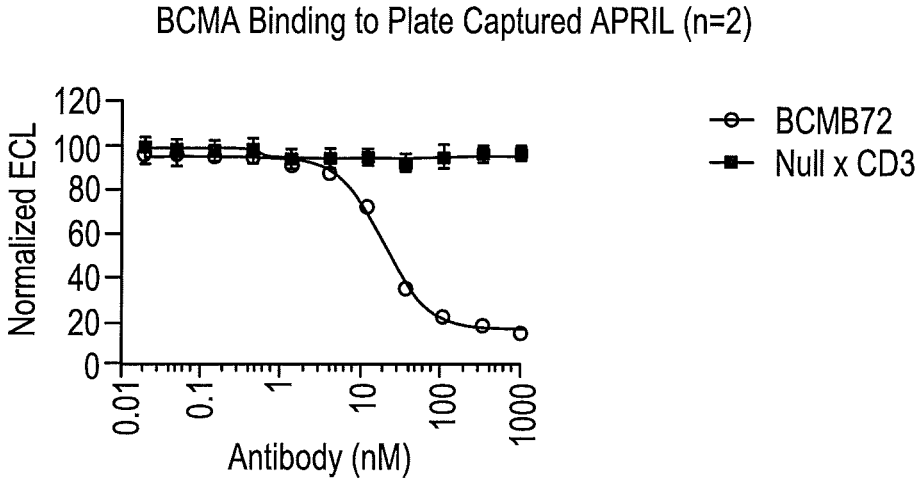
FIGS. 19A and 19B. Signals from two independent experiments were normalized to maximum signal of BCMA-Fc binding to APRIl and BAFF in the absence of competing antibodies. BCMA binding to APRIL (FIG. 19A) and BAFF (FIG. 19B) is plotted as a function of BCMB72 and control antibody (null×CD3) concentration.
Figure 19B:
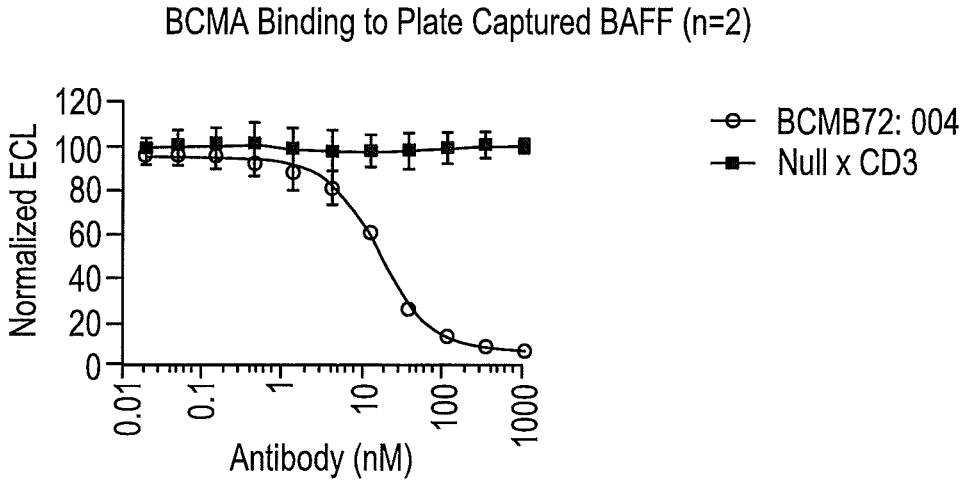
Figure 20A:
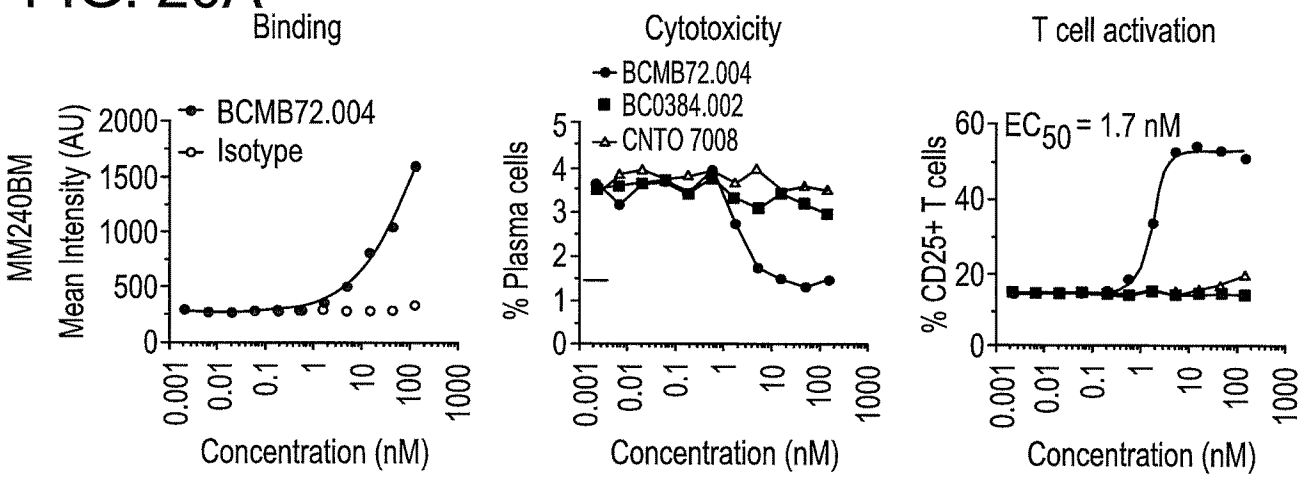
FIGS. 20A, 20B, 20C, 20D and 20E. Cytotoxic potency of BCMB72 against human primary MM plasma cells. Frozen bone marrow-derived mononuclear cells from five different patients (MM240BM (FIG. 20A), MM259BM (FIG. 20B), MM270BM (FIG. 20C), MM276BM (FIG. 20D) and MM277BM (FIG. 20E)) were used to assess BCMB72 binding, compared to IgG4 isotype (CNTO 9412, left panel) control, plasma cell cytotoxicity (middle) and T cell activation (right). For the cytotoxicity assay, T cells from the M7077 normal healthy donor were exogenously added to patient BMMC samples and incubated with BCMB72 (BCMA×CD3), BC3B4 (BCMA×null) or CNTO 7008 (null×CD3) for 48 hours. BCMB72 binds to plasma cells in a dose dependent manner to all donor samples and the mean fluorescence intensities were recorded on the Y-axis. Note the loss of live plasma cells (CD138) and the concomitant upregulation of CD25 on T cells in response to BCMB72 treatment. The $EC_{50}$ values for T cell activation are indicated on the graphs.
Figure 20B:
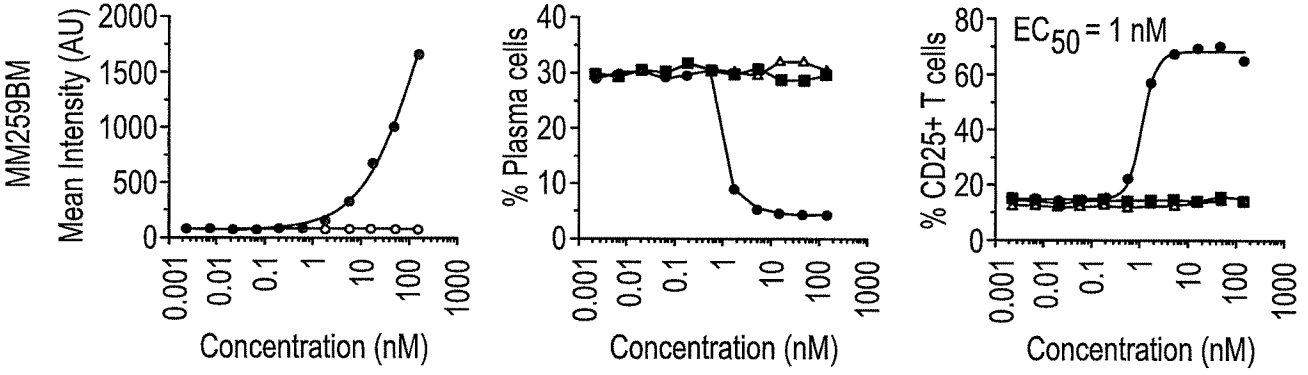
Figure 20C:
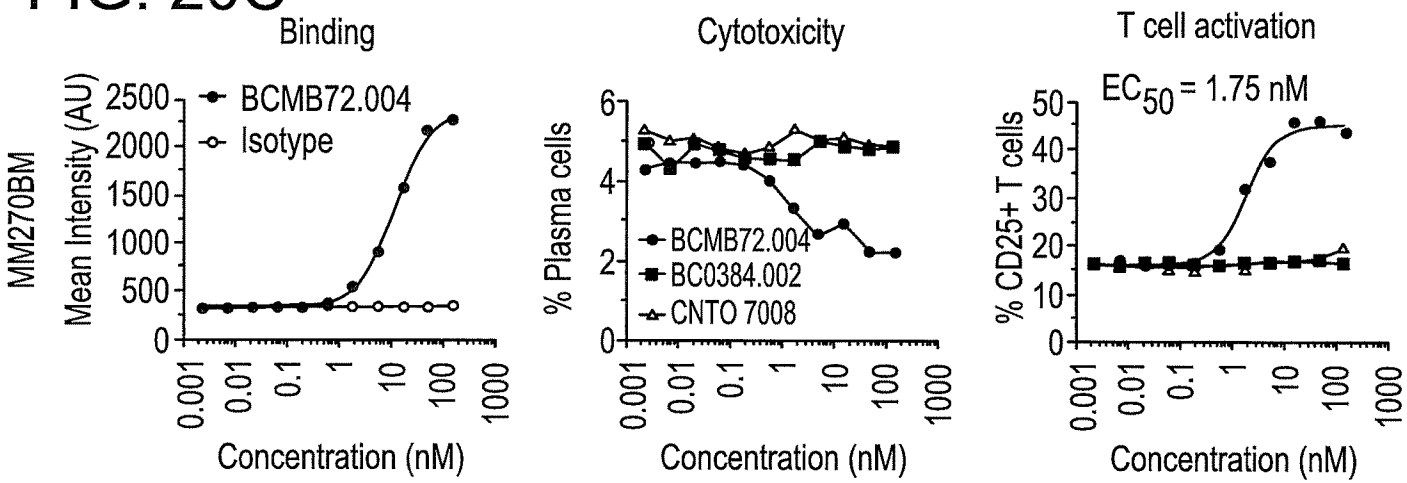
Figure 20D:
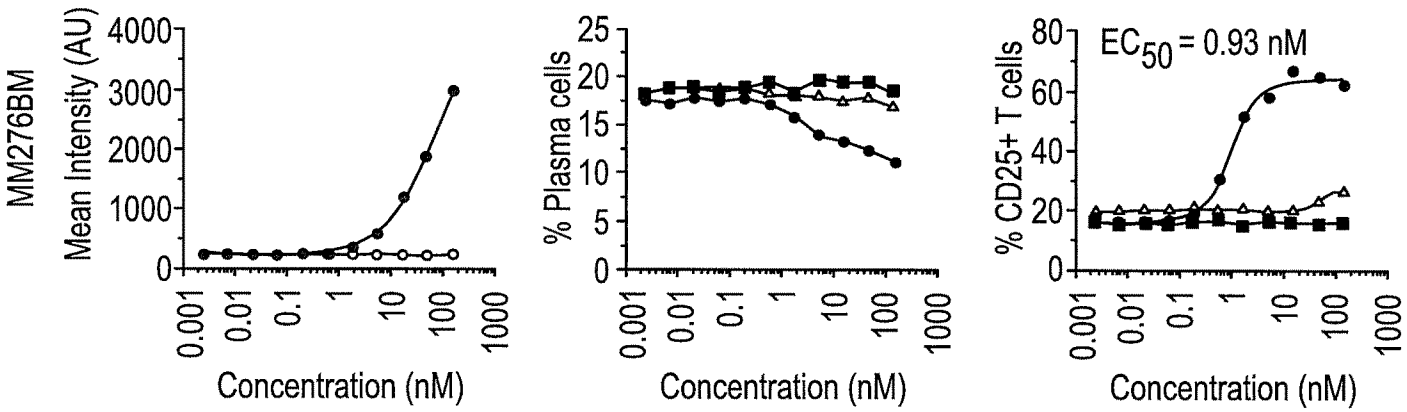
Figure 20E:
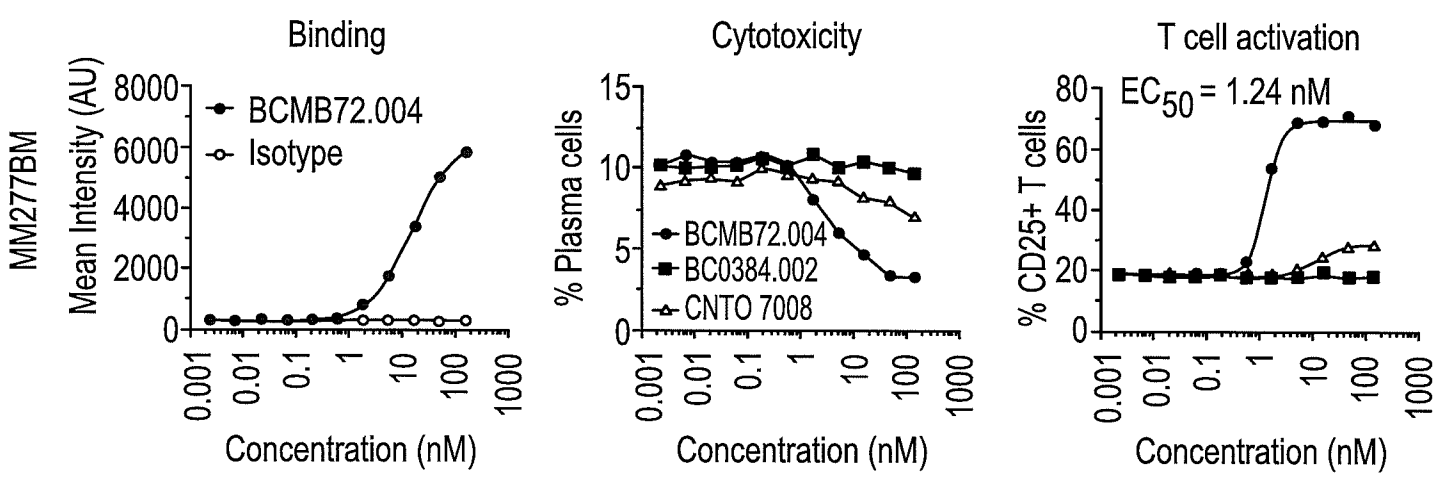

As can be seen in FIGS. 19A and 19B, when incubated with increasing amounts of BCMB72 but not the control antibody (null×CD3), BCMA-Fc protein was prevented from binding plate-bound APRIL and BAFF. The observation is consistent between two independent experiments, each with three replicates.

Example 20: BCMB72 Binding and Cytotoxicity of Multiple Myeloma Patient Bone Marrow CD138 Positive Cells To evaluate the potency of BCMB72 in primary samples from multiple myeloma patients, we tested this antibody in a cytotoxic killing assay using frozen bone marrow multiple myeloma samples from 5 patients and T cells from healthy donors. Antibody binding and T cell activation potential were also measured.

BCMB72 Binding Assay

100 μl of cell suspension was aliquotted per well in a 96 well U-Bottom plate, followed by 95 μl of culture medium. Then 5 μl of serial dilutions of BCMB72 or controls were added to the wells and the plate was incubated for 1 hour at 4° C. After staining, cells were centrifuged at 1,200 rpm for 3 minutes and washed once in 200 μl of PBS. Cells were centrifuged once more; supernatants were discarded after which, the pellets were reconstituted in 50 μl of near-IR Live/Dead stain (1:200 dilution), anti-human IgG4 Fc PE antibody (1:50 dilution), anti-CD138 (MI15 1:50 and DL-101 1:50 dilutions) and incubated for 20 minutes at room temperature in the dark. Cells were then centrifuged and washed in 200 μl of FACS buffer and finally reconstituted in 150 μl of FACS buffer. Samples were analyzed using FACSCanto II and FlowJo 7.6 for BCMB72 binding intensity on CD138+ MNCs. Fitting of data was done in GraphPad Prism 6 using nonlinear regression with variable slope (four parameters) function using least squares method.

T Cell Redirection Assay

1×10^5 target cells were added to wells of a 96-well U-bottom plate, followed by 1×10^5 T cells (5:1 Effector: Target approximate ratio, provided average 20% plasma cell count in bone marrow-derived mast cells). After target and T cells were mixed, 5 μl of BCMB72 dilutions were added to each well. The plates were incubated at 37° C. with 5% $CO_2$ for 48 hours.

Two days later, the plates were centrifuged and supernatants were discarded. Cells were washed in 200 μl of PBS and incubated in 50 μl PBS with near-IR Live/Dead stain (1:200 dilution), anti-CD138 (MI15 1:50 and DL-101 1:50 dilutions), anti-TCR α/β (1:50 dilution) and anti-CD25 PE (1:50 dilution) for 20 minutes at room temperature. Then, the cells were washed once in 200 μl of FACS buffer and finally reconstituted in 150 μl of FACS buffer. Cells were analyzed using FACSCanto II and FlowJo 7.6 for plasma cell cytotoxicity (% dead CD138+ cells) and T cell activation CD25+ (% live T cells). Graphing and fitting of data were done in GraphPad Prism 6 using nonlinear regression with variable slope (four parameters) function using least squares method.

Results

FIGS. 20A, 20B, 20C, 20D and 20E shows that BCMB72 binds and induces killing of all patient samples in a dose dependent manner after 48 h as evidenced by the loss of $CD138^+$ plasma cells. T cell activation data correlates well with the killing data as expected. Average $EC_{50}$ for T cell activation was in the 1 nM range. These data confirm that BCMB72 can kill primary multiple myeloma bone marrow cells in vitro.

Figure 21:
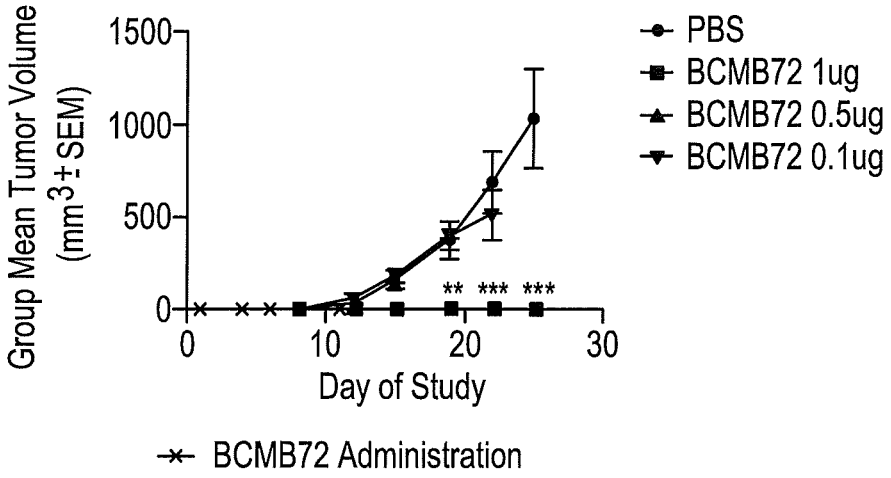
FIG. 21. BCMB72 in vivo efficacy in H929 prophylactic model.

Example 21: Anti-Tumor Efficacy of BCMB72 in Tumorigenesis Prevention of H929 Human Multiple Myeloma Xenografts in PBMC-Humanized NSG Mice This study evaluated the efficacy of BCMB72 in preventing tumorigenesis of H929 human multiple myeloma (MM) xenografts in PBMC (peripheral blood mononuclear cells)-humanized NSG (NOD SCID Gamma) mice. The NSG mouse is an immunecompromised strain lacking mature functional T, B and natural killer (NK) cells. Age matched female NSG mice were intravenously injected with $1\times10^7$ human PBMC on study day −7. On day 1 post PBMC inoculation, each mouse was subcutaneously (sc) implanted with H929 human MM cells ($5\times10^6$ cells in 200 μL PBS) on the right hind dorsal flank, followed by intravenous (IV) administration of PBS and BCMB72 0.1 μg (0.005 mg/kg), 0.5 μg (0.025 mg/kg) and 1 μg (0.05 mg/kg) per animal. The PBS control and BCMB72 were administered every other day or every three days for a total of five treatments. H929 sc tumors were detectable in the PBS and 0.1 μg BCMB72 treated groups as early as day 8 post tumor cell implant. Tumors from these two groups continued to grow until the mean tumor volumes were >500 $mm^3$ on day 22. By day 24, the mean tumor volume of the PBS control group had exceeded 1000 $mm^3$. Interestingly, sc H929 tumors did not grow in the mice treated with 0.5 μg and 1 μg BCMB72 (FIG. 21). Thus, BCMB72 inhibited the tumorigenesis of H929 human MM xenografts in all animals treated with 0.5 and 1 μg/animal.

Example 22: Soluble BCMA Quantitation in Mouse Serum from H929 (Human Multiple Myeloma Cells) Xenografts in PBMC-Humanized NSG Mice Treated with BCMB72

This study was designed to quantify soluble BMCA levels in serum form H929 xenograft mice and to correlate the soluble BCMA levels to tumor burden in these animals.

Briefly, serum from xenograft study samples were analyzed by BCMA enzyme-linked immunosorbent assay (ELISA), obtained from R&D Systems. Serum was thawed and diluted 1:50 in reagent diluent and incubated overnight at 4° C. The BCMA ELISA was carried out according to the manufacturer's protocol. The ELISA plates were analyzed using MD SpectraMax plate reader M5 (Molecular Devices, Sunnyvale Calif.) set to 450 nm. Each well in the ELISA corresponds to serum from one mouse in the original xenograft study.

Figure 22:
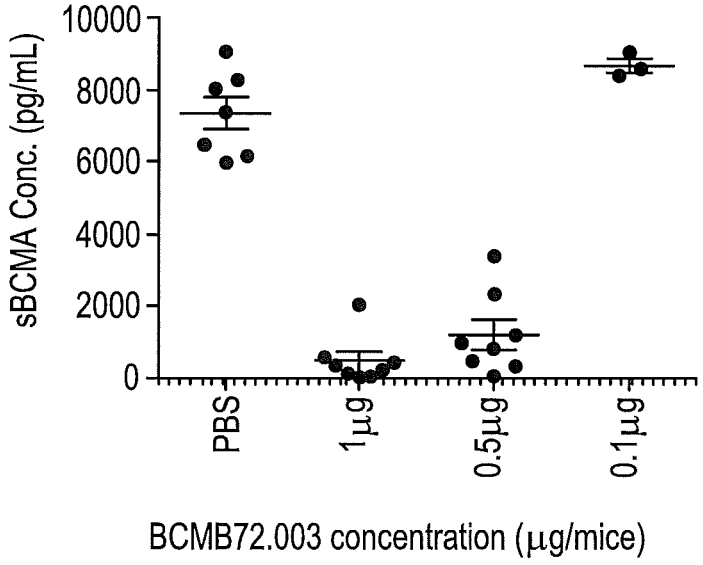
FIG. 22. Serum soluble BCMA levels in H929 xenograft mice. Serum soluble BCMA concentration was detected using the human BCMA ELISA kit (R&D Systems). Soluble BCMA levels were significantly lower in the mice treatment with 1 μg and 0.5 μg/mice of BCMB72 compared to PBS control which correlates nicely with the tumor burden in these animals. Lower doses of BCMB72 (0.1 μg/mice) had no effect on the sBCMA levels or the tumor size.

There was significant reduction of soluble BCMA concentration in mouse serum of mice treated with 1 μg and 0.5 μg of BCMB72 when compared with PBS alone or BCMB72 at 0.1 μg/mice (FIG. 22). These data support the xenograft study, where mice treated with 1 μg and 0.5 μg of BCMB72 had no or minimal tumor growth. These data suggest that soluble BCMA in serum samples could be insightful as a potential biomarker to assess indication of multiple myeloma; surveying soluble BCMA may help in monitoring the disease burden.

BRIEF DESCRIPTION OF THE SEQUENCE LISTING

| SEQ ID NO: | Type | Species | Description | Sequence |
|---|---|---|---|---|
| 1 | PRT | human | BCMA | MLQMAGQCSQNEYFDSLLHACIPCQLR CSSNTPPLTCQRYCNASVTNSVKGTNAI LWTCLGLSLIISLAVFVLMFLLRKINSEP LKDEFKNTGSGLLGMANIDLEKSRTGD EIILPRGLEYTVEECTCEDCIKSKPKVDS DHCFPLPAMEEGATILVTTKTNDYCKSL PAALSATEIEKSISAR |
| 2 | PRT | mouse | BCMA | MAQQCFHSEYFDSLLHACKPCHLRCSN PPATCQPYCDPSVTSSVKGTYTVLWIFL GLTLVLSLALFTISFLLRKMNPEALKDE PQSPGQLDGSAQLDKADTELTRIRAGD DRIFPRSLEYTVEECTCEDCVKSKPKGD SDHFFPLPAMEEGATILVTTKTGDYGKS SVPTALQSVMGMEKPTHTR |
| 3 | PRT | cyno | BCMA | MLQMARQCSQNEYFDSLLHDCKPCQL RCSSTPPLTCQRYCNASMTNSVKGMNA ILWTCLGLSLIISLAVFVLTFLLRKMSSE PLKDEFKNTGSGLLGMANIDLEKGRTG DEIVLPRGLEYTVEECTCEDCIKNKPKV DSDHCFPLPAMEEGATILVTTKTNDYC NSLSAALSVTEIEKSISAR |
| 4 | PRT | human | BCMB69, BCMB117, BCMB118, BCMB119, BCMB120, BCMB125, BCMB126, BCMB127, BCMB128, AND BCMB129-HCDR1 | SGSYFWG |
| 5 | PRT | human | BCMB69, BCMB117, BCMB118, BCMB119, BCMB120, BCMB123, BCMB124, BCMB125, BCMB126, BCMB127, BCMB128, BCMB176, BCMB179, BCMB180, BCMB181, and BCMB182-HCDR2 | SIYYSGITYYNPSLKS |
| 6 | PRT | human | BCMB69, BCMB117, BCMB121, BCMB122, BCMB123, BCMB124, and BCMB129-HCDR3 | HDGAVAGLFDY |
| 7 | PRT | human | BCMB121, BCMB122, and BCMB123 HCDR1 | SSSYYWG |

-continued

| SEQ ID NO: | Type | Species | Description | Sequence |
|---|---|---|---|---|
| 8 | PRT | human | BCMB121, BCMB122, BCMB129, BCMB130, BCMB131, and BCMB177-HCDR2 | SIYYSGSTYYNPSLKS |
| 9 | PRT | human | BCMB118-HCDR3 | HDAATAGLFDY |
| 10 | PRT | human | BCMB124, BCMB130, and BCMB131-HCDR1 | SGSYYWG |
| 11 | PRT | human | BCMB178, BCMB186, BCMB187, and BCMB188-HCDR2 | SIYYSGWTYYNPSLKS |
| 12 | PRT | human | BCMB119-HCDR3 | HEGATAGLFDY |
| 13 | PRT | human | BCMB176, BCMB177, BCMB178, BCMB179, BCMB180, BCMB181, BCMB182, BCMB183, BCMB184, BCMB185, BCMB186, BCMB187, and BCMB188-HCDR1 | SSSYFWG |
| 14 | PRT | human | BCMB183, BCMB184, and BCMB185-HCDR2 | SIYYSGRTYYNPSLKS |
| 15 | PRT | human | BCMB120-HCDR3 | HSGATAGLFDY |
| 16 | PRT | human | BCMB125 and BCMB131-HCDR3 | HEGAVAGLFDY |
| 17 | PRT | human | BCMB126-HCDR3 | HSGAVAGLFDY |
| 18 | PRT | human | BCMB127 and BCMB130-HCDR3 | HDAAVAGLFDY |
| 19 | PRT | human | BCMB128, BCMB176, BCMB177, and BCMB178-HCDR3 | HDGATAGLFDY |
| 20 | PRT | human | BCMB179, BCMB183, | HQGATAGLFDY |

-continued

| SEQ ID NO: | Type | Species | Description | Sequence |
|---|---|---|---|---|
| | | | and BCMB186-HCDR3 | |
| 21 | PRT | human | BCMB180, BCMB184, and BCMB187-HCDR3 | HHGATAGLFDY |
| 22 | PRT | human | BCMB181-HCDR3 | HWGATAGLFDY |
| 23 | PRT | human | BCMB182, BCMB185, and BCMB188-HCDR3 | HYGATAGLFDY |
| 24 | PRT | human | BCMB69, BCMB117, BCMB118, BCMB119, BCMB120, BCMB121, BCMB122, BCMB123, BCMB124, BCMB125, BCMB126, BCMB127, BCMB128, BCMB129, BCMB130, BCMB131, BCMB176, BCMB177, BCMB178, BCMB179, BCMB180, BCMB181, BCMB182, BCMB183, BCMB184 BCMB185, BCMB186, BCMB187, and BCMB188-LCDR1 | GGNNIGSKSVH |
| 25 | PRT | human | BCMB69, BCMB117, BCMB118, BCMB119, BCMB120, BCMB121, BCMB122, BCMB123, BCMB124, BCMB125, BCMB126, BCMB127, BCMB128, BCMB129, BCMB130, BCMB131, BCMB176, BCMB177, BCMB178, BCMB179, BCMB180, BCMB181, BCMB182, BCMB183, | DDSDRPS |

-continued

| SEQ ID NO: | Type | Species | Description | Sequence |
|---|---|---|---|---|
| | | | BCMB184, BCMB185, BCMB186, BCMB187, and BCMB188-LCDR2 | |
| 26 | PRT | human | BCMB69, BCMB117, BCMB118, BCMB119, BCMB120, BCMB121, BCMB122, BCMB123, BCMB124, BCMB125, BCMB126, BCMB127, BCMB128, BCMB129, BCMB130, BCMB131, BCMB176, BCMB177, BCMB178, BCMB179, BCMB180, BCMB181, BCMB182, BCMB183, BCMB184, BCMB185, BCMB186, BCMB187, and BCMB188-LCDR3 | QVWDSSSDHVV |
| 27 | PRT | human | BCMB69-VH | QLQLQESGPGLVKPSETLSLTCTVSGGSI SSGSYFWGWIRQPPGKGLEWIGSIYYSG ITYYNPSLKSRVTISVDTSKNQFSLKLSS VTAADTAVYYCARHDGAVAGLFDYW GQGTLVTVSSA |
| 28 | PRT | human | BCMB69, BCMB118, BCMB119, BCMB120, BCMB122, BCMB123, BCMB124, BCMB125, BCMB126, BCMB127, BCMB128, BCMB129, BCMB130, BCMB131, BCMB177, BCMB178, BCMB179, BCMB180, BCMB181, BCMB182, BCMB183, BCMB184, BCMB185, BCMB186, BCMB187, and BCMB188-VL | SYVLTQPPSVSVAPGQTARITCGGNNIG SKSVHWYQQPPGQAPVVVVYDDSDRP SGIPERFSGSNSGNATATLTISRVEAGDEA VYYCQVWDSSSDHVVFGGGTKLTVL |

-continued

| SEQ ID NO: | Type | Species | Description | Sequence |
|---|---|---|---|---|
| 29 | PRT | human | BCMB118-VH | QLQLQESGPGLVKPSETLSLTCTVSGGSI SSGSYYWGWIRQPPGKGLEWIGSIYYS GITYYNPSLKSRVTISVDTSKNQFSLKLS SVTAADTAVYYCARHDAATAGLFDYW GQGTLVTVSSA |
| 30 | PRT | human | BCMB121-VL | SYVLTQPPSVSVAPGQTARITCGGNNIG SKSVHWYQQKPGQAPVLVVYDDSDRP SGIPERFSGSNSGNTATLTISRVEAGDEA DYYCQVWDSSSDHVVFGGGTKLTVL |
| 31 | PRT | human | BCMB119-VH | QLQLQESGPGLVKPSETLSLTCTVSGGSI SSGSYYWGWIRQPPGKGLEWIGSIYYS GITYYNPSLKSRVTISVDTSKNQFSLKLS SVTAADTAVYYCARHEGATAGLFDYW GQGTLVTVSSA |
| 32 | PRT | human | BCMB120-VH | QLQLQESGPGLVKPSETLSLTCTVSGGS ISSSSYYWGWIRQPPGKGLEWGSIYYSG GTYYNPSLKSRVTISVDTSKNQSLKLSS VTAADTAVYYCARHDGAVAGLFDYWGQG TLVTVSSA |
| 33 | PRT | human | BCMB121 and BCMB122-VH | QLQLQESGPGLVKPSETLSLTCTVSGGSI SSSSYYWGWIRQPPGKGLEWIGSIYYS GSTYYNPSLKSRVTISVDTSKNQFSLKLS SVTAADTAVYYCARHDGAVAGLFDYW GQGTLVTVSSA |
| 34 | PRT | human | BCMB123-VH | QLQLQESGPGLVKPSETLSLTCTVSGGSI SSSSYYWGWIRQPPGKGLEWIGSIYYS GSTYYNPSLKSRVTISVDTSKNQFSLKLS SVTAADTAVYYCARHDGAVAGLFDYW GQGTLVTVSSA |
| 35 | PRT | human | BCMB124-VH | QLQLQESGPGLVKPSETLSLTCTVSGGSI SSSSYFWGWIRQPPGKGLEWIGSIYYS GITYYNPSLKSRVTISVDTSKNQFSLKLS SVTAADTAVYYCARHDGAVAGLFDYW GQGTLVTVSSA |
| 36 | PRT | human | BCMB125-VH | QLQLQESGPGLVKPSETLSLTCTVSGGSI SSSSYFWGWIRQPPGKGLEWIGSIYYS GITYYNPSLKSRVTISVDTSKNQFSLKLS SVTAADTAVYYCAREDGAVAGLFDYW GQGTLVTVSSA |
| 37 | PRT | human | BCMB126-VH | QLQLQESGPGLVKPSETLSLTCTVSGGSI SSGSYFWGWIRQPPGKGLEWIGSIYYS GSIYYNPSLKSRVTISVDTSKNQFSLKLS SVTAADTAVYYCARHSGAVAGLFDYW GQGTLVTVSSA |
| 38 | PRT | human | BCMB127-VH | QLQLQESGPGLVKPSETLSLTCTVSGGSI SSGSYFWGWIRQPPGKGLEWIGSIYYS GSIYYNPSLKSRVTISVDTSKNQFSLKLS SVTAADTAVYYCARHDAAVAGLFDYW GQGTLVTVSSA |
| 39 | PRT | human | BCMB128-VH | QLQLQESGPGLVKPSETLSLTCTVSGGSI SSGSYFWGWIRQPPGKGLEWIGSIYYS GSIYYNPSLKSRVTISVDTSKNQFSLKLS SVTAADTAVYYCARHAGATAGLFDYW GQGTLVTVSSA |
| 40 | PRT | human | BCMB129-VH | QLQLQESGPGLVKPSETLSLTCTVSGGSI SSGSYFWGWIRQPPGKGLEWIGSIYYS GSTYYNPSLKSRVTISVDTSKNQFSLKLS SVTAADTAVYYCARHDGAVAGLFDYW GQGTLVTVSSA |
| 41 | PRT | human | BCMB130-VH | QLQLQESGPGLVKPSETLSLTCTVSGGSI SSGSYYWGWIRQPPGKGLEWIGSIYYS |

-continued

| SEQ ID NO: | Type | Species | Description | Sequence |
|---|---|---|---|---|
| | | | | GSTYYNPSLKSRVTISVDTSKNQFSLKLS SVTAADTAVYYCARHDGAVAGLFDYW GQGTLVTVSSA |
| 42 | PRT | human | BCMB131-VH | QLQLQESGPGLVKPSETLSLTCTVSGGSI SSGSYYWGWIRQPPGKGLEWIGSIYYS GSTYYNPSLKSRVTISVDTSKNQFSLKLS SVTAADTAVYYCARHEGAVAGLFDYW GQGTLVTVSSA |
| 43 | PRT | human | BCMB177-VH | QLQLQESGPGLVKPSETLSLTCTVSGGSI SSSSYFWGWIRQPPGKGLEWIGSIYYS GRTYYNPSLKSRVTISVDTSKNQFSLKLS SVTAADTAVYYCARHDGATAGLFDYW GQGTLVTVSSA |
| 44 | PRT | human | BCMB178-VH | QLQLQESGPGLVKPSETLSLTCTVSGGSI SSSSYFWGWIRQPPGKGLEWIGSIYYS GWTYYNPSLKSRVTISVDTSKNQFSLKLS SVTAADTAVYYCARHDGAVAGLFDYW GQGTLVTVSSA |
| 45 | PRT | human | BCMB179-VH | QLQLQESGPGLVKPSETLSLTCTVSGGSI SSSSYFWGWIRQPPGKGLEWIGSIYYS GITYYNPSLKSRVTISVDTSKNQFSLKLS SVTAADTAVYYCARHQGATAGLFDYW GQGTLVTVSSA |
| 46 | PRT | human | BCMB180-VH | QLQLQESGPGLVKPSETLSLTCTVSGGSI SSSSYFWGWIRQPPGKGLEWIGSIYYS GITYYNPSLKSRVTISVDTSKNQFSLKLS SVTAADTAVYYCARHHGATAGLFDYW GQGTLVTVSSA |
| 47 | PRT | human | BCMB181-VH | QLQLQESGPGLVKPSETLSLTCTVSGGSI SSSSYFWGWIRQPPGKGLEWIGSIYYS GITYYNPSLKSRVTISVDTSKNQFSLKLS SVTAADTAVYYCARWDGATAGLFDYW GQGTLVTVSSA |
| 48 | PRT | human | BCMB182-VH | QLQLQESGPGLVKPSETLSLTCTVSGGSI SSSSYFWGWIRQPPGKGLEWIGSIYYS GITYYNPSLKSRVTISVDTSKNQFSLKLS SVTAADTAVYYCARYDGATAGLFDYW GQGTLVTVSSA |
| 49 | PRT | human | BCMB183-VH | QLQLQESGPGLVKPSETLSLTCTVSGGSI SSSSYFWGWIRQPPGKGLEWIGSIYYS GRTYYNPSLKSRVTISVDTSKNQFSLKLS SVTAADTAVYYCARHQGATAGLFDYW GQGTLVTVSSA |
| 50 | PRT | human | BCMB184-VH | QLQLQESGPGLVKPSETLSLTCTVSGGSI SSSSYFWGWIRQPPGKGLEWIGSIYYS GRTYYNPSLKSRVTISVDTSKNQFSLKLS SVTAADTAVYYCARHHGATAGLFDYW GQGTLVTVSSA |
| 51 | PRT | human | BCMB185-VH | QLQLQESGPGLVKPSETLSLTCTVSGGSI SSSSYFWGWIRQPPGKGLEWIGSIYYS GRTYYNPSLKSRVTISVDTSKNQFSLKLS SVTAADTAVYYCARHYGATAGLFDYW GQGTLVTVSSA |
| 52 | PRT | human | BCMB186-VH | QLQLQESGPGLVKPSETLSLTCTVSGGSI SSSSYFWGWIRQPPGKGLEWIGSIYYS GWTYYNPSLKSRVTISVDTSKNQFSLKLS SVTAADTAVYYCARHQGATAGLFDYW GQGTLVTVSSA |
| 53 | PRT | human | BCMB187-VH | QLQLQESGPGLVKPSETLSLTCTVSGGSI SSSSYFWGWIRQPPGKGLEWIGSIYYS GWTYYNPSLKSRVTISVDTSKNQFSLKLS SVTAADTAVYYCARHHGATAGLFDYW GQGTLVTVSSA |

-continued

| SEQ ID NO: | Type | Species | Description | Sequence |
|---|---|---|---|---|
| 54 | PRT | human | BCMB188-VH | QLQLQESGPGLVKPSETLSLTCTVSGGSI SSSSYFWGWIRQPPGKGLEWIGSIYYS GWTYYNPSLKSRVTISVDTSKNQFSLKLS SVTAADTAVYYCARHYGATAGLFDYW GQGTLVTVSSA |
| 55 | PRT | human | CD3B219-Heavy chain | EVQLVESGGGLVQPGGSLRLSCAASGF TFNTYAMNWVRQAPGKGLEWVARIRS KYNNYATYYAASVKGRFTISRDDSKNS LYLQMSLKTEDTAVYYCARHGNFGN SYVSWFAYWGQGTLVTVSSASTKGPSV FPLAPCSRSTSESTAALGCLVKDYFPEP VTVSWNSGALTSGVHTFPAVLQSSGLY SLSSVVTVPSSSLGTKTYTCNVDHKPSN TKVDKRVESKYGPPCPPCPAPEAAGGP SVFLFPPKPKDTLMISRTPEVTCVVVDV SQEDPEVQFNWYVDGVEVHNAKTKPR EEQFNSTYRVVSVLTVLHQDWLNGKE YKCKVSNKGLPSSIEKTISKAKGQPREP QVYTLPPSQEEMTKNQVSLTCLVKGFY PSDIAVEWESNGQPENNYKTTPPVLDSD GSFLLYSKLTVDKSRWQEGNVFSCSVM HEALHNHYTQKSLSLSLGK |
| 56 | PRT | human | CD3B219-Light chain | QTVVTQEPSLTVSPGGTVTLTCRSSTGA VTTSNYANWVQQKPGQAPRGLIGGTN KRAPGTPARFSGSLLGGKAALTLSGVQ PEDEAEYYCALWYSNLWVFGGGTKLT VLGQPKAAPSVTLFPPSSEELQANKATL VCLISDFYPGAVTVAWKADSSPVKAGV ETTTPSKQSNNKYAASSYLSLTPEQWKS HRSYSCQVTHEGSTVEKTVAPTECS |
| 57 | PRT | human | BCBM117-VH | QLQLQESGPGLVKPSETLSLTCTVSGGSI SSGSYFWGWIRQPPGKGLEWIGSIYYSG ITYYNPSLKSRVTISVDTSKNQFSLKLSS VTAADTAVYYCARHDGAVAGLFDYW GQGTLVTVSSA |
| 58 | PRT | human | BCBM176-VH | QLQLQESGPGLVKPSETLSLTCTVSGGSI SSSSYFWGWIRQPPGKGLEWIGSIYYSG ITYYNPSLKSRVTISVDTSKNQFSLKLSS VTAADTAVYYCARH DGATAGLFDYWGQGTLVTVSSA |
| 59 | PRT | human | CD3B219-VH | TYAMN |
| 60 | PRT | human | CD3B219-VH | RIRSKYNNYATYYAASVKG |
| 61 | PRT | human | CD3B219-VH | HGNFGNSYVSWFAY |
| 62 | PRT | human | CD3B219-VL | RSSTGAVTTSNYAN |
| 63 | PRT | human | CD3B219-VL | GTNKRAP |
| 64 | PRT | human | CD3B219-VL | ALWYSNLWV |
| 65 | PRT | human | BCMB69-Heavy chain | QLQLQESGPGLVKPSETLSLTCTVSGGSI SSGSYFWGWIRQPPGKGLEWIGSIYYSG ITYYNPSLKSRVTISVDTSKNQFSLKLSS VTAADTAVYYCARHDGAVAGLFDYW GQGTLVTVSSASTKGPSVFPLAPCSRST SESTAALGCLVKDYFPEPVTVSWNSGA LTSGVHTFPAVLQSSGLYSLSSVVTVPS SSLGTKTYTCNVDHKPSNTKVDKRVES KYGPPCPPCPAPEAAGGPSVFLFPPKPK DTLMISRTPEVTCVVVDVSQEDPEVQF NWYVDGVEVHNAKTKPREEQFNSTYR VVSVLTVLHQDWLNGKEYKCKVSNKG |

-continued

| SEQ ID NO: | Type | Species | Description | Sequence |
|---|---|---|---|---|
| | | | | LPSSIEKTISKAKGQPREPQVYTLPPSQE<br>EMTKNQVSLTCLVKGFYPSDIAVEWES<br>NGQPENNYKTTPPVLDSDGSFFLYSRLT<br>VDKSRWQEGNVFSCSVMHEALHNHYT<br>QKSLSLSLGK |
| 66 | PRT | human | BCMB123,<br>BCMB128,<br>BCMB129,<br>BCMB177,<br>BCMB178,<br>BCMB179,<br>BCMB180,<br>BCMB181,<br>BCMB182,<br>BCMB183,<br>BCMB184,<br>BCMB185,<br>BCMB186,<br>BCMB187,<br>and<br>BCMB188-<br>Light<br>chain | SYVLTQPPSVSVAPGQTARITCGGNNIG<br>SKSVHWYQQPPGQAPVVVVYDDSDRP<br>SGIPERFSGSNSGNTATLTISRVEAGDEA<br>VYYCQVWDSSSDHVVFGGGTKLTVLG<br>QPKAAPSVTLFPPSSEELQANKATLVCL<br>ISDFYPGAVTVAWKADSSPVKAGVETT<br>TPSKQSNNKYAASSYLSLTPEQWKSHR<br>SYSCQVTHEGSTVEKTVAPTECS |
| 67 | PRT | human | BCMB117-<br>Heavy<br>chain | QLQLQESGPGLVKPSETLSLTCTVSGGSI<br>SSGSYFWGWIRQPPGKGLEWIGSIYYSG<br>ITYYNPSLKSRVTISVDTSKNQFSLKLSS<br>VTAADTAVYYCARHDGAVAGLFDYW<br>GQGTLVTVSSASTKGPSVFPLAPCSRST<br>SESTAALGCLVKDYFPEPVTVSWNSGA<br>LTSGVHTFPAVLQSSGLYSLSSVVTVPS<br>SSLGTKTYTCNVDHKPSNTKVDKRVES<br>KYGPPCPPCPAPEAAGGPSVFLFPPKPK<br>DTLMISRTPEVTCVVVDVSQEDPEVQF<br>NWYVDGVEVHNAKTKPREEQFNSTYR<br>VVSVLTVLHQDWLNGKEYKCKVSNKG<br>LPSSIEKTISKAKGQPREPQVYTLPPSQE<br>EMTKNQVSLTCLVKGFYPSDIAVEWES<br>NGQPENNYKTTPPVLDSDGSFFLYSRLT<br>VDKSRWQEGNVFSCSVMHEALHNHYT<br>QKSLSLSLGK |
| 68 | PRT | human | BCMB123-<br>Heavy<br>chain | QLQLQESGPGLVKPSETLSLTCTVSGGSI<br>SSSSYFWGWIRQPPGKGLEWIGSIYYSG<br>ITYYNPSLKSRVTISVDTSKNQFSLKLSS<br>VTAADTAVYYCARHDGAVAGLFDYW<br>GQGTLVTVSSASTKGPSVFPLAPCSRST<br>SESTAALGCLVKDYFPEPVTVSWNSGA<br>LTSGVHTFPAVLQSSGLYSLSSVVTVPS<br>SSLGTKTYTCNVDHKPSNTKVDKRVES<br>KYGPPCPPCPAPEAAGGPSVFLFPPKPK<br>DTLMISRTPEVTCVVVDVSQEDPEVQF<br>NWYVDGVEVHNAKTKPREEQFNSTYR<br>VVSVLTVLHQDWLNGKEYKCKVSNKG<br>LPSSIEKTISKAKGQPREPQVYTLPPSQE<br>EMTKNQVSLTCLVKGFYPSDIAVEWES<br>NGQPENNYKTTPPVLDSDGSFFLYSRLT<br>VDKSRWQEGNVFSCSVMHEALHNHYT<br>QKSLSLSLGK |
| 69 | PRT | human | BCMB128-<br>Heavy<br>chain | QLQLQESGPGLVKPSETLSLTCTVSGGSI<br>SSGSYFWGWIRQPPGKGLEWIGSIYYSG<br>ITYYNPSLKSRVTISVDTSKNQFSLKLSS<br>VTAADTAVYYCARHDGATAGLFDYW<br>GQGTLVTVSSASTKGPSVFPLAPCSRST<br>SESTAALGCLVKDYFPEPVTVSWNSGA<br>LTSGVHTFPAVLQSSGLYSLSSVVTVPS<br>SSLGTKTYTCNVDHKPSNTKVDKRVES<br>KYGPPCPPCPAPEAAGGPSVFLFPPKPK<br>DTLMISRTPEVTCVVVDVSQEDPEVQF<br>NWYVDGVEVHNAKTKPREEQFNSTYR<br>VVSVLTVLHQDWLNGKEYKCKVSNKG<br>LPSSIEKTISKAKGQPREPQVYTLPPSQE<br>EMTKNQVSLTCLVKGFYPSDIAVEWES |

-continued

| SEQ ID NO: | Type | Species | Description | Sequence |
|---|---|---|---|---|
| | | | | NGQPENNYKTTPPVLDSDGSFFLYSRLT<br>VDKSRWQEGNVFSCSVMHEALHNHYT<br>QKSLSLSLGK |
| 70 | PRT | human | BCMB129-<br>Heavy<br>chain | QLQLQESGPGLVKPSETLSLTCTVSGGSI<br>SSGSYFWGWIRQPPGKGLEWIGSIYYSG<br>STYYNPSLKSRVTISVDTSKNQFSLKLSS<br>VTAADTAVYYCARHDGAVAGLFDYW<br>GQGTLVTVSSASTKGPSVFPLAPCSRST<br>SESTAALGCLVKDYFPEPVTVSWNSGA<br>LTSGVHTFPAVLQSSGLYSLSSVVTVPS<br>SSLGTKTYTCNVDHKPSNTKVDKRVES<br>KYGPPCPPCPAPEAAGGPSVFLFPPKPK<br>DTLMISRTPEVTCVVVDVSQEDPEVQF<br>NWYVDGVEVHNAKTKPREEQFNSTYR<br>VVSVLTVLHQDWLNGKEYKCKVSNKG<br>LPSSIEKTISKAKGQPREPQVYTLPPSQE<br>EMTKNQVSLTCLVKGFYPSDIAVEWES<br>NGQPENNYKTTPPVLDSDGSFFLYSRLT<br>VDKSRWQEGNVFSCSVMHEALHNHYT<br>QKSLSLSLGK |
| 71 | PRT | human | BCMB176-<br>Heavy<br>chain | QLQLQESGPGLVKPSETLSLTCTVSGGSI<br>SSSSYFWGWIRQPPGKGLEWIGSIYYSG<br>ITYYNPSLKSRVTISVDTSKNQFSLKLSS<br>VTAADTAVYYCARHDGATAGLFDYW<br>GQGTLVTVSSASTKGPSVFPLAPCSRST<br>SESTAALGCLVKDYFPEPVTVSWNSGA<br>LTSGVHTFPAVLQSSGLYSLSSVVTVPS<br>SSLGTKTYTCNVDHKPSNTKVDKRVES<br>KYGPPCPPCPAPEAAGGPSVFLFPPKPK<br>DTLMISRTPEVTCVVVDVSQEDPEVQF<br>NWYVDGVEVHNAKTKPREEQFNSTYR<br>VVSVLTVLHQDWLNGKEYKCKVSNKG<br>LPSSIEKTISKAKGQPREPQVYTLPPSQE<br>EMTKNQVSLTCLVKGFYPSDIAVEWES<br>NGQPENNYKTTPPVLDSDGSFFLYSRLT<br>VDKSRWQEGNVFSCSVMHEALHNHYT<br>QKSLSLSLGK |
| 72 | PRT | human | BCMB177-<br>Heavy<br>chain | QLQLQESGPGLVKPSETLSLTCTVSGGSI<br>SSSSYFWGWIRQPPGKGLEWIGSIYYSG<br>RTYYNPSLKSRVTISVDTSKNQFSLKLSS<br>VTAADTAVYYCARHDGATAGLFDYW<br>GQGTLVTVSSASTKGPSVFPLAPCSRST<br>SESTAALGCLVKDYFPEPVTVSWNSGA<br>LTSGVHTFPAVLQSSGLYSLSSVVTVPS<br>SSLGTKTYTCNVDHKPSNTKVDKRVES<br>KYGPPCPPCPAPEAAGGPSVFLFPPKPK<br>DTLMISRTPEVTCVVVDVSQEDPEVQF<br>NWYVDGVEVHNAKTKPREEQFNSTYR<br>VVSVLTVLHQDWLNGKEYKCKVSNKG<br>LPSSIEKTISKAKGQPREPQVYTLPPSQE<br>EMTKNQVSLTCLVKGFYPSDIAVEWES<br>NGQPENNYKTTPPVLDSDGSFFLYSRLT<br>VDKSRWQEGNVFSCSVMHEALHNHYT<br>QKSLSLSLGK |
| 73 | PRT | arti-<br>ficial | IgG4PAA | ASTKGPSVFPLAPCSRSTSESTAALGCL<br>VKDYFPEPVTVSWNSGALTSGVHTFPA<br>VLQSSGLYSLSSVVTVPSSSLGTKTYTC<br>NVDHKPSNTKVDKRVESKYGPPCPPCP<br>APEAAGGPSVFLFPPKPKDTLMISRTPE<br>VTCVVVDVSQEDPEVQFNWYVDGVEV<br>HNAKTKPREEQFNSTYRVVSVLTVLHQ<br>DWLNGKEYKCKVSNKGLPSSIEKTISKA<br>KGQPREPQVYTLPPSQEEMTKNQVSLT<br>CLVKGFYPSDIAVEWESNGQPENNYKT<br>TPPVLDSDGSFFLYSRLTVDKSRWQEG<br>NVFSCSVMHEALHNHYTQKSLSLSLGK |
| 74 | PRT | human | IgG1 | ASTKGPSVFPLAPSSKSTSGGTAALGCL<br>VKDYFPEPVTVSWNSGALTSGVHTFPA<br>VLQSSGLYSLSSVVTVPSSSLGTQTYIC<br>NVNHKPSNTKVDKKVEPKSCDKTHTCP |

-continued

| SEQ ID NO: | Type | Species | Description | Sequence |
|---|---|---|---|---|
| | | | | PCPAPELLGGPSVFLFPPKPKDTLMISR TPEVTCVVVDVSHEDPEVKFNWYVDGV EVHNAKTKPREEQYNSTYRVVSVLTVL HQDWLNGKEYKCKVSNKALPAPIEKTI SKAKGQPREPQVYTLPPSREEMTKNQV SLTCLVKGFYPSDIAVEWESNGQPENN YKTTPPVLDSDGSFFLYSKLTVDKSRW QQGNVFSCSVMHEALHNHYTQKSLSLS PGK |
| 75 | PRT | human | Fab | QLQLQESGPGLVKPSETLSLTCTVSGGSI SSGSYFWGWIRQPPGKGLEWIGSIYYSG ITYYNPSLKSRVTISVDTSKNQFSLKLSS VTAADTAVYYCARHDGAVAGLFDYW GQGTLVTVSSASTKGPSVFPLAPSSKST SGGTAALGCLVKDYFPEPVTVSWNSGA LTSGVHTFPAVLQSSGLYSLSSVVTVPS SSLGTQTYICNVNHKPSNTKVDKKVEP KSCHHHHHH |
| 76 | PRT | human | BCMB69, BCMB118, BCMB119, BCMB120, BCMB122, BCMB124, BCMB125, BCMB126, BCMB127, BCMB130, BCMB131-Light chain | SYVLTQPPSVSVAPGQTARITCGGNNIG SKSVHWYQQPPGQAPVVVVYDDSDRP SGIPERFSGSNSGNATATLTISRVEAGDEA VYYCQVWDSSSDHVVFGGGTKLTVLG QPKAAPSVTLFPPSSEELQANKATLVCL ISDFYPGAVTVAWKGDSSPVKAGVETT TPSKQSNNKYAASSYLSLTPEQWKSHR SYSCQVTHEGSTVEKTVAPTECS |

SEQUENCE LISTING

<160> NUMBER OF SEQ ID NOS: 77

<210> SEQ ID NO 1
<211> LENGTH: 184
<212> TYPE: PRT
<213> ORGANISM: Homo sapiens

<400> SEQUENCE: 1

Met Leu Gln Met Ala Gly Gln Cys Ser Gln Asn Glu Tyr Phe Asp Ser
1 5 10 15

Leu Leu His Ala Cys Ile Pro Cys Gln Leu Arg Cys Ser Ser Asn Thr
20 25 30

Pro Pro Leu Thr Cys Gln Arg Tyr Cys Asn Ala Ser Val Thr Asn Ser
35 40 45

Val Lys Gly Thr Asn Ala Ile Leu Trp Thr Cys Leu Gly Leu Ser Leu
50 55 60

Ile Ile Ser Leu Ala Val Phe Val Leu Met Phe Leu Leu Arg Lys Ile
65 70 75 80

Asn Ser Glu Pro Leu Lys Asp Glu Phe Lys Asn Thr Gly Ser Gly Leu
85 90 95

Leu Gly Met Ala Asn Ile Asp Leu Glu Lys Ser Arg Thr Gly Asp Glu
100 105 110

Ile Ile Leu Pro Arg Gly Leu Glu Tyr Thr Val Glu Glu Cys Thr Cys
115 120 125

Glu Asp Cys Ile Lys Ser Lys Pro Lys Val Asp Ser Asp His Cys Phe
130 135 140

```
Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180


<210> SEQ ID NO 2
<211> LENGTH: 185
<212> TYPE: PRT
<213> ORGANISM: Mus sp.

<400> SEQUENCE: 2

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
            20                  25                  30

Gln Pro Tyr Cys Asp Pro Ser Val Thr Ser Ser Val Lys Gly Thr Tyr
        35                  40                  45

Thr Val Leu Trp Ile Phe Leu Gly Leu Thr Leu Val Leu Ser Leu Ala
    50                  55                  60

Leu Phe Thr Ile Ser Phe Leu Leu Arg Lys Met Asn Pro Glu Ala Leu
65                  70                  75                  80

Lys Asp Glu Pro Gln Ser Pro Gly Gln Leu Asp Gly Ser Ala Gln Leu
                85                  90                  95

Asp Lys Ala Asp Thr Glu Leu Thr Arg Ile Arg Ala Gly Asp Asp Arg
            100                 105                 110

Ile Phe Pro Arg Ser Leu Glu Tyr Thr Val Glu Glu Cys Thr Cys Glu
        115                 120                 125

Asp Cys Val Lys Ser Lys Pro Lys Gly Asp Ser Asp His Phe Phe Pro
    130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
            180                 185


<210> SEQ ID NO 3
<211> LENGTH: 183
<212> TYPE: PRT
<213> ORGANISM: Macaca fascicularis

<400> SEQUENCE: 3

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
            20                  25                  30

Pro Leu Thr Cys Gln Arg Tyr Cys Asn Ala Ser Met Thr Asn Ser Val
        35                  40                  45

Lys Gly Met Asn Ala Ile Leu Trp Thr Cys Leu Gly Leu Ser Leu Ile
    50                  55                  60

Ile Ser Leu Ala Val Phe Val Leu Thr Phe Leu Leu Arg Lys Met Ser
65                  70                  75                  80

Ser Glu Pro Leu Lys Asp Glu Phe Lys Asn Thr Gly Ser Gly Leu Leu
                85                  90                  95
```

```
Gly Met Ala Asn Ile Asp Leu Glu Lys Gly Arg Thr Gly Asp Glu Ile
            100                 105                 110

Val Leu Pro Arg Gly Leu Glu Tyr Thr Val Glu Glu Cys Thr Cys Glu
        115                 120                 125

Asp Cys Ile Lys Asn Lys Pro Lys Val Asp Ser Asp His Cys Phe Pro
    130                 135                 140

Leu Pro Ala Met Glu Glu Gly Ala Thr Ile Leu Val Thr Thr Lys Thr
145                 150                 155                 160

Asn Asp Tyr Cys Asn Ser Leu Ser Ala Ala Leu Ser Val Thr Glu Ile
                165                 170                 175

Glu Lys Ser Ile Ser Ala Arg
            180


<210> SEQ ID NO 4
<211> LENGTH: 7
<212> TYPE: PRT
<213> ORGANISM: Homo sapiens

<400> SEQUENCE: 4

Ser Gly Ser Tyr Phe Trp Gly
1               5


<210> SEQ ID NO 5
<211> LENGTH: 16
<212> TYPE: PRT
<213> ORGANISM: Homo sapiens

<400> SEQUENCE: 5

Ser Ile Tyr Tyr Ser Gly Ile Thr Tyr Tyr Asn Pro Ser Leu Lys Ser
1               5                   10                  15


<210> SEQ ID NO 6
<211> LENGTH: 11
<212> TYPE: PRT
<213> ORGANISM: Homo sapiens

<400> SEQUENCE: 6

His Asp Gly Ala Val Ala Gly Leu Phe Asp Tyr
1               5                   10


<210> SEQ ID NO 7
<211> LENGTH: 7
<212> TYPE: PRT
<213> ORGANISM: Homo sapiens

<400> SEQUENCE: 7

Ser Ser Ser Tyr Tyr Trp Gly
1               5


<210> SEQ ID NO 8
<211> LENGTH: 16
<212> TYPE: PRT
<213> ORGANISM: Homo sapiens

<400> SEQUENCE: 8

Ser Ile Tyr Tyr Ser Gly Ser Thr Tyr Tyr Asn Pro Ser Leu Lys Ser
1               5                   10                  15


<210> SEQ ID NO 9
<211> LENGTH: 11
<212> TYPE: PRT
<213> ORGANISM: Homo sapiens
```

<400> SEQUENCE: 9

His Asp Ala Ala Thr Ala Gly Leu Phe Asp Tyr
1 5 10

<210> SEQ ID NO 10
<211> LENGTH: 7
<212> TYPE: PRT
<213> ORGANISM: Homo sapiens

<400> SEQUENCE: 10

Ser Gly Ser Tyr Tyr Trp Gly
1 5

<210> SEQ ID NO 11
<211> LENGTH: 16
<212> TYPE: PRT
<213> ORGANISM: Homo sapiens

<400> SEQUENCE: 11

Ser Ile Tyr Tyr Ser Gly Trp Thr Tyr Tyr Asn Pro Ser Leu Lys Ser
1 5 10 15

<210> SEQ ID NO 12
<211> LENGTH: 11
<212> TYPE: PRT
<213> ORGANISM: Homo sapiens

<400> SEQUENCE: 12

His Glu Gly Ala Thr Ala Gly Leu Phe Asp Tyr
1 5 10

<210> SEQ ID NO 13
<211> LENGTH: 7
<212> TYPE: PRT
<213> ORGANISM: Homo sapiens

<400> SEQUENCE: 13

Ser Ser Ser Tyr Phe Trp Gly
1 5

<210> SEQ ID NO 14
<211> LENGTH: 16
<212> TYPE: PRT
<213> ORGANISM: Homo sapiens

<400> SEQUENCE: 14

Ser Ile Tyr Tyr Ser Gly Arg Thr Tyr Tyr Asn Pro Ser Leu Lys Ser
1 5 10 15

<210> SEQ ID NO 15
<211> LENGTH: 11
<212> TYPE: PRT
<213> ORGANISM: Homo sapiens

<400> SEQUENCE: 15

His Ser Gly Ala Thr Ala Gly Leu Phe Asp Tyr
1 5 10

<210> SEQ ID NO 16
<211> LENGTH: 11
<212> TYPE: PRT
<213> ORGANISM: Homo sapiens

<400> SEQUENCE: 16

His Glu Gly Ala Val Ala Gly Leu Phe Asp Tyr
1 5 10

<210> SEQ ID NO 17
<211> LENGTH: 11
<212> TYPE: PRT
<213> ORGANISM: Homo sapiens

<400> SEQUENCE: 17

His Ser Gly Ala Val Ala Gly Leu Phe Asp Tyr
1 5 10

<210> SEQ ID NO 18
<211> LENGTH: 11
<212> TYPE: PRT
<213> ORGANISM: Homo sapiens

<400> SEQUENCE: 18

His Asp Ala Ala Val Ala Gly Leu Phe Asp Tyr
1 5 10

<210> SEQ ID NO 19
<211> LENGTH: 11
<212> TYPE: PRT
<213> ORGANISM: Homo sapiens

<400> SEQUENCE: 19

His Asp Gly Ala Thr Ala Gly Leu Phe Asp Tyr
1 5 10

<210> SEQ ID NO 20
<211> LENGTH: 11
<212> TYPE: PRT
<213> ORGANISM: Homo sapiens

<400> SEQUENCE: 20

His Gln Gly Ala Thr Ala Gly Leu Phe Asp Tyr
1 5 10

<210> SEQ ID NO 21
<211> LENGTH: 11
<212> TYPE: PRT
<213> ORGANISM: Homo sapiens

<400> SEQUENCE: 21

His His Gly Ala Thr Ala Gly Leu Phe Asp Tyr
1 5 10

<210> SEQ ID NO 22
<211> LENGTH: 11
<212> TYPE: PRT
<213> ORGANISM: Homo sapiens

<400> SEQUENCE: 22

His Trp Gly Ala Thr Ala Gly Leu Phe Asp Tyr
1 5 10

<210> SEQ ID NO 23
<211> LENGTH: 11
<212> TYPE: PRT
<213> ORGANISM: Homo sapiens

<400> SEQUENCE: 23

His Tyr Gly Ala Thr Ala Gly Leu Phe Asp Tyr 1 5 10

<210> SEQ ID NO 24
<211> LENGTH: 11
<212> TYPE: PRT
<213> ORGANISM: Homo sapiens

<400> SEQUENCE: 24

Gly Gly Asn Asn Ile Gly Ser Lys Ser Val His
1 5 10

<210> SEQ ID NO 25
<211> LENGTH: 7
<212> TYPE: PRT
<213> ORGANISM: Homo sapiens

<400> SEQUENCE: 25

Asp Asp Ser Asp Arg Pro Ser
1 5

<210> SEQ ID NO 26
<211> LENGTH: 11
<212> TYPE: PRT
<213> ORGANISM: Homo sapiens

<400> SEQUENCE: 26

Gln Val Trp Asp Ser Ser Ser Asp His Val Val
1 5 10

<210> SEQ ID NO 27
<211> LENGTH: 122
<212> TYPE: PRT
<213> ORGANISM: Homo sapiens

<400> SEQUENCE: 27

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

Ser Tyr Phe Trp Gly Trp Ile Arg Gln Pro Pro Gly Lys Gly Leu Glu
35 40 45

Trp Ile Gly Ser Ile Tyr Tyr Ser Gly Ile Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His Asp Gly Ala Val Ala Gly Leu Phe Asp Tyr Trp Gly
100 105 110

Gln Gly Thr Leu Val Thr Val Ser Ser Ala
115 120

<210> SEQ ID NO 28
<211> LENGTH: 108
<212> TYPE: PRT
<213> ORGANISM: Homo sapiens

<400> SEQUENCE: 28

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val

```
            20                  25                  30

His Trp Tyr Gln Gln Pro Pro Gly Gln Ala Pro Val Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
                85                  90                  95

Val Val Phe Gly Gly Gly Thr Lys Leu Thr Val Leu
            100                 105


<210> SEQ ID NO 29
<211> LENGTH: 122
<212> TYPE: PRT
<213> ORGANISM: Homo sapiens

<400> SEQUENCE: 29

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Ala Ala Thr Ala Gly Leu Phe Asp Tyr Trp Gly
            100                 105                 110

Gln Gly Thr Leu Val Thr Val Ser Ser Ala
        115                 120


<210> SEQ ID NO 30
<211> LENGTH: 108
<212> TYPE: PRT
<213> ORGANISM: Homo sapiens

<400> SEQUENCE: 30

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105
```

<210> SEQ ID NO 31
<211> LENGTH: 122
<212> TYPE: PRT
<213> ORGANISM: Homo sapiens

<400> SEQUENCE: 31

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

Ser Tyr Tyr Trp Gly Trp Ile Arg Gln Pro Pro Gly Lys Gly Leu Glu
35 40 45

Trp Ile Gly Ser Ile Tyr Tyr Ser Gly Ile Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His Glu Gly Ala Thr Ala Gly Leu Phe Asp Tyr Trp Gly
100 105 110

Gln Gly Thr Leu Val Thr Val Ser Ser Ala
115 120

<210> SEQ ID NO 32
<211> LENGTH: 122
<212> TYPE: PRT
<213> ORGANISM: Homo sapiens

<400> SEQUENCE: 32

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

Ser Tyr Tyr Trp Gly Trp Ile Arg Gln Pro Pro Gly Lys Gly Leu Glu
35 40 45

Trp Ile Gly Ser Ile Tyr Tyr Ser Gly Ile Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His Ser Gly Ala Thr Ala Gly Leu Phe Asp Tyr Trp Gly
100 105 110

Gln Gly Thr Leu Val Thr Val Ser Ser Ala
115 120

<210> SEQ ID NO 33
<211> LENGTH: 122
<212> TYPE: PRT
<213> ORGANISM: Homo sapiens

<400> SEQUENCE: 33

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

```
Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala
        115                 120


<210> SEQ ID NO 34
<211> LENGTH: 122
<212> TYPE: PRT
<213> ORGANISM: Homo sapiens

<400> SEQUENCE: 34

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala
        115                 120


<210> SEQ ID NO 35
<211> LENGTH: 122
<212> TYPE: PRT
<213> ORGANISM: Homo sapiens

<400> SEQUENCE: 35

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala
        115                 120
```

<210> SEQ ID NO 36
<211> LENGTH: 122
<212> TYPE: PRT
<213> ORGANISM: Homo sapiens

<400> SEQUENCE: 36

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

Ser Tyr Phe Trp Gly Trp Ile Arg Gln Pro Pro Gly Lys Gly Leu Glu
35 40 45

Trp Ile Gly Ser Ile Tyr Tyr Ser Gly Ile Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His Glu Gly Ala Val Ala Gly Leu Phe Asp Tyr Trp Gly
100 105 110

Gln Gly Thr Leu Val Thr Val Ser Ser Ala
115 120

<210> SEQ ID NO 37
<211> LENGTH: 122
<212> TYPE: PRT
<213> ORGANISM: Homo sapiens

<400> SEQUENCE: 37

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

Ser Tyr Phe Trp Gly Trp Ile Arg Gln Pro Pro Gly Lys Gly Leu Glu
35 40 45

Trp Ile Gly Ser Ile Tyr Tyr Ser Gly Ile Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His Ser Gly Ala Val Ala Gly Leu Phe Asp Tyr Trp Gly
100 105 110

Gln Gly Thr Leu Val Thr Val Ser Ser Ala
115 120

<210> SEQ ID NO 38
<211> LENGTH: 122
<212> TYPE: PRT
<213> ORGANISM: Homo sapiens

<400> SEQUENCE: 38

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

```
Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Ala Ala Val Ala Gly Leu Phe Asp Tyr Trp Gly
            100                 105                 110

Gln Gly Thr Leu Val Thr Val Ser Ser Ala
        115                 120


<210> SEQ ID NO 39
<211> LENGTH: 122
<212> TYPE: PRT
<213> ORGANISM: Homo sapiens

<400> SEQUENCE: 39

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 40
<211> LENGTH: 122
<212> TYPE: PRT
<213> ORGANISM: Homo sapiens

<400> SEQUENCE: 40

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110
```

```
Gln Gly Thr Leu Val Thr Val Ser Ser Ala
        115                 120


<210> SEQ ID NO 41
<211> LENGTH: 122
<212> TYPE: PRT
<213> ORGANISM: Homo sapiens

<400> SEQUENCE: 41

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Ala Ala Val Ala Gly Leu Phe Asp Tyr Trp Gly
            100                 105                 110

Gln Gly Thr Leu Val Thr Val Ser Ser Ala
        115                 120


<210> SEQ ID NO 42
<211> LENGTH: 122
<212> TYPE: PRT
<213> ORGANISM: Homo sapiens

<400> SEQUENCE: 42

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Glu Gly Ala Val Ala Gly Leu Phe Asp Tyr Trp Gly
            100                 105                 110

Gln Gly Thr Leu Val Thr Val Ser Ser Ala
        115                 120


<210> SEQ ID NO 43
<211> LENGTH: 122
<212> TYPE: PRT
<213> ORGANISM: Homo sapiens

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
```

```
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 44
<211> LENGTH: 122
<212> TYPE: PRT
<213> ORGANISM: Homo sapiens

<400> SEQUENCE: 44

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Trp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 45
<211> LENGTH: 122
<212> TYPE: PRT
<213> ORGANISM: Homo sapiens

<400> SEQUENCE: 45

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Gln Gly Ala Thr Ala Gly Leu Phe Asp Tyr Trp Gly
```

```
            100                 105                 110

Gln Gly Thr Leu Val Thr Val Ser Ser Ala
        115                 120


<210> SEQ ID NO 46
<211> LENGTH: 122
<212> TYPE: PRT
<213> ORGANISM: Homo sapiens

<400> SEQUENCE: 46

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His His Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 47
<211> LENGTH: 122
<212> TYPE: PRT
<213> ORGANISM: Homo sapiens

<400> SEQUENCE: 47

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Trp Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 48
<211> LENGTH: 122
<212> TYPE: PRT
<213> ORGANISM: Homo sapiens

<400> SEQUENCE: 48

Gln Leu Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Tyr Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 49
<211> LENGTH: 122
<212> TYPE: PRT
<213> ORGANISM: Homo sapiens

<400> SEQUENCE: 49

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Gln Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 50
<211> LENGTH: 122
<212> TYPE: PRT
<213> ORGANISM: Homo sapiens

<400> SEQUENCE: 50

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

```
Cys Ala Arg His His Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 51
<211> LENGTH: 122
<212> TYPE: PRT
<213> ORGANISM: Homo sapiens

<400> SEQUENCE: 51

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Tyr Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 52
<211> LENGTH: 122
<212> TYPE: PRT
<213> ORGANISM: Homo sapiens

<400> SEQUENCE: 52

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Trp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Gln Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 53
<211> LENGTH: 122
<212> TYPE: PRT
<213> ORGANISM: Homo sapiens

<400> SEQUENCE: 53
```

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Trp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His His Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 54
<211> LENGTH: 122
<212> TYPE: PRT
<213> ORGANISM: Homo sapiens

<400> SEQUENCE: 54

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Trp Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Tyr Gly Ala Thr Ala Gly Leu Phe Asp Tyr Trp Gly
            100                 105                 110

Gln Gly Thr Leu Val Thr Val Ser Ser Ala
        115                 120


<210> SEQ ID NO 55
<211> LENGTH: 452
<212> TYPE: PRT
<213> ORGANISM: Homo sapiens

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80
```

```
Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450


<210> SEQ ID NO 56
<211> LENGTH: 215
<212> TYPE: PRT
<213> ORGANISM: Homo sapiens

<400> SEQUENCE: 56
```

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 57
<211> LENGTH: 122
<212> TYPE: PRT
<213> ORGANISM: Homo sapiens

<400> SEQUENCE: 57

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala
        115                 120


<210> SEQ ID NO 58
<211> LENGTH: 122
<212> TYPE: PRT
```

<213> ORGANISM: Homo sapiens

<400> SEQUENCE: 58

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Phe Trp Gly Trp Ile Arg Gln Pro Pro Gly Lys Gly Leu Glu
35 40 45

Trp Ile Gly Ser Ile Tyr Tyr Ser Gly Ile Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His Asp Gly Ala Thr Ala Gly Leu Phe Asp Tyr Trp Gly
100 105 110

Gln Gly Thr Leu Val Thr Val Ser Ser Ala
115 120

<210> SEQ ID NO 59
<211> LENGTH: 5
<212> TYPE: PRT
<213> ORGANISM: Homo sapiens

<400> SEQUENCE: 59

Thr Tyr Ala Met Asn
1 5

<210> SEQ ID NO 60
<211> LENGTH: 19
<212> TYPE: PRT
<213> ORGANISM: Homo sapiens

<400> SEQUENCE: 60

Arg Ile Arg Ser Lys Tyr Asn Asn Tyr Ala Thr Tyr Tyr Ala Ala Ser
1 5 10 15

Val Lys Gly

<210> SEQ ID NO 61
<211> LENGTH: 14
<212> TYPE: PRT
<213> ORGANISM: Homo sapiens

<400> SEQUENCE: 61

His Gly Asn Phe Gly Asn Ser Tyr Val Ser Trp Phe Ala Tyr
1 5 10

<210> SEQ ID NO 62
<211> LENGTH: 14
<212> TYPE: PRT
<213> ORGANISM: Homo sapiens

<400> SEQUENCE: 62

Arg Ser Ser Thr Gly Ala Val Thr Thr Ser Asn Tyr Ala Asn
1 5 10

<210> SEQ ID NO 63
<211> LENGTH: 7
<212> TYPE: PRT
<213> ORGANISM: Homo sapiens

<400> SEQUENCE: 63

Gly Thr Asn Lys Arg Ala Pro
1 5

<210> SEQ ID NO 64
<211> LENGTH: 9
<212> TYPE: PRT
<213> ORGANISM: Homo sapiens

<400> SEQUENCE: 64

Ala Leu Trp Tyr Ser Asn Leu Trp Val
1 5

<210> SEQ ID NO 65
<211> LENGTH: 448
<212> TYPE: PRT
<213> ORGANISM: Homo sapiens

<400> SEQUENCE: 65

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

Ser Tyr Phe Trp Gly Trp Ile Arg Gln Pro Pro Gly Lys Gly Leu Glu
35 40 45

Trp Ile Gly Ser Ile Tyr Tyr Ser Gly Ile Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His Asp Gly Ala Val Ala Gly Leu Phe Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Cys Ser Arg Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Lys Thr Tyr Thr Cys Asn Val Asp His
195 200 205

Lys Pro Ser Asn Thr Lys Val Asp Lys Arg Val Glu Ser Lys Tyr Gly
210 215 220

Pro Pro Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser Gln Glu Asp Pro
260 265 270

Glu Val Gln Phe Asn Trp Tyr Val Asp Gly Val Glu Val His Asn Ala
275 280 285

```
Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 66
<211> LENGTH: 214
<212> TYPE: PRT
<213> ORGANISM: Homo sapiens

<400> SEQUENCE: 66

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Pro Pro Gly Gln Ala Pro Val Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 67
<211> LENGTH: 448
<212> TYPE: PRT
<213> ORGANISM: Homo sapiens

<400> SEQUENCE: 67

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

Ser Tyr Phe Trp Gly Trp Ile Arg Gln Pro Pro Gly Lys Gly Leu Glu
35 40 45

Trp Ile Gly Ser Ile Tyr Tyr Ser Gly Ile Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His Asp Gly Ala Val Ala Gly Leu Phe Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Cys Ser Arg Ser Thr Ser Glu Ser Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Lys Thr Tyr Thr Cys Asn Val Asp His
195 200 205

Lys Pro Ser Asn Thr Lys Val Asp Lys Arg Val Glu Ser Lys Tyr Gly
210 215 220

Pro Pro Cys Pro Pro Cys Pro Ala Pro Glu Ala Ala Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser Gln Glu Asp Pro
260 265 270

Glu Val Gln Phe Asn Trp Tyr Val Asp Gly Val Glu Val His Asn Ala
275 280 285

Lys Thr Lys Pro Arg Glu Glu Gln Phe Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Gly Leu Pro Ser Ser Ile Glu Lys Thr
325 330 335

Ile Ser Lys Ala Lys Gly Gln Pro Arg Glu Pro Gln Val Tyr Thr Leu
340 345 350

Pro Pro Ser Gln Glu Glu Met Thr Lys Asn Gln Val Ser Leu Thr Cys
355 360 365

Leu Val Lys Gly Phe Tyr Pro Ser Asp Ile Ala Val Glu Trp Glu Ser

```
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 68
<211> LENGTH: 448
<212> TYPE: PRT
<213> ORGANISM: Homo sapiens

<400> SEQUENCE: 68

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 69
<211> LENGTH: 448
<212> TYPE: PRT
<213> ORGANISM: Homo sapiens

<400> SEQUENCE: 69

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 70
<211> LENGTH: 448
<212> TYPE: PRT
<213> ORGANISM: Homo sapiens

<400> SEQUENCE: 70

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 71
<211> LENGTH: 448
<212> TYPE: PRT
<213> ORGANISM: Homo sapiens

<400> SEQUENCE: 71

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

```
Cys Ala Arg His Asp Gly Ala Thr Ala Gly Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 72
<211> LENGTH: 448
<212> TYPE: PRT
<213> ORGANISM: Homo sapiens

<400> SEQUENCE: 72

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30
```

```
Ser Tyr Phe Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 73
<211> LENGTH: 327
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 73

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 74
<211> LENGTH: 330
<212> TYPE: PRT
<213> ORGANISM: Homo sapiens

<400> SEQUENCE: 74

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 75
<211> LENGTH: 230
<212> TYPE: PRT
<213> ORGANISM: Homo sapiens

<400> SEQUENCE: 75

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Gly
20 25 30

```
Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

His His His His His His
225                 230


<210> SEQ ID NO 76
<211> LENGTH: 214
<212> TYPE: PRT
<213> ORGANISM: Homo sapiens

<400> SEQUENCE: 76

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Pro Pro Gly Gln Ala Pro Val Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
```

-continued

```
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 77
<211> LENGTH: 5
<212> TYPE: PRT
<213> ORGANISM: Homo sapiens

<400> SEQUENCE: 77

Gly Ala Val Ala Gly
1               5
```

We claim:

1. A recombinant antibody, or an antigen-binding fragment thereof, that binds immunospecifically to BCMA, wherein the antibody has a heavy chain and a light chain, said heavy chain and light chain comprising:

a heavy chain complementarity determining region 1 (CDR1) having the amino acid sequence of SEQ ID NO: 4, a heavy chain CDR2 having the amino acid sequence of SEQ ID NO: 5, and a heavy chain CDR3 having the amino acid sequence of SEQ ID NO: 6, a light chain CDR1 having the amino acid sequence of SEQ ID NO: 24, a light chain CDR2 having the amino acid sequence of SEQ ID NO: 25, and a light chain CDR3 having the amino acid sequence of SEQ ID NO: 26.

2. The antibody or antigen-binding fragment of claim 1, wherein the heavy chain of the antibody comprises the amino acid sequence of SEQ ID NO: 27, and the light chain of the antibody comprises the amino acid sequence of SEQ ID NO:28.

3. The antibody or antigen-binding fragment of any one of claims 1 and 2, wherein the antibody or antigen-binding fragment thereof binds to the extracellular domain of human BCMA.

4. The antibody or antigen-binding fragment of any one of claims 1 and 2, wherein the antibody or antigen-binding fragment is a [human] *humanized* antibody or antigen-binding fragment.

5. The antigen binding fragment of any one of claims 1 and 2, wherein the antigen binding fragment is a Fab fragment, a Fab2 fragment, or a single chain antibody.

6. The antibody or antigen-binding fragment of any one of claims 1 and 2, wherein the antibody or antigen-binding fragment thereof inhibits the interaction of BCMA and APRIL.

7. The antibody or antigen-binding fragment of claim 6, wherein the antibody or antigen-binding fragment exhibits an $IC_{50}$ for the interaction of BCMA and APRIL of about 5.9 nM as measured by ELISA.

8. The antibody or antigen-binding fragment of any one of claims 1 and 2, wherein the antibody or antigen-binding fragment thereof is an IgG.

9. The antibody or antigen-binding fragment of any one of claims 1 and 2, is an IgG4 isotype.

[10. The antibody of claim 9 wherein the IgG4 has a S228P substitution, a L234A substitution and a L235A substitution in its Fc region.]

11. The antibody or antigen-binding fragment of any one of claims 1 and 2, wherein the antibody or antigen-binding fragment thereof immunospecifically binds human BCMA and cross reacts to cynomolgus monkey BCMA.

12. The antibody or antigen-binding fragment of any one of claims 1 and 2, wherein the antibody or antigen-binding fragment thereof binds BCMA on the surface of human myeloma cells.

13. The antibody or antigen-binding fragment of any one of claims 1 and 2, wherein the antibody or antigen-binding fragment thereof binds BCMA on the surface of human multiple myeloma cells.

14. A recombinant cell expressing the antibody or antigen-binding fragment of any one of claims 1 and 2.

15. The cell of claim 14 wherein the cell is a hybridoma.

16. The cell of claim 14 wherein the antibody is recombinantly produced.

*17. The antibody or antigen-binding fragment of claim 1, wherein the heavy chain of the antibody comprises the amino acid sequence of SEQ ID NO: 65.*

*18. The antibody or antigen-binding fragment of claim 1, wherein the light chain of the antibody comprises the amino acid sequence of SEQ ID NO: 76.*

*19. The antibody or antigen-binding fragment of claim 1, wherein the heavy chain of the antibody comprises the amino acid sequence of SEQ ID NO: 65, and wherein the light chain of the antibody comprises the amino acid sequence of SEQ ID NO: 76.*

*20. A recombinant cell expressing the antibody or antigen-binding fragment of any one of claims 17, 18 or 19.*

*21. The cell of claim 20 wherein the cell is a hybridoma.*

*22. The cell of claim 20 wherein the antibody is recombinantly produced.*

*23. A recombinant antibody that binds immunospecifically to BCMA, wherein the antibody has a heavy chain and a light chain, said heavy chain and light chain comprising:*

*a heavy chain complementarity determining region 1 (CDR1) having the amino acid sequence of SEQ ID NO: 4, a heavy chain CDR2 having the amino acid sequence of SEQ ID NO: 5, and a heavy chain CDR3 having the amino acid sequence of SEQ ID NO: 6, a light chain CDR1 having the amino acid sequence of*

*SEQ ID NO: 24, a light chain CDR2 having the amino acid sequence of SEQ ID NO: 25, and a light chain CDR3 having the amino acid sequence of SEQ ID NO: 26,*

*wherein the antibody is a humanized antibody and is an IgG4 isotype.*

*24. The antibody of claim 23, wherein the heavy chain of the antibody comprises the amino acid sequence of SEQ ID NO: 27, and the light chain of the antibody comprises the amino acid sequence of SEQ ID NO: 28.*

*25. The antibody of any one of claims 23 and 24, wherein the antibody binds to the extracellular domain of human BCMA.*

*26. The antibody of any one of claims 23 and 24, wherein the antibody inhibits the interaction of BCMA and APRIL.*

*27. The antibody of claim 26, wherein the antibody exhibits an $IC_{50}$ for the interaction of BCMA and APRIL of about 5.9 nM as measured by ELISA.*

*28. The antibody of any one of claims 23 and 24, wherein the antibody immunospecifically binds human BCMA and cross reacts to cynomolgus monkey BCMA.*

*29. The antibody of any one of claims 23 and 24, wherein the antibody binds BCMA on the surface of human myeloma cells.*

*30. The antibody of any one of claims 23 and 24, wherein the antibody binds BCMA on the surface of human multiple myeloma cells.*

*31. A recombinant cell expressing the antibody of any one of claims 23 and 24, wherein the cell is a hybridoma.*

*32. The antibody of claim 23, wherein the heavy chain of the antibody comprises the amino acid sequence of SEQ ID NO: 65.*

*33. The antibody of claim 23, wherein the light chain of the antibody comprises the amino acid sequence of SEQ ID NO: 76.*

*34. The antibody of claim 23, wherein the heavy chain of the antibody comprises the amino acid sequence of SEQ ID NO: 65, and wherein the light chain of the antibody comprises the amino acid sequence of SEQ ID NO: 76.*

*35. A recombinant cell expressing the antibody of any one of claims 32, 33, and 34, wherein the cell is a hybridoma.*

* * * * *